(12) United States Patent
Nagy et al.

(10) Patent No.: US 9,771,548 B2
(45) Date of Patent: *Sep. 26, 2017

(54) COMPOSITIONS CONTAINING ONE OR MORE POLY ALPHA-1,3-GLUCAN ETHER COMPOUNDS

(71) Applicant: E I DU PONT DE NEMOURS AND COMPANY, Wilmington, DE (US)

(72) Inventors: Kevin D Nagy, Wilmington, DE (US); Perry G Caimi, Kennett Square, PA (US); T Joseph Dennes, Parkesburg, PA (US); Susan Marie Hennessey, Avondale, PA (US); Ayrookaran J. Poulose, Belmont, CA (US); Jayme L Paullin, Claymont, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/741,769

(22) Filed: Jun. 17, 2015

(65) Prior Publication Data

US 2015/0368594 A1 Dec. 24, 2015

Related U.S. Application Data

(60) Provisional application No. 62/014,318, filed on Jun. 19, 2014.

(51) Int. Cl.
| | | |
|---|---|---|
| *D06M 16/00* | (2006.01) |
| *C11D 3/386* | (2006.01) |
| *C11D 3/22* | (2006.01) |
| *A61K 8/66* | (2006.01) |
| *A61K 8/73* | (2006.01) |
| *A61Q 19/00* | (2006.01) |

(52) U.S. Cl.
CPC ............ *C11D 3/38645* (2013.01); *A61K 8/66* (2013.01); *A61K 8/73* (2013.01); *A61Q 19/00* (2013.01); *C11D 3/225* (2013.01); *D06M 16/00* (2013.01); *A61K 2800/10* (2013.01)

(58) Field of Classification Search
CPC ........ A61K 2800/10; A61K 8/66; A61K 8/73; A61Q 19/00; C11D 3/225; C11D 3/38645; D06M 16/00

See application file for complete search history.

(56) References Cited

U.S. PATENT DOCUMENTS

| | | |
|---|---|---|
| 4,435,307 A | 3/1984 | Barbesgaard et al. |
| 4,580,421 A | 4/1986 | Babuin et al. |
| 4,689,297 A | 8/1987 | Good et al. |
| 4,794,661 A | 1/1989 | Durazzani |
| 5,324,649 A | 6/1994 | Arnold et al. |
| 5,558,861 A | 9/1996 | Yamanaka et al. |
| 5,648,263 A | 7/1997 | Schulein et al. |
| 5,691,178 A | 11/1997 | Schulein et al. |
| 5,776,757 A | 7/1998 | Schulein et al. |
| 5,814,501 A | 9/1998 | Becker et al. |
| 5,945,394 A | 8/1999 | Sajic et al. |
| 5,952,205 A | 9/1999 | Catani et al. |
| 6,242,225 B1 | 6/2001 | Catani et al. |
| 6,342,486 B1 | 1/2002 | Zulli et al. |
| 6,579,840 B1 | 6/2003 | Heltovics |
| 6,660,502 B2 | 12/2003 | Catani et al. |
| 6,730,646 B1 | 5/2004 | Waschenbach et al. |
| 7,000,000 B1 | 2/2006 | O'Brien |
| 7,001,878 B2 | 2/2006 | De Buzzaccarini et al. |
| 7,012,053 B1 | 3/2006 | Barnabas et al. |
| 7,056,880 B2 | 6/2006 | Wang et al. |
| 7,351,573 B2 | 4/2008 | Dunn-Coleman |
| 7,534,759 B2 | 5/2009 | Wahl et al. |
| 7,576,048 B2 | 8/2009 | Gray et al. |
| 7,604,974 B2 | 10/2009 | Jones et al. |
| 8,076,279 B2 | 12/2011 | Brand et al. |
| 9,351,910 B2 | 5/2016 | Chen et al. |
| 2002/0022006 A1 | 2/2002 | Jung |
| 2004/0151681 A1 | 8/2004 | Busk et al. |
| 2006/0134025 A1 | 6/2006 | Trivedi et al. |
| 2006/0134417 A1 | 6/2006 | Takaha et al. |
| 2008/0057007 A1 | 3/2008 | Leonhardt et al. |
| 2009/0209445 A1 | 8/2009 | Panandiker et al. |
| 2010/0081598 A1 | 4/2010 | Sharma et al. |
| 2012/0168698 A1 | 7/2012 | Hammond |
| 2013/0236630 A1 | 9/2013 | Brizius |

(Continued)

FOREIGN PATENT DOCUMENTS

| | | |
|---|---|---|
| CN | 1283633 A | 2/2001 |
| EP | 0035478 A1 | 9/1981 |

(Continued)

OTHER PUBLICATIONS

Related U.S. Appl. No. 14/741,813, filed Jun. 17, 2015.
Corresponding PCT Application; International Application No. PCT/US2015/036193, Filed Jun. 17, 2015.
Related PCT Application, International Application No. PCT/US2015/036497, Filed Jun. 17, 2015.
Abo et al., Peptide Sequences for Sucrose Splitting and Glucan Binding Within Streptococcus sobrinus Glucosyltransferase (Water-Insoluble Glucan Synthetase), Journal of Bacteriology, vol. 173, No. 3 (1991), pp. 989-996.
Bao et al., Chemical Modifications of the (1->3)-α-D-Glucan From Spores of Ganoderma Lucidum and Investigation of Their Physicochemical Properties and Immunological Activity, Carbohydrate Research, vol. 336 (2001), pp. 127-140.

(Continued)

Primary Examiner — Susan Hanley

(57) ABSTRACT

Compositions comprising cellulase and at least one poly alpha-1,3-glucan ether compound having a degree of substitution with an organic group of about 0.05-3.0 are disclosed. Such compositions can be dry or aqueous, the latter of which can have a viscosity of at least about 10 cPs. The disclosed composition can be in the form of a personal care product, household product, or industrial product, for example. Also disclosed are a method for preparing an aqueous composition comprising cellulase and a poly alpha-1,3-glucan ether compound, and a method of treating a material such as fabric by contacting it with this aqueous composition.

22 Claims, No Drawings

(56) References Cited

U.S. PATENT DOCUMENTS

| | | |
|---|---|---|
| 2013/0244288 A1 | 9/2013 | O'Brien et al. |
| 2014/0087431 A1 | 3/2014 | Payne et al. |
| 2014/0179913 A1 | 6/2014 | Paullin et al. |
| 2015/0080220 A1 | 3/2015 | Yao et al. |
| 2015/0232785 A1 | 8/2015 | Paullin et al. |
| 2015/0368595 A1 | 12/2015 | Nagy et al. |

FOREIGN PATENT DOCUMENTS

| | | |
|---|---|---|
| EP | 0819703 A2 | 1/1998 |
| GB | 2095275 A | 2/1982 |
| GB | 2432852 A | 6/2007 |
| JP | 2013091771 | 5/2013 |
| WO | 2013026182 A1 | 2/2013 |
| WO | 2013036968 A1 | 3/2013 |
| WO | 2013068771 A1 | 5/2013 |
| WO | 2013158992 A1 | 10/2013 |
| WO | 2014099724 A1 | 6/2014 |
| WO | 2015095046 A1 | 6/2015 |
| WO | 2015095358 A1 | 6/2015 |

OTHER PUBLICATIONS

Cantarel et al., The Carbohydrate-Active Enzymes Database (CAZY): An Expert Resource for Glycogenomics, Nucleic Acids Research, vol. 37 (2009), Database Issue, pp. D-233-D238.

Jeanes et al., Characterization and Classification of Dextrans From Ninety-Six Strains of Bacteria, Contributino From the Starch and Dextrose Section, Northern Utilization Research Branch, vol. 76 (1954), pp. 5041-5052.

Construction of a Fully Active Truncated Alternansucrase Partially Deleted of Its Carboxy-Terminal Domain, FEBS Letters, vol. 580 (2006), pp. 763-768.

Kiho et al., (1->3)-α-D-Glucan From an Alkaline Extract of Agrocybe Cylindracea and Antitumor Activity of Its O-(Carboxy-Methyl)ated Derivatives, Carbohydrate Research, vol. 189 (1989), pp. 273-279.

Konishi et al., Structure and Enzymatic Properties of Genetically Truncated Forms of the Water-Insoluble Glucan-Synthesizing Glucosyltransferase From *Streptococcus sobrinus*, J. Biochem, vol. 126 (1999), pp. 237-295.

Monchois et al., Isolation of an Active Catalytic Core of *Streptococcus downei* MFE28 GTF-I Glucosyltranserase, Journal of Bacteriology, vol. 181, No. 7 (1999), pp. 2290-2292.

Monchois et al., Glucansucrases: Mechanism of Action and Structure-Function Relationships, FEMS Microbiology Review, vol. 23 (1999), pp. 131-151.

Ogawa et al., X-Ray Diffraction Data for (1->3)-α-D-Glucan Triacetate, Carbohydrate Polymers, vol. 3 (1983), pp. 287-297.

Ogawa et al., Crystal Structure of (1->3)-α-D-Glucan, In Fiber Defraction Methods, French, A. et al., ACS Symposium Series: American Chemical Society, Washington, DC (1980), pp. 353-362.

Shida et al., A (1->3)-α-D-Glucan Isolated From the Fruit Bodies of Lentinus Edodes, Carbohydrate Research, vol. 60 )1978), pp. 117-127.

Simpson et al., Four Glucosyltransferases, GTFJ, GTFK, GTFL and GTFM, From *Streptococcus salivarius* ATCC 25975, Microbiology, vol. 141 (1995), pp. 1451-1460.

Yui et al., Molecular and Crystal Structure of (1->3)-α-D-Glucan Triacetate, Int. J. Macromol., vol. 14 (1992), pp. 87-96.

COMPOSITIONS CONTAINING ONE OR MORE POLY ALPHA-1,3-GLUCAN ETHER COMPOUNDS

This application claims the benefit of U.S. Provisional Application No. 62/014,318 (filed Jun. 19, 2014), which is incorporated herein by reference in its entirety.

FIELD OF INVENTION

This invention is in the field of personal care, household products, and industrial products. For example, this invention pertains to compositions comprising cellulase and a poly alpha-1,3-glucan ether compound.

BACKGROUND

Driven by a desire to find new structural polysaccharides using enzymatic syntheses or genetic engineering of microorganisms or plant hosts, researchers have discovered polysaccharides that are biodegradable, and that can be made economically from renewable resource-based feedstocks. One such polysaccharide is poly alpha-1,3-glucan, a glucan polymer characterized by having alpha-1,3-glycosidic linkages. This polymer has been isolated by contacting an aqueous solution of sucrose with a glucosyltransferase enzyme isolated from *Streptococcus salivarius* (Simpson et al., *Microbiology* 141:1451-1460, 1995).

U.S. Pat. No. 7,000,000 disclosed the preparation of a polysaccharide fiber comprising hexose units, wherein at least 50% of the hexose units within the polymer were linked via alpha-1,3-glycosidic linkages using an *S. salivarius* gtfJ enzyme. This enzyme utilizes sucrose as a substrate in a polymerization reaction producing poly alpha-1,3-glucan and fructose as end-products (Simpson et al., 1995). The disclosed polymer formed a liquid crystalline solution when it was dissolved above a critical concentration in a solvent or in a mixture comprising a solvent. From this solution continuous, strong, cotton-like fibers, highly suitable for use in textiles, were spun and used.

Modified cellulosic polymers have been used in detergent formulations to provide a variety of benefits including anti-redeposition and fabric care benefits (U.S. Pat. Nos. 7,012,053, 7,056,880, 6,579,840, 7,534,759, 7,576,048). Some of these polymers have also been used to adjust the viscosity of the detergent formulation itself. However, lack of stability of cellulose-based polymers to cellulases is a major limitation for using these polymers in detergent formulations. Enzymes used in detergents often contain trace amounts of cellulase. Also, cellulase is generally included in detergent formulations to provide color clarification and pill removal benefits. But the incompatibility of cellulosic polymers and cellulase enzymes limits the use of these components together in a formulation.

SUMMARY OF INVENTION

In one embodiment, the disclosure concerns a composition comprising a cellulase and a poly alpha-1,3-glucan ether compound represented by the structure:

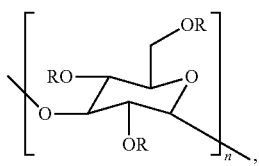

wherein
(i) n is at least 6,
(ii) each R is independently an H or an organic group, and
(iii) the compound has a degree of substitution of about 0.05 to about 3.0.

In a second embodiment, at least one organic group is selected from the group consisting of carboxy alkyl group, hydroxy alkyl group, and alkyl group. At least one organic group is selected from the group consisting of carboxymethyl, hydroxypropyl, dihydroxypropyl, hydroxyethyl, methyl, and ethyl group in a third embodiment. The organic group is a carboxymethyl group in a fourth embodiment.

In a fifth embodiment, the composition is in the form of a personal care product, household product, or industrial product. The composition is a fabric care product in a sixth embodiment.

In a seventh embodiment, the composition is an aqueous composition. The composition has a viscosity of at least about 10 cPs in an eighth embodiment.

In a ninth embodiment, the disclosure concerns a method for preparing an aqueous composition. This method comprises contacting an aqueous composition with a poly alpha-1,3-glucan ether compound represented by the structure:

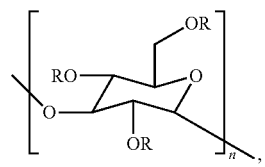

wherein
(i) n is at least 6,
(ii) each R is independently an H or an organic group, and
(iii) the compound has a degree of substitution of about 0.05 to about 3.0.
The aqueous composition prepared in this method comprises a cellulase.

In a tenth embodiment, the cellulase is (i) comprised in the aqueous composition prior to the contacting step, or (ii) added to the aqueous composition during or after the contacting step.

In an eleventh embodiment, (i) the viscosity of the aqueous composition is increased by the poly alpha-1,3-glucan ether compound, and/or (ii) the shear thinning behavior or the shear thickening behavior of the aqueous composition is increased by the poly alpha-1,3-glucan ether compound.

In a twelfth embodiment, the disclosure concerns a method of treating a material. This method comprises contacting a material with an aqueous composition comprising a cellulase and a poly alpha-1,3-glucan ether compound represented by the structure:

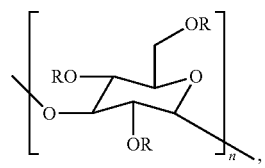

wherein
(i) n is at least 6,
(ii) each R is independently an H or an organic group, and (iii) the compound has a degree of substitution of about 0.05 to about 3.0. The poly alpha-1,3-glucan ether compound can adsorb to the surface of the material in certain embodiments of this method.

In a thirteenth embodiment, the material comprises fabric. The fabric comprises a (i) natural fiber, (ii) synthetic fiber, or a combination of both (i) and (ii), in a fourteenth embodiment. In a fifteenth embodiment, the poly alpha-1,3-glucan ether compound adsorbs to the fabric.

DETAILED DESCRIPTION OF INVENTION

The disclosures of all patent and non-patent literature cited herein are incorporated herein by reference in their entirety.

As used herein, the term "invention" or "disclosed invention" is not meant to be limiting, but applies generally to any of the inventions defined in the claims or described herein. These terms are used interchangeably herein.

The terms "cellulase" and "cellulase enzyme" are used interchangeably herein to refer to an enzyme that hydrolyzes beta-1,4-D-glucosidic linkages in cellulose, thereby partially or completely degrading cellulose. Cellulase can alternatively be referred to as "beta-1,4-glucanase", for example, and can have endocellulase activity (EC 3.2.1.4), exocellulase activity (EC 3.2.1.91), or cellobiase activity (EC 3.2.1.21). A cellulase in certain embodiments herein can also hydrolyze beta-1,4-D-glucosidic linkages in cellulose ether derivatives such as carboxymethyl cellulose. "Cellulose" refers to an insoluble polysaccharide having a linear chain of beta-1,4-linked D-glucose monomeric units.

The terms "fabric", "textile", "cloth" and the like are used interchangeably herein to refer to a woven material having a network of natural and/or artificial fibers. Such fibers can be thread or yarn, for example.

A "fabric care composition" herein is any composition suitable for treating fabric in some manner. Examples of such a composition include laundry detergents and fabric softeners.

The terms "heavy duty detergent", "all-purpose detergent" and the like are used interchangeably herein to refer to a detergent useful for regular washing of white and colored textiles at any temperature. The terms "low duty detergent", "fine fabric detergent" and the like are used interchangeably herein to refer to a detergent useful for the care of delicate fabrics such as viscose, wool, silk, microfiber or other fabric requiring special care. "Special care" can include conditions of using excess water, low agitation, and/or no bleach, for example.

A "detergent composition" herein typically comprises at least a surfactant (detergent compound) and/or a builder. A "surfactant" herein refers to a substance that tends to reduce the surface tension of a liquid in which the substance is dissolved. A surfactant may act as a detergent, wetting agent, emulsifier, foaming agent, and/or dispersant, for example.

The terms "anti-redeposition agent", "anti-soil redeposition agent", "anti-greying agent" and the like herein refer to agents that help keep soils from redepositing onto clothing in laundry wash water after these soils have been removed, therefore preventing greying/discoloration of laundry. Anti-redeposition agents can function by helping keep soil dispersed in wash water and/or by blocking attachment of soil onto fabric surfaces.

An "oral care composition" herein is any composition suitable for treating an soft or hard surface in the oral cavity such as dental (teeth) and/or gum surfaces.

The term "adsorption" herein refers to the adhesion of a compound (e.g., poly alpha-1,3-glucan ether) to the surface of a material.

The terms "poly alpha-1,3-glucan", "alpha-1,3-glucan polymer", "glucan polymer" and the like are used interchangeably herein. Poly alpha-1,3-glucan is a polymer comprising glucose monomeric units linked together by glycosidic linkages (i.e., glucosidic linkages), wherein at least about 50% of the glycosidic linkages are alpha-1,3-glycosidic linkages. Poly alpha-1,3-glucan is a type of polysaccharide. The term "alpha-1,3-glycosidic linkage" as used herein refers to the type of covalent bond that joins alpha-D-glucose molecules to each other through carbons 1 and 3 on adjacent alpha-D-glucose rings.

Poly alpha-1,3-glucan that can be used for preparing poly alpha-1,3-glucan ether compounds herein can be prepared using chemical methods. Alternatively, it can be prepared by extracting it from various organisms, such as fungi, that produce poly alpha-1,3-glucan. Alternatively still, poly alpha-1,3-glucan can be enzymatically produced from sucrose using one or more glucosyltransferase (gtf) enzymes (e.g., gtfJ), such as described in U.S. Pat. No. 7,000,000, and U.S. Patent Appl. Publ. Nos. 2013/0244288 and 2013/0244287 (all of which are incorporated herein by reference), for example.

The terms "glucosyltransferase enzyme", "gtf enzyme", "gtf", "glucansucrase" and the like are used interchangeably herein. The activity of a gtf enzyme herein catalyzes the reaction of the substrate sucrose to make the products poly alpha-1,3-glucan and fructose. Other products (byproducts) of a gtf reaction can include glucose (results from when glucose is hydrolyzed from the glucosyl-gtf enzyme intermediate complex), various soluble oligosaccharides (e.g., DP2-DP7), and leucrose (results from when glucose of the glucosyl-gtf enzyme intermediate complex is linked to fructose). Leucrose is a disaccharide composed of glucose and fructose linked by an alpha-1,5 linkage. Wild type forms of glucosyltransferase enzymes generally contain (in the N-terminal to C-terminal direction) a signal peptide, a variable domain, a catalytic domain, and a glucan-binding domain. A gtf herein is classified under the glycoside hydrolase family 70 (GH70) according to the CAZy (Carbohydrate-Active EnZymes) database (Cantarel et al., *Nucleic Acids Res.* 37:D233-238, 2009).

The terms "glycosidic linkage" and "glycosidic bond" are used interchangeably herein and refer to the type of covalent bond that joins a carbohydrate (sugar) molecule to another group such as another carbohydrate. The term "alpha-1,3-glycosidic linkage" as used herein refers to the type of covalent bond that joins alpha-D-glucose molecules to each other through carbons 1 and 3 on adjacent alpha-D-glucose rings.

"Alpha-D-glucose" herein can also be referred to as "glucose".

The terms "poly alpha-1,3-glucan ether compound", "poly alpha-1,3-glucan ether", "poly alpha-1,3-glucan ether derivative" and the like are used interchangeably herein. A poly alpha-1,3-glucan ether compound herein can be represented by the structure:

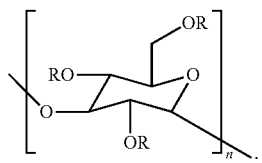

Regarding the formula of this structure, n can be at least 6, and each R can independently be a hydrogen atom (H) or an organic group. A poly alpha-1,3-glucan ether compound herein has a degree of substitution of about 0.05 to about 3.0. Poly alpha-1,3-glucan ether compounds disclosed in U.S. Appl. Publ. No. 2014/0179913 (incorporated herein by reference), and those disclosed herein, for example, can be used to prepare the compositions of the present disclosure.

A poly alpha-1,3-glucan ether compound is termed an "ether" herein by virtue of comprising the substructure —$C_G$—O—C—, where "—$C_G$—" represents carbon 2, 4, or 6 of a glucose monomeric unit of a poly alpha-1,3-glucan ether compound, and where "—C—" is comprised in the organic group.

Poly alpha-1,3-glucan ether compounds disclosed herein are synthetic, man-made compounds.

An "organic group" group as used herein refers to a chain of one or more carbons that (i) has the formula —$C_nH_{2n+1}$ (i.e., an alkyl group, which is completely saturated) or (ii) is mostly saturated but has one or more hydrogens substituted with another atom or functional group (i.e., a "substituted alkyl group"). Such substitution may be with one or more hydroxyl groups, oxygen atoms (thereby forming an aldehyde or ketone group), carboxyl groups, or other alkyl groups. In other words, where R is an organic group, R can be a chain of one or more saturated carbons, or a chain of carbons having one or more hydrogens substituted with a hydroxyl group, oxygen atom (thereby forming an aldehyde or ketone group), carboxyl group, or alkyl group. An organic group herein may be uncharged or anionic (an example of an anionic organic group is a carboxy alkyl group).

A "hydroxy alkyl" group herein refers to a substituted alkyl group in which one or more hydrogen atoms of the alkyl group are substituted with a hydroxyl group. A "carboxy alkyl" group herein refers to a substituted alkyl group in which one or more hydrogen atoms of the alkyl group are substituted with a carboxyl group.

A "halide" herein refers to a compound comprising one or more halogen atoms (e.g., fluorine, chlorine, bromine, iodine). A halide herein can refer to a compound comprising one or more halide groups such as fluoride, chloride, bromide, or iodide. A halide group may serve as a reactive group of an etherification agent.

An "etherification reaction" herein refers to a reaction comprising at least poly alpha-1,3-glucan and an etherification agent. These components are typically dissolved and/or mixed in an aqueous alkali hydroxide. A reaction is placed under suitable conditions (e.g., time, temperature) for the etherification agent to etherify one or more hydroxyl groups of the glucose units of poly alpha-1,3-glucan with an organic group, thereby yielding a poly alpha-1,3-glucan ether compound.

The term "alkaline conditions" herein refers to a solution or mixture pH of at least 11 or 12. Alkaline conditions can be prepared by any means known in the art, such as by dissolving an alkali hydroxide in a solution or mixture.

The terms "etherification agent" and "alkylation agent" are used interchangeably herein. An etherification agent herein refers to an agent that can be used to etherify one or more hydroxyl groups of one or more glucose units of poly alpha-1,3-glucan with an organic group. An etherification agent thus comprises an organic group.

The term "poly alpha-1,3-glucan slurry" herein refers to an aqueous mixture comprising the components of a glucosyltransferase enzymatic reaction such as poly alpha-1,3-glucan, sucrose, one or more glucosyltransferase enzymes, glucose and fructose. This composition is a slurry since the poly alpha-1,3-glucan is not dissolved therein.

The term "poly alpha-1,3-glucan wet cake" herein refers to poly alpha-1,3-glucan that has been separated from a slurry and washed with water or an aqueous solution. Poly alpha-1,3-glucan is not completely dried when preparing a wet cake.

The term "degree of substitution" (DoS) as used herein refers to the average number of hydroxyl groups substituted in each monomeric unit (glucose) of a poly alpha-1,3-glucan ether compound. Since there are three hydroxyl groups in each monomeric unit in poly alpha-1,3-glucan, the degree of substitution in a poly alpha-1,3-glucan ether compound herein can be no higher than 3.

The term "molar substitution" (M.S.) as used herein refers to the moles of an organic group per monomeric unit of a poly alpha-1,3-glucan ether compound. Alternatively, M.S. can refer to the average moles of etherification agent used to react with each monomeric unit in poly alpha-1,3-glucan (M.S. can thus describe the degree of derivatization of an etherification agent). It is noted that the M.S. value for poly alpha-1,3-glucan may have no upper limit. For example, when an organic group containing a hydroxyl group (e.g., hydroxyethyl or hydroxypropyl) has been etherified to poly alpha-1,3-glucan, the hydroxyl group of the organic group may undergo further reaction, thereby coupling more of the organic group to the poly alpha-1,3-glucan.

The term "crosslink" herein refers to a chemical bond, atom, or group of atoms that connects two adjacent atoms in one or more polymer molecules. It should be understood that, in a composition comprising crosslinked poly alpha-1,3-glucan ether, crosslinks can be between at least two poly alpha-1,3-glucan ether molecules (i.e., intermolecular crosslinks); there can also be intramolecular crosslinking. A "crosslinking agent" as used herein is an atom or compound that can create crosslinks.

An "aqueous composition" herein has a liquid component that comprises at least about 10 wt % water, for example. Examples of aqueous compositions include mixtures, solutions, dispersions (e.g., colloidal dispersions), suspensions and emulsions, for example. Aqueous compositions in certain embodiments comprise one or more poly alpha-1,3-glucan ether compounds that are (i) dissolved in the aqueous composition (i.e., in solution), or (ii) not dissolved in the aqueous composition (e.g., present as a colloidal dispersion).

As used herein, the term "colloidal dispersion" refers to a heterogeneous system having a dispersed phase and a dispersion medium, i.e., microscopically dispersed insoluble particles (e.g., some forms of poly alpha-1,3-glucan ether herein) are suspended throughout another substance (e.g., an aqueous composition such as water or aqueous solution). An example of a colloidal dispersion herein is a hydrocolloid. All, or a portion of, the particles of a colloidal dispersion such as a hydrocolloid can comprise certain poly alpha-1,3-glucan ether compounds of the present disclosure. The terms "dispersant" and "dispersion agent" are used interchangeably herein to refer to a material that promotes the formation and/or stabilization of a dispersion.

The terms "hydrocolloid" and "hydrogel" are used interchangeably herein. A hydrocolloid refers to a colloid system in which water or an aqueous solution is the dispersion medium.

The term "aqueous solution" herein refers to a solution in which the solvent comprises water. An aqueous solution can serve as a dispersant in certain aspects herein.

The term "viscosity" as used herein refers to the measure of the extent to which a fluid or an aqueous composition resists a force tending to cause it to flow. Various units of viscosity that can be used herein include centipoise (cPs) and Pascal-second (Pa·s). One poise is equal to 0.100 kg·m$^{-1}$·s$^{-1}$, or 1 mPa·s. Thus, the terms "viscosity modifier" and "viscosity-modifying agent" as used herein refer to anything that can alter/modify the viscosity of a fluid or aqueous composition.

The term "shear thinning behavior" as used herein refers to a decrease in the viscosity of the hydrocolloid or aqueous solution as shear rate increases. The term "shear thickening behavior" as used herein refers to an increase in the viscosity of the hydrocolloid or aqueous solution as shear rate increases. "Shear rate" herein refers to the rate at which a progressive shearing deformation is applied to the hydrocolloid or aqueous solution. A shearing deformation can be applied rotationally.

The term "contacting" as used herein, such as with contacting poly alpha-1,3-glucan, a poly alpha-1,3-glucan ether compound, and/or cellulase with an aqueous composition, can be performed by any means known in the art, such as dissolving, mixing, shaking, or homogenization, for example.

The "molecular weight" of poly alpha-1,3-glucan and poly alpha-1,3-glucan ether compounds herein can be represented as number-average molecular weight ($M_n$) or as weight-average molecular weight ($M_w$). Alternatively, molecular weight can be represented as Daltons, grams/mole, DPw (weight average degree of polymerization), or DPn (number average degree of polymerization). Various means are known in the art for calculating these molecular weight measurements, such as high-pressure liquid chromatography (HPLC), size exclusion chromatography (SEC), or gel permeation chromatography (GPC).

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture or solution.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein.

Development of new polysaccharide polymers that provide the benefits of cellulosic polymers, but that are resistant to cellulase, is desirable. Poly alpha-1,3-glucan ether compounds are disclosed herein as a superior alternative to cellulosic polymers, since they are stable (resistant) to cellulase and have other features useful in formulations such as detergents.

Embodiments of the present disclosure concern a composition comprising a cellulase and a poly alpha-1,3-glucan ether compound represented by the structure:

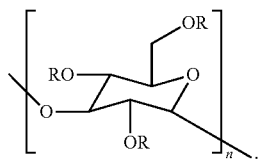

Regarding the formula of this structure, n can be at least 6, and each R can independently be an H or an organic group. Furthermore, the poly alpha-1,3-glucan ether compound has a degree of substitution with the organic group of about 0.05 to about 3.0.

Significantly, a poly alpha-1,3-glucan ether compound of the disclosure can modify the viscosity and rheological properties of an aqueous solution to which it is added, and also adsorb to surfaces such as a fabric surface. Furthermore, since poly alpha-1,3-glucan ether compounds herein are stable to cellulase activity, one or more cellulase enzymes can be included in a composition comprising the glucan ether compound. Thus, a composition herein can optionally be characterized as one for which including a cellulase is beneficial to the utility of the composition.

One or more cellulase enzymes are comprised in the disclosed composition. A cellulase herein can have endocellulase activity (EC 3.2.1.4), exocellulase activity (EC 3.2.1.91), or cellobiase activity (EC 3.2.1.21). A cellulase herein is an "active cellulase" having activity under suitable conditions for maintaining cellulase activity; it is within the skill of the art to determine such suitable conditions. Besides being able to degrade cellulose, a cellulase in certain embodiments can also degrade cellulose ether derivatives such as carboxymethyl cellulose. Examples of cellulose ether derivatives which are expected to not be stable to cellulase are disclosed in U.S. Pat. Nos. 7,012,053, 7,056,880, 6,579,840, 7,534,759 and 7,576,048.

A cellulase herein may be derived from any microbial source, such as a bacteria or fungus. Chemically-modified cellulases or protein-engineered mutant cellulases are included. Suitable cellulases include, but are not limited to, cellulases from the genera *Bacillus*, *Pseudomonas*, *Streptomyces*, *Trichoderma*, *Humicola*, *Fusarium*, *Thielavia* and *Acremonium*. As other examples, a cellulase may be derived from *Humicola insolens*, *Myceliophthora thermophila* or *Fusarium oxysporum*; these and other cellulases are disclosed in U.S. Pat. Nos. 4,435,307, 5,648,263, 5,691,178, 5,776,757 and 7,604,974, which are all incorporated herein by reference. Exemplary *Trichoderma reesei* cellulases are disclosed in U.S. Pat. Nos. 4,689,297, 5,814,501, 5,324,649, and International Patent Appl. Publ. Nos. WO92/06221 and WO92/06165, all of which are incorporated herein by reference. Exemplary *Bacillus* cellulases are disclosed in U.S. Pat. No. 6,562,612, which is incorporated herein by reference. A cellulase, such as any of the foregoing, preferably is in a mature form lacking an N-terminal signal peptide. Commercially available cellulases useful herein include CELLUZYME® and CAREZYME® (Novozymes A/S); CLAZINASE® and PURADAX® HA (DuPont Industrial Biosciences), and KAC-500(B)®(Kao Corporation).

Alternatively, a cellulase herein may be produced by any means known in the art, such as described in U.S. Pat. Nos. 4,435,307, 5,776,757 and 7,604,974, which are incorporated herein by reference. For example, a cellulase may be produced recombinantly in a heterologous expression system, such as a microbial or fungal heterologous expression system. Examples of heterologous expression systems include bacterial (e.g., *E. coli, Bacillus* sp.) and eukaryotic systems. Eukaryotic systems can employ yeast (e.g., *Pichia* sp., *Saccharomyces* sp.) or fungal (e.g., *Trichoderma* sp. such as *T. reesei, Aspergillus* species such as *A. niger*) expression systems, for example.

One or more cellulases can be directly added as an ingredient when preparing the disclosed composition. Alternatively, one or more cellulases can be indirectly (inadvertently) provided in the disclosed composition. For example, cellulase can be provided in a composition herein by virtue of being present in a non-cellulase enzyme preparation used for preparing the composition. Cellulase in compositions in which cellulase is indirectly provided thereto can be present at about 0.1-10 ppb (e.g., less than 1 ppm), for example. A benefit of a composition herein, by virtue of employing a poly alpha-1,3-glucan ether compound instead of a cellulose ether compound, is that non-cellulase enzyme preparations that might have background cellulase activity can be used without concern that the desired effects of the glucan ether will be negated by the background cellulase activity.

A cellulase in certain embodiments can be thermostable. Cellulase thermostability refers to the ability of the enzyme to retain activity after exposure to an elevated temperature (e.g. about 60-70° C.) for a period of time (e.g., about 30-60 minutes). The thermostability of a cellulase can be measured by its half-life (t½) given in minutes, hours, or days, during which time period half the cellulase activity is lost under defined conditions.

A cellulase in certain embodiments can be stable to a wide range of pH values (e.g. neutral or alkaline pH such as pH of ~7.0 to ~11.0). Such enzymes can remain stable for a predetermined period of time (e.g., at least about 15 min., 30 min., or 1 hour) under such pH conditions.

At least one, two, or more cellulases may be included in the composition. The total amount of cellulase in a composition herein typically is an amount that is suitable for the purpose of using cellulase in the composition (an "effective amount"). For example, an effective amount of cellulase in a composition intended for improving the feel and/or appearance of a cellulose-containing fabric is an amount that produces measurable improvements in the feel of the fabric (e.g., improving fabric smoothness and/or appearance, removing pills and fibrils which tend to reduce fabric appearance sharpness). As another example, an effective amount of cellulase in a fabric stonewashing composition herein is that amount which will provide the desired effect (e.g., to produce a worn and faded look in seams and on fabric panels). The amount of cellulase in a composition herein can also depend on the process parameters in which the composition is employed (e.g., equipment, temperature, time, and the like) and cellulase activity, for example. The effective concentration of cellulase in an aqueous composition in which a fabric is treated can be readily determined by a skilled artisan. In fabric care processes, cellulase can be present in an aqueous composition (e.g., wash liquor) in which a fabric is treated in a concentration that is minimally about 0.01-0.1 ppm total cellulase protein, or about 0.1-10 ppb total cellulase protein (e.g., less than 1 ppm), to maximally about 100, 200, 500, 1000, 2000, 3000, 4000, or 5000 ppm total cellulase protein, for example.

Poly alpha-1,3 glucan and/or poly alpha-1,3-glucan ethers herein are mostly or completely stable (resistant) to being degraded by cellulase. For example, the percent degradation of a poly alpha-1,3 glucan and/or poly alpha-1,3-glucan ether compound by one or more cellulases is less than 10%, 9%, 8%, 7%, 6%, 5%, 4%, 3%, 2%, or 1%, or is 0%. Such percent degradation can be determined, for example, by comparing the molecular weight of polymer before and after treatment with a cellulase for a period of time (e.g., ~24 hours).

The degree of substitution (DoS) of a poly alpha-1,3-glucan ether compound in a composition disclosed herein is about 0.5 to about 3.0. Alternatively, the DoS can be about 0.2 to about 2.0. Alternatively still, the DoS can be at least about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0. It would be understood by those skilled in the art that since a poly alpha-1,3-glucan ether compound herein has a degree of substitution between about 0.05 to about 3.0, and by virtue of being an ether, the R groups of the compound cannot only be hydrogen.

The DoS of a poly alpha-1,3-glucan ether compound herein can affect the viscosity of an aqueous composition in which it may be comprised. For example, an aqueous composition herein comprising carboxymethyl poly alpha-1,3-glucan (CMG) with a DoS of about 0.4-0.6 is believed to have a greater viscosity than an aqueous composition comprising CMG with higher DoS (e.g., about 0.8-1.0).

The percentage of glycosidic linkages between the glucose monomeric units of poly alpha-1,3-glucan ether compounds herein that are alpha-1,3 is at least about 50%, 60%, 70%, 80%, 90%, 95%, 96%, 97%, 98%, 99%, or 100% (or any integer between 50% and 100%. In such embodiments, accordingly, the compound has less than about 50%, 40%, 30%, 20%, 10%, 5%, 4%, 3%, 2%, 1%, or 0% (or any integer value between 0% and 50%) of glycosidic linkages that are not alpha-1,3.

The backbone of a poly alpha-1,3-glucan ether compound herein is preferably linear/unbranched. In certain embodiments, the compound has no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points.

The formula of a poly alpha-1,3-glucan ether compound comprised in a composition herein has an n value of at least 6. Alternatively, n can have a value of at least 25, 50, 75, 100, 150, 200, 250, 300, 350, 400, 450, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000 (or any integer between 25 and 4000), for example. The value of n in still other examples can be in a range of 25-250, 50-250, 75-250, 100-250, 150-250, 200-250, 25-200, 50-200, 75-200, 100-200, 150-200, 25-150, 50-150, 75-150, 100-150, 25-100, 50-100, 75-100, 25-75, 50-75, or 25-50.

The molecular weight of a poly alpha-1,3-glucan ether compound herein can be measured as number-average molecular weight ($M_n$) or as weight-average molecular weight ($M_w$). Alternatively, molecular weight can be measured in Daltons or grams/mole. It may also be useful to refer to the $DP_w$ (weight average degree of polymerization) or $DP_n$ (number average degree of polymerization) of the poly alpha-1,3-glucan polymer component of the compound.

The $M_n$ or $M_w$ of poly alpha-1,3-glucan ether compounds herein may be at least about 1000. Alternatively, the $M_n$ or $M_w$ can be at least about 1000 to about 600000. Alternatively still, the $M_n$ or $M_w$ can be at least about 2000, 3000, 4000, 5000, 6000, 7000, 8000, 9000, 10000, 15000, 20000, 25000, 30000, 35000, 40000, 45000, 50000, 75000, 100000, 150000, 200000, 250000, 300000, 350000, 400000, 450000, 500000, 550000, or 600000 (or any integer between 2000 and 600000), for example.

Each R group in the formula of a poly alpha-1,3-glucan ether compound herein can independently be an H or an organic group. An organic group may be an alkyl group such as a methyl, ethyl, propyl, butyl, pentyl, hexyl, heptyl, octyl, nonyl, or decyl group, for example.

Alternatively, an organic group may be a substituted alkyl group in which there is a substitution on one or more carbons of the alkyl group. The substitution(s) may be one or more hydroxyl, aldehyde, ketone, and/or carboxyl groups. For example, a substituted alkyl group may be a hydroxy alkyl group, dihydroxy alkyl group, or carboxy alkyl group.

Examples of suitable hydroxy alkyl groups are hydroxymethyl (—CH$_2$OH), hydroxyethyl (e.g., —CH$_2$CH$_2$OH, —CH(OH)CH$_3$), hydroxypropyl (e.g., —CH$_2$CH$_2$CH$_2$OH, —CH$_2$CH(OH)CH$_3$, —CH(OH)CH$_2$CH$_3$), hydroxybutyl and hydroxypentyl groups. Other examples include dihydroxy alkyl groups (diols) such as dihydroxymethyl, dihydroxyethyl (e.g., —CH(OH)CH$_2$OH), dihydroxypropyl (e.g., —CH$_2$CH(OH)CH$_2$OH, —CH(OH)CH(OH)CH$_3$), dihydroxybutyl and dihydroxypentyl groups.

Examples of suitable carboxy alkyl groups are carboxymethyl (—CH$_2$COOH), carboxyethyl (e.g., —CH$_2$CH$_2$COOH, —CH(COOH)CH$_3$), carboxypropyl (e.g., —CH$_2$CH$_2$CH$_2$COOH, —CH$_2$CH(COOH)CH$_3$, —CH(COOH)CH$_2$CH$_3$), carboxybutyl and carboxypentyl groups.

Alternatively still, one or more carbons of an alkyl group can have a substitution(s) with another alkyl group. Examples of such substituent alkyl groups are methyl, ethyl and propyl groups. To illustrate, an R group can be —CH(CH$_3$)CH$_2$CH$_3$ or —CH$_2$CH(CH$_3$)CH$_3$, for example, which are both propyl groups having a methyl substitution.

As should be clear from the above examples of various substituted alkyl groups, a substitution (e.g., hydroxy or carboxy group) on an alkyl group in certain embodiments may be bonded to the terminal carbon atom of the alkyl group, where the terminal carbon group is opposite the terminus that is in ether linkage to the glucose group in the glucan ether compound (above formula). An example of this terminal substitution is in the hydroxypropyl group —CH$_2$CH$_2$CH$_2$OH. Alternatively, a substitution may be on an internal carbon atom of an alkyl group. An example on an internal substitution is in the hydroxypropyl group —CH$_2$CH(OH)CH$_3$. An alkyl group can have one or more substitutions, which may be the same (e.g., two hydroxyl groups [dihydroxy]) or different (e.g., a hydroxyl group and a carboxyl group).

Poly alpha-1,3-glucan ether compounds in certain embodiments disclosed herein may contain one type of organic group. For example, one or more R groups ether-linked to the glucose group in the above formula may be a methyl group; the R groups in this particular example would thus independently be hydrogen and methyl groups. Such a compound can be referred to as ethyl poly alpha-1,3-glucan. As another example, one or more R groups ether-linked to the glucose group in the above formula may be a carboxymethyl group; the R groups in this particular example would thus independently be hydrogen and carboxymethyl groups. Such a compound can be referred to as carboxymethyl poly alpha-1,3-glucan (CMG).

Alternatively, poly alpha-1,3-glucan ether compounds comprised in a composition herein can contain two or more different types of organic groups. Examples of such compounds contain (i) two different alkyl groups as R groups, (ii) an alkyl group and a hydroxy alkyl group as R groups (alkyl hydroxyalkyl poly alpha-1,3-glucan, generically speaking), (iii) an alkyl group and a carboxy alkyl group as R groups (alkyl carboxyalkyl poly alpha-1,3-glucan, generically speaking), (iv) a hydroxy alkyl group and a carboxy alkyl group as R groups (hydroxyalkyl carboxyalkyl poly alpha-1,3-glucan, generically speaking), (v) two different hydroxy alkyl groups as R groups, or (vi) two different carboxy alkyl groups as R groups. Specific non-limiting examples of such compounds include ethyl hydroxyethyl poly alpha-1,3-glucan (i.e., where R groups are independently H, ethyl, or hydroxyethyl), hydroxyalkyl methyl poly alpha-1,3-glucan (i.e., where R groups are independently H, hydroxyalkyl, or methyl), carboxymethyl hydroxyethyl poly alpha-1,3-glucan (i.e., where R groups are independently H, carboxymethyl, or hydroxyethyl), and carboxymethyl hydroxypropyl poly alpha-1,3-glucan (i.e., where R groups are independently H, carboxymethyl, or hydroxypropyl).

Poly alpha-1,3-glucan ether compounds herein can comprise at least one nonionic organic group and at least one anionic group, for example. As another example, poly alpha-1,3-glucan ether compounds herein can comprise at least one nonionic organic group and at least one positively charged organic group.

A composition comprising (i) cellulase and (ii) poly alpha-1,3-glucan and/or a poly alpha-1,3-glucan ether compound in certain embodiments can be non-aqueous (e.g., a dry composition). Examples of such embodiments include powders, granules, microcapsules, flakes, or any other form of particulate matter. Other examples include larger compositions such as pellets, bars, kernels, beads, tablets, sticks, or other agglomerates. A non-aqueous or dry composition herein typically has less than 3, 2, 1, 0.5, or 0.1 wt % water comprised therein. A non-aqueous composition herein can comprise about 0.0001 wt % to about 2.0 wt % one or more cellulases, for example. Methods for preparing dry compositions comprising active enzymes such as cellulases are well known in the art.

A composition comprising a cellulase and a poly alpha-1,3-glucan ether compound in certain embodiments is an aqueous composition. An aqueous composition herein is a solution or mixture in which the solvent is at least about 10 wt % water. In other embodiments, the solvent in an aqueous composition is at least about 20, 30, 40, 50, 60, 70, 80, 90, or 100 wt % water (or any integer value between 10 and 100 wt %). Examples of aqueous compositions herein are aqueous solutions, mixtures and hydrocolloids.

An aqueous composition comprising a cellulase and a poly alpha-1,3-glucan ether compound has a viscosity of at least about 10 cPs in certain embodiments. Alternatively, an aqueous composition herein has a viscosity of at least about 100, 250, 500, 750, 1000, 1500, 2000, 2500, 3000, 3500, 4000, 4500, 5000, 5500, 6000, 6500, 7000, 7500, 8000, 8500, 9000, 9500, 10000, 10500, 11000, 12000, 13000, 14000, 15000, 20000, 30000, 40000, 50000, 60000, 70000, 80000, 90000, or 100000 cPs (or any integer between 100 and 100000 cPs), for example.

Viscosity can be measured for an aqueous composition herein at any temperature between about 3° C. to about 110° C. (or any integer between 3 and 110° C.), for example. Alternatively, viscosity can be measured at a temperature between about 4° C. to 30° C., or about 20° C. to 25° C. Viscosity can be measured at atmospheric pressure (about 760 torr) or any other higher or lower pressure.

The viscosity of an aqueous composition disclosed herein can be measured using a viscometer or rheometer, or using any other means known in the art. It would be understood by those skilled in the art that a rheometer can be used to measure the viscosity of those aqueous compositions of the disclosure that exhibit shear thinning behavior or shear thickening behavior (i.e., liquids with viscosities that vary with flow conditions). The viscosity of such embodiments can be measured at a rotational shear rate of about 10 to 1000 rpm (revolutions per minute) (or any integer between 10 and 1000 rpm), for example. Alternatively, viscosity can be measured at a rotational shear rate of about 10, 60, 150, 250, or 600 rpm.

The pH of an aqueous composition disclosed herein can be between about 2.0 to about 12.0. Alternatively, pH can be about 2.0, 3.0, 4.0, 5.0, 6.0, 7.0, 8.0, 9.0, 10.0, 11.0, 12.0; or between 5.0 to about 12.0; or between about 4.0 to about 8.0; or between about 3.0 and 11.0. A skilled artisan would be able to select and provide a pH or pH range that is suitable for maintaining cellulase activity in an aqueous composition herein. In certain embodiments, the viscosity of the disclosed aqueous composition does not largely fluctuate at a pH between about 3.0 and 11.0.

A poly alpha-1,3-glucan ether compound can be present in a composition herein, such as an aqueous composition, at a wt % of about, or at least about, 0.01, 0.05, 0.1, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 wt %, for example.

Compositions in certain embodiments herein may comprise a cellulose ether compound (e.g., carboxymethyl cellulose [CMC]), whereas there is no cellulose ether compound (e.g., CMC) in other embodiments. It is preferable that a cellulose ether compound is absent, as it would be subject to degradation by one or more cellulase enzymes present in the disclosed composition.

A composition herein, such as an aqueous composition, can comprise other components in addition to cellulase and one or more poly alpha-1,3-glucan ether compounds. For example, the composition can comprise one or more salts such as a sodium salts (e.g., NaCl, $Na_2SO_4$). Other non-limiting examples of salts include those having (i) an aluminum, ammonium, barium, calcium, chromium (II or III), copper (I or II), iron (II or III), hydrogen, lead (II), lithium, magnesium, manganese (II or III), mercury (I or II), potassium, silver, sodium strontium, tin (II or IV), or zinc cation, and (ii) an acetate, borate, bromate, bromide, carbonate, chlorate, chloride, chlorite, chromate, cyanamide, cyanide, dichromate, dihydrogen phosphate, ferricyanide, ferrocyanide, fluoride, hydrogen carbonate, hydrogen phosphate, hydrogen sulfate, hydrogen sulfide, hydrogen sulfite, hydride, hydroxide, hypochlorite, iodate, iodide, nitrate, nitride, nitrite, oxalate, oxide, perchlorate, permanganate, peroxide, phosphate, phosphide, phosphite, silicate, stannate, stannite, sulfate, sulfide, sulfite, tartrate, or thiocyanate anion. Thus, any salt having a cation from (i) above and an anion from (ii) above can be in a composition comprising cellulase and a poly alpha-1,3-glucan ether compound, for example. A salt can be present in a composition herein at a wt % of about 0.01% to about 10.00% (or any hundredth increment between 0.01% and 10.00%), for example. One skilled in the art would be able to determine those salts that can be used in combination with a cellulase such that it maintains enzymatic activity.

Those skilled in the art would understand that in certain embodiments of the present disclosure, a poly alpha-1,3-glucan ether compound can be in an anionic form when provided in an aqueous composition. Examples may include those poly alpha-1,3-glucan ether compounds having an organic group comprising an alkyl group substituted with a carboxyl group. Carboxyl (COOH) groups in a carboxyalkyl poly alpha-1,3-glucan ether compound can convert to carboxylate ($COO^-$) groups in aqueous conditions. Such anionic groups can interact with salt cations such as any of those listed above in (i) (e.g., potassium, sodium, or lithium cation). Thus, a poly alpha-1,3-glucan ether compound can be a sodium carboxyalkyl poly alpha-1,3-glucan ether (e.g., sodium carboxymethyl poly alpha-1,3-glucan), potassium carboxyalkyl poly alpha-1,3-glucan ether (e.g., potassium carboxymethyl poly alpha-1,3-glucan), or lithium carboxyalkyl poly alpha-1,3-glucan ether (e.g., lithium carboxymethyl poly alpha-1,3-glucan), for example.

A poly alpha-1,3-glucan ether compound comprised in certain embodiments of the disclosed composition may be crosslinked using any means known in the art. Such crosslinks may be borate crosslinks, where the borate is from any boron-containing compound (e.g., boric acid, diborates, tetraborates, pentaborates, polymeric compounds such as Polybor®, polymeric compounds of boric acid, alkali borates), for example. Alternatively, crosslinks can be provided with polyvalent metals such as titanium or zirconium, for example. Titanium crosslinks may be provided, for example, using titanium IV-containing compounds such as titanium ammonium lactate, titanium triethanolamine, titanium acetylacetonate, and polyhydroxy complexes of titanium. Zirconium crosslinks can be provided using zirconium IV-containing compounds such as zirconium lactate, zirconium carbonate, zirconium acetylacetonate, zirconium triethanolamine, zirconium diisopropylamine lactate and polyhydroxy complexes of zirconium, for example. Alternatively still, crosslinks can be provided with any crosslinking agent described in U.S. Pat. Nos. 4,462,917, 4,464,270, 4,477,360 and 4,799,550, which are all incorporated herein by reference. A crosslinking agent (e.g., borate) may be present in a composition herein at a wt % of about 0.2 to 20 wt %, or about 0.1, 0.2, 0.3, 0.4, 0.5, 1, 2, 3, 4, 5, 6, 7, 8, 9, 10, 15, or 20 wt %, for example.

A poly alpha-1,3-glucan ether compound disclosed herein that is crosslinked typically has a higher viscosity in an aqueous composition compared to its non-crosslinked counterpart. In addition, a crosslinked poly alpha-1,3-glucan ether compound can have increased shear thickening behavior compared to its non-crosslinked counterpart. For example, a borate-crosslinked hydroxyalkyl poly alpha-1,3-glucan ether compound (e.g., dihydroxypropyl glucan ether) can have increased shear thickening behavior compared to its non-crosslinked counterpart.

A composition herein may contain one or more different active enzymes in addition to at least one cellulase. Non-limiting examples of such other enzymes include proteases, hemicellulases, peroxidases, lipolytic enzymes (e.g., metallolipolytic enzymes), xylanases, lipases, phospholipases, esterases (e.g., arylesterase, polyesterase), perhydrolases, cutinases, pectinases, pectate lyases, mannanases, keratinases, reductases, oxidases (e.g., choline oxidase), phenoloxidases, lipoxygenases, ligninases, pullulanases, tannases, pentosanases, malanases, beta-glucanases, arabinosidases, hyaluronidases, chondroitinases, laccases, metalloproteinases, amadoriases, glucoamylases, arabinofuranosidases, phytases, isomerases, transferases and amylases. Cellulase and optionally one or more additional enzymes may each be comprised in a composition herein at about 0.0001-0.1 wt % (e.g., 0.01-0.03 wt %) active enzyme (e.g., calculated as pure enzyme protein), for example.

The Examples disclosed herein demonstrate that aqueous compositions comprising a poly alpha-1,3-glucan ether compound herein can have shear thinning behavior or shear thickening behavior. It is expected that such aqueous compositions, which additionally comprise one or more cellulases, also have these rheological properties. Shear thinning behavior is observed as a decrease in viscosity of the aqueous composition as shear rate increases, whereas shear thickening behavior is observed as an increase in viscosity of the aqueous composition as shear rate increases. Modification of the shear thinning behavior or shear thickening behavior of an aqueous solution herein is due to the admixture of a poly alpha-1,3-glucan ether composition to the aqueous composition. Thus, one or more poly alpha-1,3-glucan ether compounds of the disclosure can be added to an aqueous composition to modify its rheological profile (i.e., the flow properties of the aqueous composition are modified). Also, one or more poly alpha-1,3-glucan ether compounds can be added to an aqueous composition to modify its viscosity.

The rheological properties of aqueous compositions herein can be observed by measuring viscosity over an increasing rotational shear rate (e.g., from about 10 rpm to about 250 rpm). For example, shear thinning behavior of an aqueous composition disclosed herein can be observed as a decrease in viscosity (cPs) by at least about 5%, 10%, 15%, 20%, 25%, 30%, 35%, 40%, 45%, 50%, 55%, 60%, 65%, 70%, 75%, 80%, 85%, 90%, or 95% (or any integer between 5% and 95%) as the rotational shear rate increases from about 10 rpm to 60 rpm, 10 rpm to 150 rpm, 10 rpm to 250 rpm, 60 rpm to 150 rpm, 60 rpm to 250 rpm, or 150 rpm to 250 rpm. As another example, shear thickening behavior of an aqueous composition disclosed herein can be observed as an increase in viscosity (cPs) by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, or 200% (or any integer between 5% and 200%) as the rotational shear rate increases from about 10 rpm to 60 rpm, 10 rpm to 150 rpm, 10 rpm to 250 rpm, 60 rpm to 150 rpm, 60 rpm to 250 rpm, or 150 rpm to 250 rpm.

A composition disclosed herein, such as an aqueous composition, can be in the form of a personal care product, pharmaceutical product, household product, or industrial product in which having one or more cellulase enzymes optionally increases the effectiveness of the product. Poly alpha-1,3-glucan and/or poly alpha-1,3-glucan ether compounds herein can be used as thickening agents and/or dispersion agents in each of these products, if desired, when in an aqueous form. Such a thickening agent may optionally be used in conjunction with one or more other types of thickening agents, such as those disclosed in U.S. Pat. No. 8,541,041, the disclosure of which is incorporated herein by reference.

Personal care products herein are not particularly limited and include, for example, skin care compositions, cosmetic compositions, antifungal compositions, and antibacterial compositions. Personal care products herein may be in the form of, for example, lotions, creams, pastes, balms, ointments, pomades, gels, liquids, combinations of these and the like. The personal care products disclosed herein can include at least one active ingredient, if desired. An active ingredient is generally recognized as an ingredient that causes an intended pharmacological effect.

In certain embodiments, a skin care product can include at least one active ingredient for the treatment or prevention of skin ailments, providing a cosmetic effect, or for providing a moisturizing benefit to skin, such as zinc oxide, petrolatum, white petrolatum, mineral oil, cod liver oil, lanolin, dimethicone, hard fat, vitamin A, allantoin, calamine, kaolin, glycerin, or colloidal oatmeal, and combinations of these. A skin care product may include one or more natural moisturizing factors such as ceramides, hyaluronic acid, glycerin, squalane, amino acids, cholesterol, fatty acids, triglycerides, phospholipids, glycosphingolipids, urea, linoleic acid, glycosaminoglycans, mucopolysaccharide, sodium lactate, or sodium pyrrolidone carboxylate, for example. Other ingredients that may be included in a skin care product include, without limitation, glycerides, apricot kernel oil, canola oil, squalane, squalene, coconut oil, corn oil, jojoba oil, jojoba wax, lecithin, olive oil, safflower oil, sesame oil, shea butter, soybean oil, sweet almond oil, sunflower oil, tea tree oil, shea butter, palm oil, cholesterol, cholesterol esters, wax esters, fatty acids, and orange oil.

A personal care product herein can also be in the form of makeup, lipstick, mascara, rouge, foundation, blush, eyeliner, lip liner, lip gloss, other cosmetics, sunscreen, sun block, nail polish, mousse, hair spray, styling gel, nail conditioner, bath gel, shower gel, body wash, face wash, shampoo, hair conditioner (leave-in or rinse-out), cream rinse, hair dye, hair coloring product, hair shine product, hair serum, hair anti-frizz product, hair split-end repair product, lip balm, skin conditioner, cold cream, moisturizer, body spray, soap, body scrub, exfoliant, astringent, scruffing lotion, depilatory, permanent waving solution, antidandruff formulation, antiperspirant composition, deodorant, shaving product, pre-shaving product, after-shaving product, cleanser, skin gel, rinse, dentifrice composition, toothpaste, or mouthwash, for example.

A pharmaceutical product herein can be in the form of an emulsion, liquid, elixir, gel, suspension, solution, cream, or ointment, for example. Also, a pharmaceutical product herein can be in the form of any of the personal care products disclosed herein, such as an antibacterial or antifungal composition. A pharmaceutical product can further comprise one or more pharmaceutically acceptable carriers, diluents, and/or pharmaceutically acceptable salts. A poly alpha-1,3-glucan ether compound disclosed herein can also be used in capsules, encapsulants, tablet coatings, and as an excipients for medicaments and drugs.

A household and/or industrial product herein can be in the form of drywall tape-joint compounds; mortars; grouts; cement plasters; spray plasters; cement stucco; adhesives; pastes; wall/ceiling texturizers; binders and processing aids for tape casting, extrusion forming, injection molding and ceramics; spray adherents and suspending/dispersing aids for pesticides, herbicides, and fertilizers; fabric care products such as fabric softeners and laundry detergents; hard surface cleaners; air fresheners; polymer emulsions; gels such as water-based gels; surfactant solutions; paints such as water-based paints; protective coatings; adhesives; sealants and caulks; inks such as water-based ink; hydraulic fluids (e.g., those used for fracking in downhole operations); and aqueous mineral slurries, for example.

Poly alpha-1,3-glucan and/or a poly alpha-1,3-glucan ether compound disclosed herein can be comprised in a personal care product, pharmaceutical product, household product, or industrial product in an amount that provides a desired degree of thickening or dispersion, for example. Examples of a concentration or amount of a poly alpha-1, 3-glucan ether compound in a product, on a weight basis, can be about 0.1-3 wt %, 1-2 wt %, 1.5-2.5 wt %, 2.0 wt %, 0.1-4 wt %, 0.1-5 wt %, or 0.1-10 wt %.

Compositions disclosed herein can be in the form of a fabric care composition. A fabric care composition herein can be used for hand wash, machine wash and/or other purposes such as soaking and/or pretreatment of fabrics, for example. A fabric care composition may take the form of, for example, a laundry detergent; fabric conditioner; any wash-, rinse-, or dryer-added product; unit dose; or spray. Fabric care compositions in a liquid form may be in the form of an aqueous composition as disclosed herein. In other aspects, a fabric care composition can be in a dry form such as a granular detergent or dryer-added fabric softener sheet. Other non-limiting examples of fabric care compositions herein include: granular or powder-form all-purpose or heavy-duty washing agents; liquid, gel or paste-form all-purpose or heavy-duty washing agents; liquid or dry fine-fabric (e.g., delicates) detergents; cleaning auxiliaries such as bleach additives, "stain-stick", or pre-treatments; substrate-laden products such as dry and wetted wipes, pads, or sponges; sprays and mists.

A cellulase can be incorporated into a detergent at or near a concentration conventionally used for cellulase in detergents. For example, a cellulase may be added in an amount corresponding to about 0.00001-1 mg, or about 0.01-100 mg, of cellulase (calculated as pure enzyme protein) per liter of wash liquor or dishwasher liquor. Exemplary formulations are provided herein.

A cellulase may be a component of a detergent composition, as the only enzyme or with other enzymes including other cellulase enzymes. As such, it may be included in a detergent composition in the form of a non-dusting granulate, a stabilized liquid, or a protected enzyme, for example. Non-dusting granulates may be produced, e.g., as disclosed in U.S. Pat. Nos. 4,106,991 and 4,661,452 (which are incorporated herein by reference) and may optionally be coated by methods known in the art. Examples of waxy coating materials are poly(ethylene oxide) products (e.g., polyethylene glycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of coating materials suitable for application by fluid bed techniques are given in, for example, GB 1483591, which is incorporated herein by reference. Liquid enzyme preparations may, for instance, be stabilized by adding a polyol such as propylene glycol, a sugar or sugar alcohol, lactic acid or boric acid according to established methods. Other enzyme stabilizers known in the art can be used. Protected enzymes may be prepared according to the method disclosed in, for example, EP238216, which is incorporated herein by reference.

A detergent composition herein may be in any useful form, e.g., as powders, granules, pastes, bars, unit dose or liquid. A liquid detergent may be aqueous, typically containing up to about 70 wt % of water and 0 wt % to about 30 wt % of organic solvent. It may also be in the form of a compact gel type containing only about 30 wt % water.

A detergent composition herein typically comprises one or more surfactants, wherein the surfactant is selected from nonionic surfactants, anionic surfactants, cationic surfactants, ampholytic surfactants, zwitterionic surfactants, semi-polar nonionic surfactants and mixtures thereof. In some embodiments, the surfactant is present at a level of from about 0.1% to about 60%, while in alternative embodiments the level is from about 1% to about 50%, while in still further embodiments the level is from about 5% to about 40%, by weight of the detergent composition. A detergent will usually contain 0 wt % to about 50 wt % of an anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. In addition, a detergent composition may optionally contain 0 wt % to about 40 wt % of a nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO92/06154, which is incorporated herein by reference).

A detergent composition herein typically comprises one or more detergent builders or builder systems. In some embodiments incorporating at least one builder, the cleaning compositions comprise at least about 1%, from about 3% to about 60%, or even from about 5% to about 40%, builder by weight of the composition. Builders include, but are not limited to, alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1, 3, 5-trihydroxy benzene-2, 4, 6-trisulphonic acid, and carboxymethyloxysuccinic acid, various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present disclosure. Examples of a detergent builder or complexing agent include zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). A detergent may also be unbuilt, i.e., essentially free of detergent builder.

In some embodiments, builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present disclosure, including those known in the art (See, e.g., EP2100949).

In some embodiments, builders for use herein include phosphate builders and non-phosphate builders. In some embodiments, the builder is a phosphate builder. In some embodiments, the builder is a non-phosphate builder. If present, builders are used in a level of from 0.1% to 80%, or from 5% to 60%, or from 10% to 50%, by weight of the composition. In some embodiments, the product comprises a mixture of phosphate and non-phosphate builders. Suitable phosphate builders include mono-phosphates, di-phosphates, tri-polyphosphates or oligomeric-polyphosphates, including the alkali metal salts of these compounds, including the sodium salts. In some embodiments, a builder can be sodium tripolyphosphate (STPP). Additionally, the composition can comprise carbonate and/or citrate, preferably citrate that helps to achieve a neutral pH composition. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include ammonium and/or alkali metal salts, i.e., lithium, sodium, and potassium salts, including sodium salts. Suitable polycarboxylic acids include acyclic, alicyclic, heterocyclic and aromatic carboxylic acids, wherein in some embodiments, they can contain at least two carboxyl groups which are in each case separated from one another by, in some instances, no more than two carbon atoms.

A detergent composition herein can comprise at least one chelating agent. Suitable chelating agents include, but are not limited to copper, iron and/or manganese chelating agents and mixtures thereof. In embodiments in which at least one chelating agent is used, the composition comprises from about 0.1% to about 15%, or even from about 3.0% to about 10%, chelating agent by weight of the composition.

A detergent composition herein can comprise at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

A detergent composition herein can comprise one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. Additional dye transfer inhibiting agents include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetracetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethylethylenediaminetriacetic acid (HEDTA), triethylenetetraaminehexaacetic acid (TTNA), N-hydroxyethyliminodiacetic acid (HEIDA), dihydroxyethylglycine (DHEG), ethylenediaminetetrapropionic acid (EDTP) and derivatives thereof, which can be used alone or in combination with any of the above. In embodiments in which at least one dye transfer inhibiting agent is used, a composition herein may comprise from about 0.0001% to about 10%, from about 0.01% to about 5%, or even from about 0.1% to about 3%, by weight of the composition.

A detergent composition herein can comprise silicates. In some of these embodiments, sodium silicates (e.g., sodium disilicate, sodium metasilicate, and/or crystalline phyllosilicates) find use. In some embodiments, silicates are present at a level of from about 1% to about 20% by weight of the composition. In some embodiments, silicates are present at a level of from about 5% to about 15% by weight of the composition.

A detergent composition herein can comprise dispersants. Suitable water-soluble organic materials include, but are not limited to the homo- or co-polymeric acids or their salts, in which the polycarboxylic acid comprises at least two carboxyl radicals separated from each other by not more than two carbon atoms.

Any cellulase disclosed above is contemplated for use in the disclosed detergent compositions. Suitable cellulases include, but are not limited to Humicola insolens cellulases (See, e.g., U.S. Pat. No. 4,435,307). Exemplary cellulases contemplated for such use are those having color care benefit for a textile. Examples of cellulases that provide a color care benefit are disclosed in EP0495257, EP0531372, EP531315, WO96/11262, WO96/29397, WO94/07998; WO98/12307; WO95/24471, WO98/08940, and U.S. Pat. Nos. 5,457,046, 5,686,593 and 5,763,254, all of which are incorporated herein by reference. Examples of commercially available cellulases useful in a detergent include CELLUSOFT®, CELLUCLEAN®, CELLUZYME®, and CAREZYME® (Novo Nordisk A/S and Novozymes A/S); CLAZINASE®, PURADAX HA®, and REVITALENZ™ (DuPont Industrial Biosciences); BIOTOUCH® (AB Enzymes); and KAC-500(B)™ (Kao Corporation). Additional cellulases are disclosed in, e.g., U.S. Pat. No. 7,595,182, U.S. Pat. No. 8,569,033, U.S. Pat. No. 7,138,263, U.S. Pat. No. 3,844,890, U.S. Pat. No. 4,435,307, U.S. Pat. No. 4,435,307, and GB2095275.

A detergent composition herein may additionally comprise one or more other enzymes in addition to at least one cellulase. Examples of other enzymes include proteases, cellulases, hemicellulases, peroxidases, lipolytic enzymes (e.g., metallolipolytic enzymes), xylanases, lipases, phospholipases, esterases (e.g., arylesterase, polyesterase), perhydrolases, cutinases, pectinases, pectate lyases, mannanases, keratinases, reductases, oxidases (e.g., choline oxidase, phenoloxidase), phenoloxidases, lipoxygenases, ligninases, pullulanases, tannases, pentosanases, malanases, beta-glucanases, arabinosidases, hyaluronidases, chondroitinases, laccases, metalloproteinases, amadoriases, glucoamylases, alpha-amylases, beta-amylases, galactosidases, galactanases, catalases, carageenases, hyaluronidases, keratinases, lactases, ligninases, peroxidases, phosphatases, polygalacturonases, pullulanases, rhamnogalactouronases, tannases, transglutaminases, xyloglucanases, xylosidases, metalloproteases, arabinofuranosidases, phytases, isomerases, transferases and/or amylases in any combination.

In some embodiments of the present disclosure, the detergent compositions can comprise one or more enzymes, each at a level from about 0.00001% to about 10% by weight of the composition and the balance of cleaning adjunct materials by weight of composition. In some other embodiments, the detergent compositions also comprise each enzyme at a level of about 0.0001% to about 10%, about 0.001% to about 5%, about 0.001% to about 2%, about 0.005% to about 0.5%, enzyme by weight of the composition.

Suitable proteases include those of animal, vegetable or microbial origin. In some embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from *Bacillus* (e.g., subtilisin, lentus, amyloliquefaciens, subtilisin Carlsberg, subtilisin 309, subtilisin 147 and subtilisin 168). Additional examples include those mutant proteases described in U.S. Pat. Nos. RE34606, 5955340, 5700676, 6312936 and 6482628, all of which are incorporated herein by reference. Additional protease examples include, but are not limited to, trypsin (e.g., of porcine or bovine origin), and the *Fusarium* protease described in WO89/06270. In some embodiments, commercially available protease enzymes include, but are not limited to, MAXATASE®, MAXACAL™, MAXAPEM™, OPTICLEAN®, OPTIMASE®, PROPERASE®, PURAFECT®, PURAFECT® OXP, PURAMAX™, EXCELLASE™, PREFERENZ™ proteases (e.g. P100, P110, P280), EFFECTENZ™ proteases (e.g. P1000, P1050, P2000), EXCELLENZ™ proteases (e.g. P1000), ULTIMASE®, and PURAFAST™ (Genencor); ALCALASE®, SAVINASE®, PRIMASE®, DURAZYM™, POLARZYME®, OVOZYME®, KANNASE®, LIQUANASE®, NEUTRASE®, RELASE® and ESPERASE® (Novozymes); BLAP™ and BLAP™ variants (Henkel Kommanditgesellschaft auf Aktien, Duesseldorf, Germany), and KAP (*B. alkalophilus* subtilisin; Kao Corp., Tokyo, Japan). Various proteases are described in WO95/23221, WO92/21760, WO09/149200, WO09/149144, WO09/149145, WO11/072099, WO10/056640, WO10/056653, WO11/140364, WO12/151534, U.S. Pat. Publ. No. 2008/0090747, and U.S. Pat. Nos. 5,801,039, 5,340,735, 5,500,364, 5,855,625, RE34606, 5955340, 5700676, 6312936, 6482628, 8530219, and various other patents. In some further embodiments, neutral metalloproteases find use, including but not limited to, the neutral metalloproteases described in WO1999014341, WO1999033960, WO1999014342, WO1999034003, WO2007044993, WO2009058303 and WO2009058661, all of which are incorporated herein by reference. Exemplary metalloproteases include nprE, the recombinant form of neutral metalloprotease expressed in *Bacillus subtilis* (See e.g., WO07/044993), and PMN, the purified neutral metalloprotease from *Bacillus amyloliquefaciens*.

Suitable mannanases include, but are not limited to, those of bacterial or fungal origin. Chemically or genetically modified mutants are included in some embodiments. Various mannanases are known which find use in the present disclosure (See, e.g., U.S. Pat. Nos. 6,566,114, 6,602,842, and 6,440,991, all of which are incorporated herein by reference). Commercially available mannanases that find use in the present disclosure include, but are not limited to MANNASTAR®, PURABRITE™, and MANNAWAY®.

Suitable lipases include those of bacterial or fungal origin. Chemically modified, proteolytically modified, or protein engineered mutants are included. Examples of useful lipases include those from the genera *Humicola* (e.g., *H. lanuginosa*, EP258068 and EP305216; *H. insolens*, WO96/13580), *Pseudomonas* (e.g., *P. alcaligenes* or *P. pseudoalcaligenes*, EP218272; *P. cepacia*, EP331376; *P. stutzeri*, GB1372034; *P. fluorescens* and *Pseudomonas* sp. strain SD 705, WO95/06720 and WO96/27002; *P. wisconsinensis*, WO96/12012); and *Bacillus* (e.g., *B. subtilis*, Dartois et al., Biochemica et Biophysica Acta 1131:253-360; *B. stearothermophilus*, JP64/744992; *B. pumilus*, WO91/16422). Furthermore, a number of cloned lipases find use in some embodiments of the present disclosure, including but not limited to, *Penicillium camembertii* lipase (See, Yamaguchi et al., Gene 103: 61-67 [1991]), *Geotricum candidum* lipase (See, Schimada et al., J. Biochem., 106:383-388 [1989]), and various *Rhizopus* lipases such as *R. delemar* lipase (See, Hass et al., Gene 109:117-113 [1991]), a *R. niveus* lipase (Kugimiya et al., Biosci. Biotech. Biochem. 56:716-719 [1992]) and *R. oryzae* lipase. Additional lipases useful herein include, for example, those disclosed in WO92/05249, WO94/01541, WO95/35381, WO96/00292, WO95/30744, WO94/25578, WO95/14783, WO95/22615, WO97/04079, WO97/07202, EP407225 and EP260105. Other types of lipase polypeptide enzymes such as cutinases also find use in some embodiments of the present disclosure, including but not limited to, cutinase derived from *Pseudomonas mendocina* (See, WO88/09367), and cutinase derived from *Fusarium solani pisi* (See, WO90/09446). Examples of certain commercially available lipase enzymes useful herein include M1 LIPASE™, LUMA FAST™, and LIPOMAX™ (Genencor); LIPEX®, LIPOLASE® and LIPOLASE® ULTRA (Novozymes); and LIPASE P™ "Amano" (Amano Pharmaceutical Co. Ltd., Japan).

Suitable polyesterases include, for example, those disclosed in WO01/34899, WO01/14629 and U.S. Pat. No. 6,933,140.

A detergent composition herein can also comprise 2,6-beta-D-fructan hydrolase, which is effective for removal/cleaning of certain biofilms present on household and/or industrial textiles/laundry.

Suitable amylases include, but are not limited to those of bacterial or fungal origin. Chemically or genetically modified mutants are included in some embodiments. Amylases that find use in the present disclosure, include, but are not limited to, alpha-amylases obtained from *B. licheniformis* (See e.g., GB1296839). Additional suitable amylases include those disclosed in WO9510603, WO9526397, WO9623874, WO9623873, WO9741213, WO9919467, WO0060060, WO0029560, WO9923211, WO9946399, WO0060058, WO0060059, WO9942567, WO0114532, WO02092797, WO0166712, WO0188107, WO0196537, WO0210355, WO9402597, WO0231124, WO9943793, WO9943794, WO2004113551, WO2005001064, WO2005003311, WO0164852, WO2006063594, WO2006066594, WO2006066596, WO2006012899, WO2008092919, WO2008000825, WO2005018336, WO2005066338, WO2009140504, WO2005019443, WO2010091221, WO2010088447, WO0134784, WO2006012902, WO2006031554, WO2006136161, WO2008101894, WO2010059413, WO2011098531, WO2011080352, WO2011080353, WO2011080354, WO2011082425, WO2011082429, WO2011076123, WO2011087836, WO2011076897, WO94183314, WO9535382, WO9909183, WO9826078, WO9902702, WO9743424, WO9929876, WO9100353, WO9605295, WO9630481, WO9710342, WO2008088493, WO2009149419, WO2009061381, WO2009100102, WO2010104675, WO2010117511, and WO2010115021, all of which are incorporated herein by reference.

Suitable amylases include, for example, commercially available amylases such as STAINZYME®, STAINZYME PLUS®, NATALASE®, DURAMYL®, TERMAMYL®, TERMAMYL ULTRA®, FUNGAMYL® and BAN™ (Novo Nordisk NS and Novozymes NS); RAPIDASE®, POWERASE®, PURASTAR® and PREFERENZ™ (DuPont Industrial Biosciences).

Suitable peroxidases/oxidases contemplated for use in the compositions include those of plant, bacterial or fungal origin. Chemically modified or protein engineered mutants are included. Examples of peroxidases useful herein include those from the genus *Coprinus* (e.g., *C. cinereus*, WO93/24618, WO95/10602, and WO98/15257), as well as those referenced in WO2005056782, WO2007106293, WO2008063400, WO2008106214, and WO2008106215. Commercially available peroxidases useful herein include, for example, GUARDZYME™ (Novo Nordisk NS and Novozymes NS).

In some embodiments, peroxidases are used in combination with hydrogen peroxide or a source thereof (e.g., a percarbonate, perborate or persulfate) in the compositions of the present disclosure. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO94/12621 and WO95/01426). Suitable peroxidases/oxidases include, but are not limited to, those of plant, bacterial or fungal origin. Chemically or genetically modified mutants are included in some embodiments.

Cellulase and/or other enzymes comprised in a detergent composition herein may be stabilized using conventional stabilizing agents, e.g., a polyol such as propylene glycol or glycerol; a sugar or sugar alcohol; lactic acid; boric acid or a boric acid derivative (e.g., an aromatic borate ester).

A detergent composition herein may contain about 1 wt % to about 65 wt % of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). A detergent may also be unbuilt, i.e., essentially free of detergent builder. Cellulase and optionally other enzymes comprised in a detergent herein is/are typically used with detergent ingredients that are compatible with the stability of the enzyme. Nonetheless, enzymes generally can be protected against deleterious components by known forms of encapsulation (e.g., granulation or sequestration in hydro gels).

A detergent composition in certain embodiments may comprise one or more other types of polymers in addition to a poly alpha-1,3-glucan and/or poly alpha-1,3-glucan ether compound. Examples of other types of polymers useful herein include carboxymethyl cellulose (CMC), poly(vinylpyrrolidone) (PVP), polyethylene glycol (PEG), poly(vinyl alcohol) (PVA), polycarboxylates such as polyacrylates, maleic/acrylic acid copolymers and lauryl methacrylate/acrylic acid copolymers.

A detergent composition herein may contain a bleaching system. For example, a bleaching system can comprise an $H_2O_2$ source such as perborate or percarbonate, which may be combined with a peracid-forming bleach activator such as tetraacetylethylenediamine (TAED) or nonanoyloxybenzenesulfonate (NOBS). Alternatively, a bleaching system may comprise peroxyacids (e.g., amide, imide, or sulfone type peroxyacids). Alternatively still, a bleaching system can be an enzymatic bleaching system comprising perhydrolase, for example, such as the system described in WO2005/056783.

A detergent composition herein may also contain conventional detergent ingredients such as fabric conditioners, clays, foam boosters, suds suppressors, anti-corrosion agents, soil-suspending agents, anti-soil redeposition agents, dyes, bactericides, tarnish inhibiters, optical brighteners, or perfumes. The pH of a detergent composition herein (measured in aqueous solution at use concentration) is usually neutral or alkaline (e.g., pH of about 7.0 to about 11.0).

Particular forms of detergent compositions that can be adapted for purposes disclosed herein are disclosed in, for example, US20090209445A1, US20100081598A1, U.S. Pat. No. 7,001,878B2, EP1504994B1, WO2001085888A2, WO2003089562A1, WO2009098659A1, WO2009098660A1, WO2009112992A1, WO2009124160A1, WO2009152031A1, WO2010059483A1, WO2010088112A1, WO2010090915A1, WO2010135238A1, WO2011094687A1, WO2011094690A1, WO2011127102A1, WO2011163428A1, WO2008000567A1, WO2006045391A1, WO2006007911A1, WO2012027404A1, EP1740690B1, WO2012059336A1, U.S. Pat. No. 6,730,646B1, WO2008087426A1, WO2010116139A1, and WO2012104613A1, all of which are incorporated herein by reference.

Laundry detergent compositions herein can optionally be heavy duty (all purpose) laundry detergent compositions. Exemplary heavy duty laundry detergent compositions comprise a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof), and optionally non-ionic surfactant (selected from a group of linear or branched or random chain, substituted or unsubstituted alkyl alkoxylated alcohol, e.g., C8-C18 alkyl ethoxylated alcohols and/or C6-C12 alkyl phenol alkoxylates), where the weight ratio of anionic detersive surfactant (with a hydrophilic index (Hlc) of from 6.0 to 9) to non-ionic detersive surfactant is greater than 1:1. Suitable detersive surfactants also include cationic detersive surfactants (selected from a group of alkyl pyridinium compounds, alkyl quaternary ammonium compounds, alkyl quaternary phosphonium compounds, alkyl ternary sulphonium compounds, and/or mixtures thereof); zwitterionic and/or amphoteric detersive surfactants (selected from a group of alkanolamine sulpho-betaines); ampholytic surfactants; semi-polar non-ionic surfactants and mixtures thereof.

A detergent herein such as a heavy duty laundry detergent composition may optionally include, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated C1-C6 carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: C4-C25 alkyl group, polypropylene, polybutylene, vinyl ester of a saturated C1-C6 mono-carboxylic acid, C1-C6 alkyl ester of acrylic or methacrylic acid, and mixtures thereof.

A detergent herein such as a heavy duty laundry detergent composition may optionally include additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example REPEL-O-TEX SF, SF-2 AND SRP6, TEXCARE SRA100, SRA300, SRN100, SRN170, SRN240, SRN300 AND SRN325, MARLOQUEST SL), anti-redeposition polymers (0.1 wt % to 10 wt %), include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); and polymeric carboxylate (such as maleate/acrylate random copolymer or polyacrylate homopolymer).

A detergent herein such as a heavy duty laundry detergent composition may optionally further include saturated or unsaturated fatty acids, preferably saturated or unsaturated C12-C24 fatty acids (0 wt % to 10 wt %); deposition aids in addition to a poly alpha-1,3-glucan ether compound disclosed herein (examples for which include polysaccharides, cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic starch, cationic polyacylamides, and mixtures thereof.

A detergent herein such as a heavy duty laundry detergent composition may optionally further include dye transfer inhibiting agents, examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents, examples of which include ethylene-diamine-tetraacetic acid (EDTA), diethylene triamine penta methylene phosphonic acid (DTPMP), hydroxy-ethane diphosphonic acid (HEDP), ethylenediamine N,N'-disuccinic acid (EDDS), methyl glycine diacetic acid (MGDA), diethylene triamine penta acetic acid (DTPA), propylene diamine tetracetic acid (PDTA), 2-hydroxypyridine-N-oxide (HPNO), or methyl glycine diacetic acid (MGDA), glutamic acid N,N-diacetic acid (N,N-dicarboxymethyl glutamic acid tetrasodium salt (GLDA), nitrilotriacetic acid (NTA), 4,5-dihydroxy-m-benzenedisulfonic acid, citric acid and any salts thereof, N-hydroxyethylethylenediaminetriacetic acid (HEDTA), triethylenetetraaminehexaacetic acid (TTNA), N-hydroxyethyliminodiacetic acid (HEIDA), dihydroxyethylglycine (DHEG), ethylenediaminetetrapropionic acid (EDTP), and derivatives thereof.

A detergent herein such as a heavy duty laundry detergent composition may comprise active cellulase, and optionally one or more other types of enzymes disclosed herein, each at about 0.01 wt % to about 0.03 wt % active enzyme. The composition may include an enzyme stabilizer, such as any of those disclosed herein.

A detergent herein such as a heavy duty laundry detergent composition may optionally include silicone or fatty-acid based suds suppressors; hueing dyes, calcium and magnesium cations, visual signaling ingredients, anti-foam (0.001 wt % to about 4.0 wt %), and/or a structurant/thickener (0.01 wt % to 5 wt %) selected from the group consisting of diglycerides and triglycerides, ethylene glycol distearate, microcrystalline cellulose, microfiber cellulose, biopolymers, xanthan gum, gellan gum, and mixtures thereof). Such structurant/thickener would be in addition to the one or more poly alpha-1,3-glucan compounds comprised in the detergent. A structurant can also be referred to as a structural agent, structuring agent or external structurant. These terms can be used interchangeably.

A detergent herein can be in the form of a heavy duty dry/solid laundry detergent composition, for example. Such a detergent may include: (i) a detersive surfactant, such as any anionic detersive surfactant disclosed herein, any non-ionic detersive surfactant disclosed herein, any cationic detersive surfactant disclosed herein, any zwitterionic and/or amphoteric detersive surfactant disclosed herein, any ampholytic surfactant, any semi-polar non-ionic surfactant, and mixtures thereof; (ii) a builder, such as any phosphate-free builder (e.g., zeolite builders in the range of 0 wt % to less than 10 wt %), any phosphate builder (e.g., sodium tri-polyphosphate in the range of 0 wt % to less than 10 wt %), citric acid, citrate salts and nitrilotriacetic acid, any silicate salt (e.g., sodium or potassium silicate or sodium meta-silicate in the range of 0 wt % to less than 10 wt %); any carbonate salt (e.g., sodium carbonate and/or sodium bicarbonate in the range of 0 wt % to less than 80 wt %), and mixtures thereof; (iii) a bleaching agent, such as any photobleach (e.g., sulfonated zinc phthalocyanines, sulfonated aluminum phthalocyanines, xanthenes dyes, and mixtures thereof), any hydrophobic or hydrophilic bleach activator (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, nonanoyloxybenzene sulfonate-NOBS, nitrile quats, and mixtures thereof), any source of hydrogen peroxide (e.g., inorganic perhydrate salts, examples of which include mono or tetra hydrate sodium salt of perborate, percarbonate, persulfate, perphosphate, or persilicate), any preformed hydrophilic and/or hydrophobic peracids (e.g., percarboxylic acids and salts, percarbonic acids and salts, perimidic acids and salts, peroxymonosulfuric acids and salts, and mixtures thereof); and/or (iv) any other components such as a bleach catalyst (e.g., imine bleach boosters examples of which include iminium cations and polyions, iminium zwitterions, modified amines, modified amine oxides, N-sulphonyl imines, N-phosphonyl imines, N-acyl imines, thiadiazole dioxides, perfluoroimines, cyclic sugar ketones, and mixtures thereof), and a metal-containing bleach catalyst (e.g., copper, iron, titanium, ruthenium, tungsten, molybdenum, or manganese cations along with an auxiliary metal cations such as zinc or aluminum and a sequestrate such as EDTA, ethylenediaminetetra(methylenephosphonic acid).

Compositions disclosed herein can be in the form of a dishwashing detergent composition. Examples of dishwashing detergents include automatic dishwashing detergents (typically used in dishwasher machines) and hand-washing dish detergents. A dishwashing detergent composition can be in any dry or liquid/aqueous form as disclosed herein, for example. Components that may be included in certain embodiments of a dishwashing detergent composition include, for example, one or more of a phosphate; oxygen- or chlorine-based bleaching agent; non-ionic surfactant; alkaline salt (e.g., metasilicates, alkali metal hydroxides, sodium carbonate); any active enzyme disclosed herein in addition to cellulase; anti-corrosion agent (e.g., sodium silicate); anti-foaming agent; additives to slow down the removal of glaze and patterns from ceramics; perfume; anti-caking agent (in granular detergent); starch (in tablet-based detergents); gelling agent (in liquid/gel based detergents); and/or sand (powdered detergents).

Dishwashing detergents such as an automatic dishwasher detergent or liquid dishwashing detergent can comprise (i) a non-ionic surfactant, including any ethoxylated non-ionic surfactant, alcohol alkoxylated surfactant, epoxy-capped poly(oxyalkylated) alcohol, or amine oxide surfactant present in an amount from 0 to 10 wt %; (ii) a builder, in the range of about 5-60 wt %, including any phosphate builder (e.g., mono-phosphates, di-phosphates, tri-polyphosphates, other oligomeric-polyphosphates, sodium tripolyphosphate-STPP), any phosphate-free builder (e.g., amino acid-based compounds including methyl-glycine-diacetic acid [MGDA] and salts or derivatives thereof, glutamic-N,N-diacetic acid [GLDA] and salts or derivatives thereof, iminodisuccinic acid (IDS) and salts or derivatives thereof, carboxy methyl inulin and salts or derivatives thereof, nitrilotriacetic acid [NTA], diethylene triamine penta acetic acid [DTPA], B-alaninediacetic acid [B-ADA] and salts thereof), homopolymers and copolymers of poly-carboxylic acids and partially or completely neutralized salts thereof, monomeric polycarboxylic acids and hydroxycarboxylic acids and salts thereof in the range of 0.5 wt % to 50 wt %, or sulfonated/carboxylated polymers in the range of about 0.1 wt % to about 50 wt %; (iii) a drying aid in the range of about 0.1 wt % to about 10 wt % (e.g., polyesters, especially anionic polyesters, optionally together with further monomers with 3 to 6 functionalities—typically acid, alcohol or ester functionalities which are conducive to polycondensation, polycarbonate-, polyurethane- and/or polyurea-polyorganosiloxane compounds or precursor compounds thereof, particularly of the reactive cyclic carbonate and urea type); (iv) a silicate in the range from about 1 wt % to about 20 wt % (e.g., sodium or potassium silicates such as sodium disilicate, sodium meta-silicate and crystalline phyllosilicates); (v) an inorganic bleach (e.g., perhydrate salts such as perborate, percarbonate, perphosphate, persulfate and persilicate salts) and/or an organic bleach (e.g., organic peroxyacids such as diacyl- and tetraacylperoxides, especially diperoxydodecanedioic acid, diperoxytetradecanedioic acid, and diperoxyhexadecanedioic acid); (vi) a bleach activator (e.g., organic peracid precursors in the range from about 0.1 wt % to about 10 wt %) and/or bleach catalyst (e.g., manganese triazacyclononane and related complexes; Co, Cu, Mn, and Fe bispyridylamine and related complexes; and pentamine acetate cobalt(III) and related complexes); (vii) a metal care agent in the range from about 0.1 wt % to 5 wt % (e.g., benzatriazoles, metal salts and complexes, and/or silicates); and/or (viii) any active enzyme disclosed herein in addition to cellulase in the range from about 0.01 to 5.0 mg of active enzyme per gram of automatic dishwashing detergent composition, and an enzyme stabilizer component (e.g., oligosaccharides, polysaccharides, and inorganic divalent metal salts).

Various examples of detergent formulations comprising cellulase and at least one poly alpha-1,3-glucan ether compound (e.g., a carboxyalkyl poly alpha-1,3-glucan ether such as carboxymethyl poly alpha-1,3-glucan [CMG]) are disclosed below (1-19):

1) A detergent composition formulated as a granulate having a bulk density of at least 600 g/L comprising: linear alkylbenzenesulfonate (calculated as acid) at about 7-12 wt %; alcohol ethoxysulfate (e.g., C12-18 alcohol, 1-2 ethylene oxide [EO]) or alkyl sulfate (e.g., C16-18) at about 1-4 wt %; alcohol ethoxylate (e.g., C14-15 alcohol) at about 5-9 wt %; sodium carbonate at about 14-20 wt %; soluble silicate (e.g., $Na_2O$ $2SiO_2$) at about 2-6 wt %; zeolite (e.g., $NaAlSiO_4$) at about 15-22 wt %; sodium sulfate at about 0-6 wt %; sodium citrate/citric acid at about 0-15 wt %; sodium perborate at about 11-18 wt %; TAED at about 2-6 wt %; poly alpha-1,3-glucan ether (e.g. CMG) up to about 2 wt %; other polymers (e.g., maleic/acrylic acid copolymer, PVP, PEG) at about 0-3 wt %; cellulase and optionally other enzymes (calculated as pure enzyme protein) at about 0.0001-0.1 wt %; and minor ingredients (e.g., suds suppressors, perfumes, optical brightener, photobleach) at about 0-5 wt %.

2) A detergent composition formulated as a granulate having a bulk density of at least 600 g/L comprising: linear alkylbenzenesulfonate (calculated as acid) at about 6-11 wt %; alcohol ethoxysulfate (e.g., C12-18 alcohol, 1-2 EO) or alkyl sulfate (e.g., C16-18) at about 1-3 wt %; alcohol ethoxylate (e.g., C14-15 alcohol) at about 5-9 wt %; sodium carbonate at about 15-21 wt %; soluble silicate (e.g., $Na_2O$ $2SiO_2$) at about 1-4 wt %; zeolite (e.g., $NaAlSiO_4$) at about 24-34 wt %; sodium sulfate at about 4-10 wt %; sodium citrate/citric acid at about 0-15 wt %; sodium perborate at about 11-18 wt %; TAED at about 2-6 wt %; poly alpha-1,3-glucan ether (e.g. CMG) up to about 2 wt %; other polymers (e.g., maleic/acrylic acid copolymer, PVP, PEG) at about 1-6 wt %; cellulase and optionally other enzymes (calculated as pure enzyme protein) at about 0.0001-0.1 wt %; and minor ingredients (e.g., suds suppressors, perfumes, optical brightener, photobleach) at about 0-5 wt %.

3) A detergent composition formulated as a granulate having a bulk density of at least 600 g/L comprising: linear alkylbenzenesulfonate (calculated as acid) at about 5-9 wt %; alcohol ethoxysulfate (e.g., C12-18 alcohol, 7 EO) at about 7-14 wt %; soap as fatty acid (e.g., C16-22 fatty acid) at about 1-3 wt %; sodium carbonate at about 10-17 wt %; soluble silicate (e.g., $Na_2O$ $2SiO_2$) at about 3-9 wt %; zeolite (e.g., $NaAlSiO_4$) at about 23-33 wt %; sodium sulfate at about 0-4 wt %; sodium perborate at about 8-16 wt %; TAED at about 2-8 wt %; phosphonate (e.g., EDTMPA) at about 0-1 wt %; poly alpha-1,3-glucan ether (e.g. CMG) up to about 2 wt %; other polymers (e.g., maleic/acrylic acid copolymer, PVP, PEG) at about 0-3 wt %; cellulase and optionally other enzymes (calculated as pure enzyme protein) at about 0.0001-0.1 wt %; and minor ingredients (e.g., suds suppressors, perfumes, optical brightener) at about 0-5 wt %.

4) A detergent composition formulated as a granulate having a bulk density of at least 600 g/L comprising: linear alkylbenzenesulfonate (calculated as acid) at about 8-12 wt %; alcohol ethoxylate (e.g., C12-18 alcohol, 7 EO) at about 10-25 wt %; sodium carbonate at about 14-22 wt %; soluble silicate (e.g., $Na_2O$ $2SiO_2$) at about 1-5 wt %; zeolite (e.g., $NaAlSiO_4$) at about 25-35 wt %; sodium sulfate at about 0-10 wt %; sodium perborate at about 8-16 wt %; TAED at about 2-8 wt %; phosphonate (e.g., EDTMPA) at about 0-1 wt %; poly alpha-1,3-glucan ether (e.g. CMG) up to about 2 wt %; other polymers (e.g., maleic/acrylic acid copolymer, PVP, PEG) at about 1-3 wt %; cellulase and optionally other enzymes (calculated as pure enzyme protein) at about 0.0001-0.1 wt %; and minor ingredients (e.g., suds suppressors, perfumes) at about 0-5 wt %.

5) An aqueous liquid detergent composition comprising: linear alkylbenzenesulfonate (calculated as acid) at about 15-21 wt %; alcohol ethoxylate (e.g., C12-18 alcohol, 7 EO; or C12-15 alcohol, 5 EO) at about 12-18 wt %; soap as fatty acid (e.g., oleic acid) at about 3-13 wt %; alkenylsuccinic acid (C12-14) at about 0-13 wt %; aminoethanol at about 8-18 wt %; citric acid at about 2-8 wt %; phosphonate at about 0-3 wt %; poly alpha-1,3-glucan ether (e.g. CMG) up to about 2 wt %; other polymers (e.g., PVP, PEG) at about 0-3 wt %; borate at about 0-2 wt %; ethanol at about 0-3 wt %; propylene glycol at about 8-14 wt %; cellulase and optionally other enzymes (calculated as pure enzyme protein) at about 0.0001-0.1 wt %; and minor ingredients (e.g., dispersants, suds suppressors, perfume, optical brightener) at about 0-5 wt %.

6) An aqueous structured liquid detergent composition comprising: linear alkylbenzenesulfonate (calculated as acid) at about 15-21 wt %; alcohol ethoxylate (e.g., C12-18 alcohol, 7 EO; or C12-15 alcohol, 5 EO) at about 3-9 wt %; soap as fatty acid (e.g., oleic acid) at about 3-10 wt %; zeolite (e.g., $NaAlSiO_4$) at about 14-22 wt %; potassium citrate about 9-18 wt %; borate at about 0-2 wt %; poly alpha-1,3-glucan ether (e.g. CMG) up to about 2 wt %; other polymers (e.g., PVP, PEG) at about 0-3 wt %; ethanol at about 0-3 wt %; anchoring polymers (e.g., lauryl methacrylate/acrylic acid copolymer, molar ratio 25:1, MW 3800) at about 0-3 wt %; glycerol at about 0-5 wt %; cellulase and optionally other enzymes (calculated as pure enzyme protein) at about 0.0001-0.1 wt %; and minor ingredients (e.g., dispersants, suds suppressors, perfume, optical brightener) at about 0-5 wt %.

7) A detergent composition formulated as a granulate having a bulk density of at least 600 g/L comprising: fatty alcohol sulfate at about 5-10 wt %, ethoxylated fatty acid monoethanolamide at about 3-9 wt %; soap as fatty acid at about 0-3 wt %; sodium carbonate at about 5-10 wt %; soluble silicate (e.g., $Na_2O\ 2SiO_2$) at about 1-4 wt %; zeolite (e.g., $NaAlSiO_4$) at about 20-40 wt %; sodium sulfate at about 2-8 wt %; sodium perborate at about 12-18 wt %; TAED at about 2-7 wt %; poly alpha-1,3-glucan ether (e.g. CMG) up to about 2 wt %; other polymers (e.g., maleic/acrylic acid copolymer, PEG) at about 1-5 wt %; cellulase and optionally other enzymes (calculated as pure enzyme protein) at about 0.0001-0.1 wt %; and minor ingredients (e.g., optical brightener, suds suppressors, perfumes) at about 0-5 wt %.

8) A detergent composition formulated as a granulate comprising: linear alkylbenzenesulfonate (calculated as acid) at about 8-14 wt %; ethoxylated fatty acid monoethanolamide at about 5-11 wt %; soap as fatty acid at about 0-3 wt %; sodium carbonate at about 4-10 wt %; soluble silicate (e.g., $Na_2O\ 2SiO_2$) at about 1-4 wt %; zeolite (e.g., $NaAlSiO_4$) at about 30-50 wt %; sodium sulfate at about 3-11 wt %; sodium citrate at about 5-12 wt %; poly alpha-1,3-glucan ether (e.g. CMG) up to about 2 wt %; other polymers (e.g., PVP, maleic/acrylic acid copolymer, PEG) at about 1-5 wt %; cellulase and optionally other enzymes (calculated as pure enzyme protein) at about 0.0001-0.1 wt %; and minor ingredients (e.g., suds suppressors, perfumes) at about 0-5 wt %.

9) A detergent composition formulated as a granulate comprising: linear alkylbenzenesulfonate (calculated as acid) at about 6-12 wt %; nonionic surfactant at about 1-4 wt %; soap as fatty acid at about 2-6 wt %; sodium carbonate at about 14-22 wt %; zeolite (e.g., $NaAlSiO_4$) at about 18-32 wt %; sodium sulfate at about 5-20 wt %; sodium citrate at about 3-8 wt %; sodium perborate at about 4-9 wt %; bleach activator (e.g., NOBS or TAED) at about 1-5 wt %; poly alpha-1,3-glucan ether (e.g. CMG) up to about 2 wt %; other polymers (e.g., polycarboxylate or PEG) at about 1-5 wt %; cellulase and optionally other enzymes (calculated as pure enzyme protein) at about 0.0001-0.1 wt %; and minor ingredients (e.g., optical brightener, perfume) at about 0-5 wt %.

10) An aqueous liquid detergent composition comprising: linear alkylbenzenesulfonate (calculated as acid) at about 15-23 wt %; alcohol ethoxysulfate (e.g., C12-15 alcohol, 2-3 EO) at about 8-15 wt %; alcohol ethoxylate (e.g., C12-15 alcohol, 7 EO; or C12-15 alcohol, 5 EO) at about 3-9 wt %; soap as fatty acid (e.g., lauric acid) at about 0-3 wt %; aminoethanol at about 1-5 wt %; sodium citrate at about 5-10 wt %; hydrotrope (e.g., sodium toluenesulfonate) at about 2-6 wt %; borate at about 0-2 wt %; poly alpha-1,3-glucan ether (e.g. CMG) up to about 1 wt %; ethanol at about 1-3 wt %; propylene glycol at about 2-5 wt %; cellulase and optionally other enzymes (calculated as pure enzyme protein) at about 0.0001-0.1 wt %; and minor ingredients (e.g., dispersants, perfume, optical brighteners) at about 0-5 wt %.

11) An aqueous liquid detergent composition comprising: linear alkylbenzenesulfonate (calculated as acid) at about 20-32 wt %; alcohol ethoxylate (e.g., C12-15 alcohol, 7 EO; or C12-15 alcohol, 5 EO) at about 6-12 wt %; aminoethanol at about 2-6 wt %; citric acid at about 8-14 wt %; borate at about 1-3 wt %; poly alpha-1,3-glucan ether (e.g. CMG) up to about 2 wt %; ethanol at about 1-3 wt %; propylene glycol at about 2-5 wt %; other polymers (e.g., maleic/acrylic acid copolymer, anchoring polymer such as lauryl methacrylate/acrylic acid copolymer) at about 0-3 wt %; glycerol at about 3-8 wt %; cellulase and optionally other enzymes (calculated as pure enzyme protein) at about 0.0001-0.1 wt %; and minor ingredients (e.g., hydrotropes, dispersants, perfume, optical brighteners) at about 0-5 wt %.

12) A detergent composition formulated as a granulate having a bulk density of at least 600 g/L comprising: anionic surfactant (e.g., linear alkylbenzenesulfonate, alkyl sulfate, alpha-olefinsulfonate, alpha-sulfo fatty acid methyl esters, alkanesulfonates, soap) at about 25-40 wt %; nonionic surfactant (e.g., alcohol ethoxylate) at about 1-10 wt %; sodium carbonate at about 8-25 wt %; soluble silicate (e.g., $Na_2O\ 2SiO_2$) at about 5-15 wt %; sodium sulfate at about 0-5 wt %; zeolite ($NaAlSiO_4$) at about 15-28 wt %; sodium perborate at about 0-20 wt %; bleach activator (e.g., TAED or NOBS) at about 0-5 wt %; poly alpha-1,3-glucan ether (e.g. CMG) up to about 2 wt %; cellulase and optionally other enzymes (calculated as pure enzyme protein) at about 0.0001-0.1 wt %; and minor ingredients (e.g., perfume, optical brighteners) at about 0-3 wt %.

13) Detergent compositions as described in (1)-(12) above, but in which all or part of the linear alkylbenzenesulfonate is replaced by C12-C18 alkyl sulfate.

14) A detergent composition formulated as a granulate having a bulk density of at least 600 g/L comprising: C12-C18 alkyl sulfate at about 9-15 wt %; alcohol ethoxylate at about 3-6 wt %; polyhydroxy alkyl fatty acid amide at about 1-5 wt %; zeolite (e.g., $NaAlSiO_4$) at about 10-20 wt %; layered disilicate (e.g., SK56 from Hoechst) at about 10-20 wt %; sodium carbonate at about 3-12 wt %; soluble silicate (e.g., $Na_2O\ 2SiO_2$) at 0-6 wt %; sodium citrate at about 4-8 wt %; sodium percarbonate at about 13-22 wt %; TAED at about 3-8 wt %; poly alpha-1,3-glucan ether (e.g. CMG) up to about 2 wt %; other polymers (e.g., polycarboxylates and PVP) at about 0-5 wt %; cellulase and optionally other enzymes (calculated as pure enzyme protein) at about 0.0001-0.1 wt %; and minor ingredients (e.g., optical brightener, photobleach, perfume, suds suppressors) at about 0-5 wt %.

15) A detergent composition formulated as a granulate having a bulk density of at least 600 g/L comprising: C12-C18 alkyl sulfate at about 4-8 wt %; alcohol ethoxylate at about 11-15 wt %; soap at about 1-4 wt %; zeolite MAP or zeolite A at about 35-45 wt %; sodium carbonate at about 2-8 wt %; soluble silicate (e.g., $Na_2O\ 2SiO_2$) at 0-4 wt %; sodium percarbonate at about 13-22 wt %; TAED at about 1-8 wt %; poly alpha-1,3-glucan ether (e.g. CMG) up to about 3 wt %; other polymers (e.g., polycarboxylates and PVP) at about 0-3 wt %; cellulase and optionally other enzymes (calculated as pure enzyme protein) at about 0.0001-0.1 wt %; and minor ingredients (e.g., optical brightener, phosphonate, perfume) at about 0-3 wt %.

16) Detergent formulations as described in (1)-(15) above, but that contain a stabilized or encapsulated peracid, either as an additional component or as a substitute for an already specified bleach system(s).

17) Detergent compositions as described in (1), (3), (7), (9) and (12) above, but in which perborate is replaced by percarbonate.

18) Detergent compositions as described in (1), (3), (7), (9), (12), (14) and (15) above, but that additionally contain a manganese catalyst. A manganese catalyst, for example, is one of the compounds described by Hage et al. (1994, *Nature* 369:637-639), which is incorporated herein by reference.

19) Detergent compositions formulated as a non-aqueous detergent liquid comprising a liquid non-ionic surfactant (e.g., a linear alkoxylated primary alcohol), a builder system (e.g., phosphate), poly alpha-1,3-glucan ether (e.g. CMG), a cellulase and possibly other enzymes, and alkali. The detergent may also comprise an anionic surfactant and/or bleach system.

The example detergent formulations provided in 1-19 above may alternatively contain, for example, minimally about 0.01-0.1 ppm total cellulase protein, or about 0.1-10 ppb total cellulase protein (e.g., less than 1 ppm), to maximally about 100, 200, 500, 1000, 2000, 3000, 4000, or 5000 ppm total cellulase protein, for example.

It is believed that numerous commercially available detergent formulations can be adapted to include cellulase and a poly alpha-1,3-glucan ether compound. Examples include PUREX® ULTRAPACKS (Henkel), FINISH® QUANTUM (Reckitt Benckiser), CLOROX™ 2 PACKS (Clorox), OXICLEAN MAX FORCE POWER PAKS (Church & Dwight), TIDE® STAIN RELEASE, CASCADE® ACTIONPACS, and TIDE® PODS™ (Procter & Gamble).

Compositions disclosed herein can be in the form of an oral care composition. Examples of oral care compositions include dentifrices, toothpaste, mouth wash, mouth rinse, chewing gum, and edible strips that provide some form of oral care (e.g., treatment or prevention of cavities [dental caries], gingivitis, plaque, tartar, and/or periodontal disease). An oral care composition can also be for treating an "oral surface", which encompasses any soft or hard surface within the oral cavity including surfaces of the tongue, hard and soft palate, buccal mucosa, gums and dental surfaces. A "dental surface" herein is a surface of a natural tooth or a hard surface of artificial dentition including a crown, cap, filling, bridge, denture, or dental implant, for example.

One or more poly alpha-1,3-glucan and/or poly alpha-1,3-glucan ether compounds comprised in an oral care composition typically are provided therein as a thickening agent and/or dispersion agent, which may be useful to impart a desired consistency and/or mouth feel to the composition. An oral care composition herein can comprise about 0.01-15.0 wt % (e.g., ~0.1-10 wt % or ~0.1-5.0 wt %, ~0.1-2.0 wt %) of one or more poly alpha-1,3-glucan and/or poly alpha-1,3-glucan ether compounds disclosed herein (e.g., a carboxyalkyl poly alpha-1,3-glucan ether such as carboxymethyl poly alpha-1,3-glucan [CMG]), for example. One or more other thickening agents or dispersion agents can also be provided in an oral care composition herein, such as a carboxyvinyl polymer, carrageenan (e.g., L-carrageenan), natural gum (e.g., karaya, xanthan, gum arabic, tragacanth), colloidal magnesium aluminum silicate, or colloidal silica, for example.

An oral care composition herein may be a toothpaste or other dentifrice, for example. Such compositions, as well as any other oral care composition herein, can additionally comprise, without limitation, one or more of an anticaries agent, antimicrobial or antibacterial agent, anticalculus or tartar control agent, surfactant, abrasive, pH-modifying agent, foam modulator, humectant, flavorant, sweetener, pigment/colorant, whitening agent, and/or other suitable components. Examples of oral care compositions to which cellulase and one or more poly alpha-1,3-glucan ether compounds can be added are disclosed in U.S. Patent Appl. Publ. Nos. 2006/0134025, 2002/0022006 and 2008/0057007, which are incorporated herein by reference.

An anticaries agent herein can be an orally acceptable source of fluoride ions. Suitable sources of fluoride ions include fluoride, monofluorophosphate and fluorosilicate salts as well as amine fluorides, including olaflur (N'-octadecyltrimethylendiamine-N,N,N'-tris(2-ethanol)-dihydrofluoride), for example. An anticaries agent can be present in an amount providing a total of about 100-20000 ppm, about 200-5000 ppm, or about 500-2500 ppm, fluoride ions to the composition, for example. In oral care compositions in which sodium fluoride is the sole source of fluoride ions, an amount of about 0.01-5.0 wt %, about 0.05-1.0 wt %, or about 0.1-0.5 wt %, sodium fluoride can be present in the composition, for example.

An antimicrobial or antibacterial agent suitable for use in an oral care composition herein includes, for example, phenolic compounds (e.g., 4-allylcatechol; p-hydroxybenzoic acid esters such as benzylparaben, butylparaben, ethylparaben, methylparaben and propylparaben; 2-benzylphenol; butylated hydroxyanisole; butylated hydroxytoluene; capsaicin; carvacrol; creosol; eugenol; guaiacol; halogenated bisphenolics such as hexachlorophene and bromochlorophene; 4-hexylresorcinol; 8-hydroxyquinoline and salts thereof; salicylic acid esters such as menthyl salicylate, methyl salicylate and phenyl salicylate; phenol; pyrocatechol; salicylanilide; thymol; halogenated diphenylether compounds such as triclosan and triclosan monophosphate), copper (II) compounds (e.g., copper (II) chloride, fluoride, sulfate and hydroxide), zinc ion sources (e.g., zinc acetate, citrate, gluconate, glycinate, oxide, and sulfate), phthalic acid and salts thereof (e.g., magnesium monopotassium phthalate), hexetidine, octenidine, sanguinarine, benzalkonium chloride, domiphen bromide, alkylpyridinium chlorides (e.g. cetylpyridinium chloride, tetradecylpyridinium chloride, N-tetradecyl-4-ethylpyridinium chloride), iodine, sulfonamides, bisbiguanides (e.g., alexidine, chlorhexidine, chlorhexidine digluconate), piperidino derivatives (e.g., delmopinol, octapinol), magnolia extract, grapeseed extract, rosemary extract, menthol, geraniol, citral, eucalyptol, antibiotics (e.g., augmentin, amoxicillin, tetracycline, doxycycline, minocycline, metronidazole, neomycin, kanamycin, clindamycin), and/or any antibacterial agents disclosed in U.S. Pat. No. 5,776,435, which is incorporated herein by reference. One or more antimicrobial agents can optionally be present at about 0.01-10 wt % (e.g., 0.1-3 wt %), for example, in the disclosed oral care composition.

An anticalculus or tartar control agent suitable for use in an oral care composition herein includes, for example, phosphates and polyphosphates (e.g., pyrophosphates), polyaminopropanesulfonic acid (AMPS), zinc citrate trihydrate, polypeptides (e.g., polyaspartic and polyglutamic acids), polyolefin sulfonates, polyolefin phosphates, diphosphonates (e.g., azacycloalkane-2,2-diphosphonates such as azacycloheptane-2,2-diphosphonic acid), N-methyl azacyclopentane-2,3-diphosphonic acid, ethane-1-hydroxy-1,1-diphosphonic acid (EHDP), ethane-1-amino-1,1-diphosphonate, and/or phosphonoalkane carboxylic acids and salts thereof (e.g., their alkali metal and ammonium salts). Useful inorganic phosphate and polyphosphate salts include, for example, monobasic, dibasic and tribasic sodium phosphates, sodium tripolyphosphate, tetrapolyphosphate, mono-, di-, tri- and tetra-sodium pyrophosphates, disodium dihydrogen pyrophosphate, sodium trimetaphosphate, sodium hexametaphosphate, or any of these in which sodium is replaced by potassium or ammonium. Other useful anticalculus agents in certain embodiments include anionic polycarboxylate polymers (e.g., polymers or copolymers of acrylic acid, methacrylic, and maleic anhydride such as polyvinyl methyl ether/maleic anhydride copolymers). Still other useful anticalculus agents include sequestering agents such as hydroxycarboxylic acids (e.g., citric, fumaric, malic, glutaric and oxalic acids and salts thereof) and aminopolycarboxylic acids (e.g., EDTA). One or more anticalculus or tartar control agents can optionally be present at about 0.01-50 wt % (e.g., about 0.05-25 wt % or about 0.1-15 wt %), for example, in the disclosed oral care composition.

A surfactant suitable for use in an oral care composition herein may be anionic, non-ionic, or amphoteric, for example. Suitable anionic surfactants include, without limitation, water-soluble salts of $C_{8-20}$ alkyl sulfates, sulfonated monoglycerides of $C_{8-20}$ fatty acids, sarcosinates, and taurates. Examples of anionic surfactants include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable non-ionic surfactants include, without limitation, poloxamers, polyoxyethylene sorbitan esters, fatty alcohol ethoxylates, alkylphenol ethoxylates, tertiary amine oxides, tertiary phosphine oxides, and dialkyl sulfoxides. Suitable amphoteric surfactants include, without limitation, derivatives of $C_{8-20}$ aliphatic secondary and tertiary amines having an anionic group such as a carboxylate, sulfate, sulfonate, phosphate or phosphonate. An example of a suitable amphoteric surfactant is cocoamidopropyl betaine. One or more surfactants are optionally present in a total amount of about 0.01-10 wt % (e.g., about 0.05-5.0 wt % or about 0.1-2.0 wt %), for example, in the disclosed oral care composition.

An abrasive suitable for use in an oral care composition herein may include, for example, silica (e.g., silica gel, hydrated silica, precipitated silica), alumina, insoluble phosphates, calcium carbonate, and resinous abrasives (e.g., a urea-formaldehyde condensation product). Examples of insoluble phosphates useful as abrasives herein are orthophosphates, polymetaphosphates and pyrophosphates, and include dicalcium orthophosphate dihydrate, calcium pyrophosphate, beta-calcium pyrophosphate, tricalcium phosphate, calcium polymetaphosphate and insoluble sodium polymetaphosphate. One or more abrasives are optionally present in a total amount of about 5-70 wt % (e.g., about 10-56 wt % or about 15-30 wt %), for example, in the disclosed oral care composition. The average particle size of an abrasive in certain embodiments is about 0.1-30 microns (e.g., about 1-20 microns or about 5-15 microns).

An oral care composition in certain embodiments may comprise at least one pH-modifying agent. Such agents may be selected to acidify, make more basic, or buffer the pH of a composition to a pH range of about 2-10 (e.g., pH ranging from about 2-8, 3-9, 4-8, 5-7, 6-10, or 7-9). Examples of pH-modifying agents useful herein include, without limitation, carboxylic, phosphoric and sulfonic acids; acid salts (e.g., monosodium citrate, disodium citrate, monosodium malate); alkali metal hydroxides (e.g. sodium hydroxide, carbonates such as sodium carbonate, bicarbonates, sesquicarbonates); borates; silicates; phosphates (e.g., monosodium phosphate, trisodium phosphate, pyrophosphate salts); and imidazole.

A foam modulator suitable for use in an oral care composition herein may be a polyethylene glycol (PEG), for example. High molecular weight PEGs are suitable, including those having an average molecular weight of about 200000-7000000 (e.g., about 500000-5000000 or about 1000000-2500000), for example. One or more PEGs are optionally present in a total amount of about 0.1-10 wt % (e.g. about 0.2-5.0 wt % or about 0.25-2.0 wt %), for example, in the disclosed oral care composition.

An oral care composition in certain embodiments may comprise at least one humectant. A humectant in certain embodiments may be a polyhydric alcohol such as glycerin, sorbitol, xylitol, or a low molecular weight PEG. Most suitable humectants also may function as a sweetener herein. One or more humectants are optionally present in a total amount of about 1.0-70 wt % (e.g., about 1.0-50 wt %, about 2-25 wt %, or about 5-15 wt %), for example, in the disclosed oral care composition.

A natural or artificial sweetener may optionally be comprised in an oral care composition herein. Examples of suitable sweeteners include dextrose, sucrose, maltose, dextrin, invert sugar, mannose, xylose, ribose, fructose, levulose, galactose, corn syrup (e.g., high fructose corn syrup or corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, and cyclamates. One or more sweeteners are optionally present in a total amount of about 0.005-5.0 wt %, for example, in the disclosed oral care composition.

A natural or artificial flavorant may optionally be comprised in an oral care composition herein. Examples of suitable flavorants include vanillin; sage; marjoram; parsley oil; spearmint oil; cinnamon oil; oil of wintergreen (methylsalicylate); peppermint oil; clove oil; bay oil; anise oil; eucalyptus oil; citrus oils; fruit oils; essences such as those derived from lemon, orange, lime, grapefruit, apricot, banana, grape, apple, strawberry, cherry, or pineapple; bean- and nut-derived flavors such as coffee, cocoa, cola, peanut, or almond; and adsorbed and encapsulated flavorants. Also encompassed within flavorants herein are ingredients that provide fragrance and/or other sensory effect in the mouth, including cooling or warming effects. Such ingredients include, without limitation, menthol, menthyl acetate, menthyl lactate, camphor, eucalyptus oil, eucalyptol, anethole, eugenol, cassia, oxanone, Irisone®, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), and menthone glycerol acetal (MGA). One or more flavorants are optionally present in a total amount of about 0.01-5.0 wt % (e.g., about 0.1-2.5 wt %), for example, in the disclosed oral care composition.

An oral care composition in certain embodiments may comprise at least one bicarbonate salt. Any orally acceptable bicarbonate can be used, including alkali metal bicarbonates such as sodium or potassium bicarbonate, and ammonium bicarbonate, for example. One or more bicarbonate salts are optionally present in a total amount of about 0.1-50 wt % (e.g., about 1-20 wt %), for example, in the disclosed oral care composition.

An oral care composition in certain embodiments may comprise at least one whitening agent and/or colorant. A suitable whitening agent is a peroxide compound such as any of those disclosed in U.S. Pat. No. 8,540,971, which is incorporated herein by reference. Suitable colorants herein include pigments, dyes, lakes and agents imparting a particular luster or reflectivity such as pearling agents, for example. Specific examples of colorants useful herein include talc; mica; magnesium carbonate; calcium carbonate; magnesium silicate; magnesium aluminum silicate;

silica; titanium dioxide; zinc oxide; red, yellow, brown and black iron oxides; ferric ammonium ferrocyanide; manganese violet; ultramarine; titaniated mica; and bismuth oxychloride. One or more colorants are optionally present in a total amount of about 0.001-20 wt % (e.g., about 0.01-10 wt % or about 0.1-5.0 wt %), for example, in the disclosed oral care composition.

Additional components that can optionally be included in an oral composition herein include enzymes other than cellulase, vitamins, and anti-adhesion agents, for example. Enzymes such as proteases can be added for anti-stain and other effects in certain embodiments. Examples of vitamins useful herein include vitamin C, vitamin E, vitamin B5, and folic acid. Examples of suitable anti-adhesion agents include solbrol, ficin, and quorum-sensing inhibitors.

The present disclosure also concerns a method for preparing an aqueous composition. This method comprises contacting one or more poly alpha-1,3-glucan ether compounds disclosed herein with an aqueous composition. The poly alpha-1,3-glucan ether compound(s) used in this method is represented by the structure:

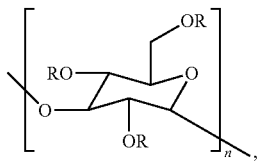

Regarding the formula of this structure, n can be at least 6, and each R can independently be an H or an organic group. Furthermore, the poly alpha-1,3-glucan ether compound has a degree of substitution with the organic group of about 0.05 to about 3.0. An aqueous composition produced by this method can comprise one or more cellulase enzymes.

In certain embodiments of the preparation method, the (i) the viscosity of the aqueous composition is increased by the poly alpha-1,3-glucan ether compound, and/or (ii) the shear thinning behavior or the shear thickening behavior of the aqueous composition is increased by the poly alpha-1,3-glucan ether compound. The viscosity of an aqueous composition before the contacting step, measured at about 20-25° C., can be about 0-10000 cPs (or any integer between 0-10000 cPs), for example. Since the aqueous composition can be a hydrocolloid or the like in certain embodiments, it should be apparent that the method can be used to increase the viscosity of aqueous compositions that are already viscous.

Contacting a poly alpha-1,3-glucan ether compound disclosed herein with an aqueous composition increases the viscosity of the aqueous composition in certain embodiments. This increase in viscosity can be an increase of at least about 1%, 10%, 100%, 1000%, 100000%, or 1000000% (or any integer between 1% and 1000000%), for example, compared to the viscosity of the aqueous composition before the contacting step. It should be apparent that very large percent increases in viscosity can be obtained with the disclosed method when the aqueous composition has little to no viscosity before the contacting step.

Contacting a poly alpha-1,3-glucan ether compound disclosed herein with an aqueous composition increases the shear thinning behavior or the shear thickening behavior of the aqueous composition in certain embodiments. Thus, a poly alpha-1,3-glucan ether compound rheologically modifies the aqueous composition in these embodiments. The increase in shear thinning or shear thickening behavior can be an increase of at least about 1%, 10%, 100%, 1000%, 100000%, or 1000000% (or any integer between 1% and 1000000%), for example, compared to the shear thinning or shear thickening behavior of the aqueous composition before the contacting step. It should be apparent that very large percent increases in rheologic modification can be obtained with the disclosed method when the aqueous composition has little to no rheologic behavior before the contacting step.

The contacting step in the disclosed method of preparing an aqueous composition can be performed by mixing or dissolving a poly alpha-1,3-glucan ether compound(s) disclosed herein in the aqueous composition by any means known in the art. For example, mixing or dissolving can be performed manually or with a machine (e.g., industrial mixer or blender, orbital shaker, stir plate, homogenizer, sonicator, bead mill). Mixing or dissolving can comprise a homogenization step in certain embodiments. Homogenization (as well as any other type of mixing) can be performed for about 5 to 60, 5 to 30, 10 to 60, 10 to 30, 5 to 15, or 10 to 15 seconds (or any integer between 5 and 60 seconds), or longer periods of time as necessary to mix a poly alpha-1, 3-glucan ether compound with the aqueous composition. A homogenizer can be used at about 5000 to 30000 rpm, 10000 to 30000 rpm, 15000 to 30000 rpm, 15000 to 25000 rpm, or 20000 rpm (or any integer between 5000 and 30000 rpm), for example.

After a poly alpha-1,3-glucan ether compound is mixed with or dissolved into an aqueous composition, the resulting aqueous composition may be filtered, or may not be filtered. For example, an aqueous composition prepared with a homogenization step may or may not be filtered.

An aqueous composition prepared by the disclosed preparation method comprises one or more active cellulase enzymes. A cellulase can be (i) comprised in the aqueous composition prior to the contacting step, or (ii) added to the aqueous composition during or after the contacting step. For instances when a poly alpha-1,3-glucan ether compound is contacted with an aqueous composition already containing a cellulase, it would be known in the art how to mix or dissolve the ether compound without significantly affecting cellulase activity. Cellulase and poly alpha-1,3-glucan ether can simultaneously be contacted with an aqueous composition, if desired. For example, cellulase and poly alpha-1,3-glucan ether may be comprised together within a dry composition (e.g., laundry detergent powder) that is added to an aqueous composition. Alternatively, cellulase may be added to an aqueous composition which already comprises one or more poly alpha-1,3-glucan ether compounds.

Examples of cellulase enzymes, poly alpha-1,3-glucan ether compounds, and concentrations of each of these components, suitable for the preparation method are disclosed herein.

Certain embodiments of a method of preparing an aqueous composition can be used to prepare an aqueous composition disclosed herein, such as a household product (e.g., laundry detergent, fabric softener, dishwasher detergent), personal care product (e.g., a water-containing dentifrice such as toothpaste), or industrial product.

The present disclosure also concerns a method of treating a material. This method comprises contacting a material with an aqueous composition comprising at least one cellulase and at least one poly alpha-1,3-glucan ether compound disclosed herein. A poly alpha-1,3-glucan ether compound(s) used in this method is represented by the structure:

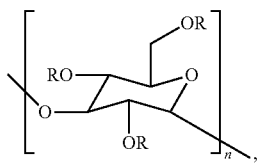

Regarding the formula of this structure, n can be at least 6, and each R can independently be an H or an organic group. Furthermore, the poly alpha-1,3-glucan ether compound has a degree of substitution with the organic group of about 0.05 to about 3.0.

A material contacted with an aqueous composition in a contacting method herein can comprise a fabric in certain embodiments. A fabric herein can comprise natural fibers, synthetic fibers, semi-synthetic fibers, or any combination thereof. A semi-synthetic fiber herein is produced using naturally occurring material that has been chemically derivatized, an example of which is rayon. Non-limiting examples of fabric types herein include fabrics made of (i) cellulosic fibers such as cotton (e.g., broadcloth, canvas, chambray, chenille, chintz, corduroy, cretonne, damask, denim, flannel, gingham, jacquard, knit, matelassé, oxford, percale, poplin, plisse, sateen, seersucker, sheers, terry cloth, velvet), rayon (e.g., viscose, modal, lyocell), linen, and Tencel®; (ii) proteinaceous fibers such as silk, wool and related mammalian fibers; (iii) synthetic fibers such as polyester, acrylic, nylon, and the like; (iv) long vegetable fibers from jute, flax, ramie, coir, kapok, sisal, henequen, abaca, hemp and sunn; and (v) any combination of a fabric of (i)-(iv). Fabric comprising a combination of fiber types (e.g., natural and synthetic) include those with both a cotton fiber and polyester, for example. Materials/articles containing one or more fabrics herein include, for example, clothing, curtains, drapes, upholstery, carpeting, bed linens, bath linens, tablecloths, sleeping bags, tents, car interiors, etc. Other materials comprising natural and/or synthetic fibers include, for example, non-woven fabrics, paddings, paper, and foams.

An aqueous composition that is contacted with a fabric can be, for example, a fabric care composition (e.g., laundry detergent, fabric softener). Thus, a treatment method in certain embodiments can be considered a fabric care method or laundry method if employing a fabric care composition therein. A fabric care composition herein can effect one or more of the following fabric care benefits (i.e., surface substantive effects): wrinkle removal, wrinkle reduction, wrinkle resistance, fabric wear reduction, fabric wear resistance, fabric pilling reduction, fabric color maintenance, fabric color fading reduction, fabric color restoration, fabric soiling reduction, fabric soil release, fabric shape retention, fabric smoothness enhancement, anti-redeposition of soil on fabric, anti-greying of laundry, improved fabric hand/handle, and/or fabric shrinkage reduction.

Examples of conditions (e.g., time, temperature, wash/rinse volumes) for conducting a fabric care method or laundry method herein are disclosed in WO1997/003161 and U.S. Pat. Nos. 4,794,661, 4,580,421 and 5,945,394, which are incorporated herein by reference. In other examples, a material comprising fabric can be contacted with an aqueous composition herein: (i) for at least about 5, 10, 20, 30, 40, 50, 60, 70, 80, 90, 100, 110, or 120 minutes; (ii) at a temperature of at least about 10, 15, 20, 25, 30, 35, 40, 45, 50, 55, 60, 65, 70, 75, 80, 85, 90, or 95° C. (e.g., for laundry wash or rinse: a "cold" temperature of about 15-30° C., a "warm" temperature of about 30-50° C., a "hot" temperature of about 50-95° C.); (iii) at a pH of about 2, 3, 4, 5, 6, 7, 8, 9, 10, 11, or 12 (e.g., pH range of about 2-12, or about 3-11); (iv) at a salt (e.g., NaCl) concentration of at least about 0.5, 1.0, 1.5, 2.0, 2.5, 3.0, 3.5, or 4.0 wt %; or any combination of (i)-(iv).

The contacting step in a fabric care method or laundry method can comprise any of washing, soaking, and/or rinsing steps, for example. Contacting a material or fabric in still further embodiments can be performed by any means known in the art, such as dissolving, mixing, shaking, spraying, treating, immersing, flushing, pouring on or in, combining, painting, coating, applying, affixing to, and/or communicating an effective amount of a poly alpha-1,3-glucan ether compound herein with the fabric or material. In still further embodiments, contacting may be used to treat a fabric to provide a surface substantive effect. As used herein, the term "fabric hand" or "handle" refers to a person's tactile sensory response towards fabric which may be physical, physiological, psychological, social or any combination thereof. In one embodiment, the fabric hand may be measured using a PhabrOmeter® System for measuring relative hand value (available from Nu Cybertek, Inc. Davis, Calif.) (American Association of Textile Chemists and Colorists (AATCC test method "202-2012, Relative Hand Value of Textiles: Instrumental Method")).

In certain embodiments of treating a material comprising fabric, a poly alpha-1,3-glucan ether compound component(s) of the aqueous composition adsorbs to the fabric. This feature is believed to render poly alpha-1,3-glucan ether compounds (e.g., anionic glucan ether compounds such as carboxymethyl poly-alpha-1,3-glucan) useful as anti-redeposition agents and/or anti-greying agents in fabric care compositions disclosed herein (in addition to their viscosity-modifying effect). An anti-redeposition agent or anti-greying agent herein helps keep soil from redepositing onto clothing in wash water after the soil has been removed. Carboxymethyl cellulose (CMC) has typically been used as an anti-redeposition agent in laundry detergents. However, CMC is not stable to cellulase and is thus less useful in detergents containing cellulase (e.g., cellulase that has been directly added to detergent, and/or background cellulase activity associated with a different type of enzyme added to detergent). Poly alpha-1,3-glucan ether compounds, since they are both stable to cellulase and able to adsorb to fabric surfaces, are contemplated to be superior substitutes for CMC and other cellulose ether compounds in fabric care compositions containing cellulase. This superiority is also due in part to the cellulase-resistant viscosity-modifying effect of poly alpha-1,3-glucan ether compounds. It is further contemplated that adsorption of one or more poly alpha-1,3-glucan ether compounds herein to a fabric enhances mechanical properties of the fabric.

The below Examples demonstrate that poly alpha-1,3-glucan ether compounds such as carboxymethyl poly alpha-1,3-glucan adsorb to both natural (cotton, cretonne) and synthetic (polyester) fabrics, as well as a blend thereof (polyester/cretonne). This result is notable given that carboxymethyl cellulose (CMC) does not absorb to, or only poorly adsorbs to, polyester and polyester/cotton blends (see European Pat. Appl. Publ. No. EP0035478, for example). Thus, in certain embodiments of a treatment method herein, an anionic poly alpha-1,3-glucan ether compound (e.g., carboxyalkyl poly alpha-1,3-glucan such as carboxymethyl poly alpha-1,3-glucan) adsorbs to material comprising natural fiber (e.g. cotton) and/or synthetic fiber (e.g., polyester). Such adsorption of an anionic poly alpha-1,3-glucan ether compound can be at least about 20%, 30%, 40%, 50%, 60%, 70%, 80%, 90%, 100%, 120%, 140%, 160%, 180%, or 200% greater than the adsorption of the same glucan ether to a cotton fabric (e.g., cretonne), for example. Also, such adsorption may optionally be under conditions of about 1-3 or 1-4 wt % salt (e.g., NaCl), and/or a pH of about 3.0, 3.5, 4.0, 4.5, 5.0, 5.5, 6.0, 6.5, 7.0, 7.5, 8.0, 8.5, 9.0, or 9.5, for example.

Adsorption of a poly alpha-1,3-glucan ether compound to a fabric herein can be measured following the methodology disclosed in the below Examples, for example. Alternatively, adsorption can be measured using a colorimetric technique (e.g., Dubois et al., 1956, *Anal. Chem.* 28:350-356; Zemljič et al., 2006, *Lenzinger Berichte* 85:68-76; both incorporated herein by reference) or any other method known in the art.

Other materials that can be contacted in the above treatment method include surfaces that can be treated with a dish detergent (e.g., automatic dishwashing detergent or hand dish detergent). Examples of such materials include surfaces of dishes, glasses, pots, pans, baking dishes, utensils and flatware made from ceramic material, china, metal, glass, plastic (e.g., polyethylene, polypropylene, polystyrene, etc.) and wood (collectively referred to herein as "tableware"). Thus, the treatment method in certain embodiments can be considered a dishwashing method or tableware washing method, for example. Examples of conditions (e.g., time, temperature, wash volume) for conducting a dishwashing or tableware washing method herein are disclosed in U.S. Pat. No. 8,575,083, which is incorporated herein by reference. In other examples, a tableware article can be contacted with an aqueous composition herein under a suitable set of conditions such as any of those disclosed above with regard to contacting a fabric-comprising material.

Other materials that can be contacted in the above treatment method include oral surfaces such as any soft or hard surface within the oral cavity including surfaces of the tongue, hard and soft palate, buccal mucosa, gums and dental surfaces (e.g., natural tooth or a hard surface of artificial dentition such as a crown, cap, filling, bridge, denture, or dental implant). Thus, a treatment method in certain embodiments can be considered an oral care method or dental care method, for example. Conditions (e.g., time, temperature) for contacting an oral surface with an aqueous composition herein should be suitable for the intended purpose of making such contact. Other surfaces that can be contacted in a treatment method also include a surface of the integumentary system such as skin, hair or nails.

Thus, certain embodiments herein concern material (e.g., fabric) that comprises a poly alpha-1,3-glucan ether compound herein. Such material can be produced following a material treatment method as disclosed, for example. A material may comprise a glucan ether compound in certain embodiments if the compound is adsorbed to, or otherwise in contact with, the surface of the material.

Certain embodiments of a method of treating a material herein further comprise a drying step, in which a material is dried after being contacted with the aqueous composition. A drying step can be performed directly after the contacting step, or following one or more additional steps that might follow the contacting step (e.g., drying of a fabric after being rinsed, in water for example, following a wash in an aqueous composition herein). Drying can be performed by any of several means known in the art, such as air drying (e.g., ~20-25° C.), or at a temperature of at least about 30, 40, 50, 60, 70, 80, 90, 100, 120, 140, 160, 170, 175, 180, or 200° C., for example. A material that has been dried herein typically has less than 3, 2, 1, 0.5, or 0.1 wt % water comprised therein. Fabric is a preferred material for conducting an optional drying step.

An aqueous composition used in a treatment method herein can be any aqueous composition disclosed herein, such as in the above embodiments or in the below Examples. Thus, the cellulase and poly alpha-1,3-glucan ether components of an aqueous composition can be any as disclosed herein. Examples of aqueous compositions are detergents (e.g., laundry detergent or dish detergent) and water-containing dentifrices such as toothpaste.

The embodiments disclosed above comprise one or more cellulase enzymes. In alternative embodiments, any of the above compositions or methods can lack a cellulase enzyme or can comprise no added cellulase enzyme.

Poly alpha-1,3-glucan ether compounds useful for preparing compositions disclosed herein can be prepared as disclosed in U.S. Appl. Publ. No. 2014/0179913 (incorporated herein by reference), for example. In addition, poly alpha-1,3-glucan ether compounds herein can be produced by a method comprising: contacting poly alpha-1,3-glucan in a reaction under alkaline conditions with at least one etherification agent comprising an organic group, wherein the organic group is etherified to the poly alpha-1,3-glucan thereby producing a poly alpha-1,3-glucan ether compound represented by the structure:

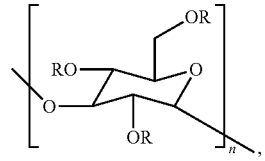

wherein
(i) n is at least 6,
(ii) each R is independently an H or an organic group, and
(iii) the compound has a degree of substitution with the organic group of about 0.05 to about 3.0.

A poly alpha-1,3-glucan ether produced by this method can optionally be isolated. This method can be considered to comprise an etherification reaction.

The following steps can be taken to prepare the above etherification reaction. Poly alpha-1,3-glucan can be contacted with a solvent and one or more alkali hydroxides to provide a solution or mixture. The alkaline conditions of the reaction can thus comprise an alkali hydroxide solution. The pH of the alkaline conditions can be at least about 11.0, 11.2, 11.4, 11.6, 11.8, 12.0, 12.2, 12.4, 12.6, 12.8, or 13.0.

Various alkali hydroxides can be used, such as sodium hydroxide, potassium hydroxide, calcium hydroxide, lithium hydroxide, and/or tetraethylammonium hydroxide. The concentration of alkali hydroxide in a preparation with poly alpha-1,3-glucan and a solvent can be from about 1-70 wt %, 5-50 wt %, 10-50 wt %, 10-40 wt %, or 10-30 wt % (or any integer between 1 and 70 wt %). Alternatively, the concentration of alkali hydroxide such as sodium hydroxide can be at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 wt %. An alkali hydroxide used to prepare alkaline conditions may be in a completely aqueous solution or an aqueous solution comprising one or more water-soluble organic solvents such as ethanol or isopropanol. Alternatively, an alkali hydroxide can be added as a solid to provide alkaline conditions.

Various organic solvents that can optionally be included when preparing the reaction include alcohols, acetone, dioxane, isopropanol and toluene, for example; none of these solvents dissolve poly alpha-1,3-glucan. Toluene or isopropanol can be used in certain embodiments. An organic solvent can be added before or after addition of alkali hydroxide. The concentration of an organic solvent (e.g., isopropanol or toluene) in a preparation comprising poly alpha-1,3-glucan and an alkali hydroxide can be at least about 10, 15, 20, 25, 30, 35, 40, 45, 50, 55, 60, 65, 70, 75, 80, 85, or 90 wt % (or any integer between 10 and 90 wt %).

Alternatively, solvents that can dissolve poly alpha-1,3-glucan can be used when preparing the reaction. These solvents include, but are not limited to, lithium chloride (LiCl)/N,N-dimethyl-acetamide (DMAc), $SO_2$/diethylamine (DEA)/climethyl sulfoxide (DMSO), LiCl/1,3-dimethy-2-imidazolidinone (DMI), N,N-dimethylformamide (DMF)/$N_2O_4$, DMSO/tetrabutyl-ammonium fluoride trihydrate (TBAF), N-methylmorpholine-N-oxide (NMMO), Ni(tren)$(OH)_2$ [tren¼tris(2-aminoethyl)amine] aqueous solutions and melts of $LiClO_4 \cdot 3 H_2O$, NaOH/urea aqueous solutions, aqueous sodium hydroxide, aqueous potassium hydroxide, formic acid, and ionic liquids.

Poly alpha-1,3-glucan can be contacted with a solvent and one or more alkali hydroxides by mixing. Such mixing can be performed during or after adding these components with each other. Mixing can be performed by manual mixing, mixing using an overhead mixer, using a magnetic stir bar, or shaking, for example. In certain embodiments, poly alpha-1,3-glucan can first be mixed in water or an aqueous solution before it is mixed with a solvent and/or alkali hydroxide.

After contacting poly alpha-1,3-glucan, solvent, and one or more alkali hydroxides with each other, the resulting composition can optionally be maintained at ambient temperature for up to 14 days. The term "ambient temperature" as used herein refers to a temperature between about 15-30° C. or 20-25° C. (or any integer between 15 and 30° C.). Alternatively, the composition can be heated with or without reflux at a temperature from about 30° C. to about 150° C. (or any integer between 30 and 150° C.) for up to about 48 hours. The composition in certain embodiments can be heated at about 55° C. for about 30 minutes or 60 minutes. Thus, a composition obtained from mixing a poly alpha-1,3-glucan, solvent, and one or more alkali hydroxides with each other can be heated at about 50, 51, 52, 53, 54, 55, 56, 57, 58, 59, or 60° C. for about 30-90 minutes.

After contacting poly alpha-1,3-glucan, solvent, and one or more alkali hydroxides with each other, the resulting composition can optionally be filtered (with or without applying a temperature treatment step). Such filtration can be performed using a funnel, centrifuge, press filter, or any other method and/or equipment known in the art that allows removal of liquids from solids. Though filtration would remove much of the alkali hydroxide, the filtered poly alpha-1,3-glucan would remain alkaline (i.e., mercerized poly alpha-1,3-glucan), thereby providing alkaline conditions.

An etherification agent comprising an organic group can be contacted with poly alpha-1,3-glucan in a reaction under alkaline conditions in a method herein of producing poly alpha-1,3-glucan ether compounds. For example, an etherification agent can be added to a composition prepared by contacting poly alpha-1,3-glucan, solvent, and one or more alkali hydroxides with each other as described above. Alternatively, an etherification agent can be included when preparing the alkaline conditions (e.g., an etherification agent can be mixed with poly alpha-1,3-glucan and solvent before mixing with alkali hydroxide).

An etherification agent herein refers to an agent that can be used to etherify one or more hydroxyl groups of the glucose units of poly alpha-1,3-glucan with an organic group as defined above. Examples of such organic groups include alkyl groups, hydroxy alkyl groups, and carboxy alkyl groups. One or more etherification agents may be used in the reaction.

Etherification agents suitable for preparing an alkyl poly alpha-1,3-glucan ether compound include, for example, dialkyl sulfates, dialkyl carbonates, alkyl halides (e.g., alkyl chloride), iodoalkanes, alkyl triflates (alkyl trifluoromethanesulfonates) and alkyl fluorosulfonates. Thus, examples of etherification agents for producing methyl poly alpha-1,3-glucan ethers include dimethyl sulfate, dimethyl carbonate, methyl chloride, iodomethane, methyl triflate and methyl fluorosulfonate. Examples of etherification agents for producing ethyl poly alpha-1,3-glucan ethers include diethyl sulfate, diethyl carbonate, ethyl chloride, iodoethane, ethyl triflate and ethyl fluorosulfonate. Examples of etherification agents for producing propyl poly alpha-1,3-glucan ethers include dipropyl sulfate, dipropyl carbonate, propyl chloride, iodopropane, propyl triflate and propyl fluorosulfonate. Examples of etherification agents for producing butyl poly alpha-1,3-glucan ethers include dibutyl sulfate, dibutyl carbonate, butyl chloride, iodobutane and butyl triflate.

Etherification agents suitable for preparing a hydroxyalkyl poly alpha-1,3-glucan ether compound include, for example, alkylene oxides such as ethylene oxide, propylene oxide (e.g., 1,2-propylene oxide), butylene oxide (e.g., 1,2-butylene oxide; 2,3-butylene oxide; 1,4-butylene oxide), or combinations thereof. As examples, propylene oxide can be used as an etherification agent for preparing hydroxypropyl poly alpha-1,3-glucan, and ethylene oxide can be used as an etherification agent for preparing hydroxyethyl poly alpha-1,3-glucan. Alternatively, hydroxyalkyl halides (e.g., hydroxyalkyl chloride) can be used as etherification agents for preparing hydroxyalkyl poly alpha-1,3-glucan. Examples of hydroxyalkyl halides include hydroxyethyl halide, hydroxypropyl halide (e.g., 2-hydroxypropyl chloride, 3-hydroxypropyl chloride) and hydroxybutyl halide. Alternatively, alkylene chlorohydrins can be used as etherification agents for preparing hydroxyalkyl poly alpha-1,3-glucan. Alkylene chlorohydrins that can be used include, but are not limited to, ethylene chlorohydrin, propylene chlorohydrin, butylene chlorohydrin, or combinations of these.

Etherification agents suitable for preparing a dihydroxyalkyl poly alpha-1,3-glucan ether compound include dihydroxyalkyl halides (e.g., dihydroxyalkyl chloride) such as dihydroxyethyl halide, dihydroxypropyl halide (e.g., 2,3-dihydroxypropyl chloride [i.e., 3-chloro-1,2-propanediol]), or dihydroxybutyl halide, for example. 2,3-dihydroxypropyl chloride can be used to prepare dihydroxypropyl poly alpha-1,3-glucan, for example.

Etherification agents suitable for preparing a carboxyalkyl poly alpha-1,3-glucan ether compound may include haloalkylates (e.g., chloroalkylate). Examples of haloalkylates include haloacetate (e.g., chloroacetate), 3-halopropionate (e.g., 3-chloropropionate) and 4-halobutyrate (e.g., 4-chlorobutyrate). For example, chloroacetate (monochloroacetate) (e.g., sodium chloroacetate or chloroacetic acid) can be used as an etherification agent to prepare carboxymethyl poly alpha-1,3-glucan.

When producing a poly alpha-1,3-glucan ether compound with two or more different organic groups, two or more different etherification agents would be used, accordingly.

For example, both an alkylene oxide and an alkyl chloride could be used as etherification agents to produce an alkyl hydroxyalkyl poly alpha-1,3-glucan ether. Any of the etherification agents disclosed herein may therefore be combined to produce poly alpha-1,3-glucan ether compounds with two or more different organic groups. Such two or more etherification agents may be used in the reaction at the same time, or may be used sequentially in the reaction. When used sequentially, any of the temperature-treatment (e.g., heating) steps disclosed below may optionally be used between each addition. One may choose sequential introduction of etherification agents in order to control the desired DoS of each organic group. In general, a particular etherification agent would be used first if the organic group it forms in the ether product is desired at a higher DoS compared to the DoS of another organic group to be added.

The amount of etherification agent to be contacted with poly alpha-1,3-glucan in a reaction under alkaline conditions can be determined based on the degree of substitution required in the poly alpha-1,3-glucan ether compound being produced. The amount of ether substitution groups on each monomeric unit in poly alpha-1,3-glucan ether compounds produced herein can be determined using nuclear magnetic resonance (NMR) spectroscopy. The molar substitution (MS) value for poly alpha-1,3-glucan has no upper limit. In general, an etherification agent can be used in a quantity of at least about 0.05 mole per mole of poly alpha-1,3-glucan. There is no upper limit to the quantity of etherification agent that can be used.

Reactions for producing poly alpha-1,3-glucan ether compounds herein can optionally be carried out in a pressure vessel such as a Parr reactor, an autoclave, a shaker tube or any other pressure vessel well known in the art. A shaker tube is used to perform the reaction in certain embodiments.

A reaction herein can optionally be heated following the step of contacting poly alpha-1,3-glucan with an etherification agent under alkaline conditions. The reaction temperatures and time of applying such temperatures can be varied within wide limits. For example, a reaction can optionally be maintained at ambient temperature for up to 14 days. Alternatively, a reaction can be heated, with or without reflux, between about 25° C. to about 200° C. (or any integer between 25 and 200° C.). Reaction time can be varied correspondingly: more time at a low temperature and less time at a high temperature.

Optionally, a reaction herein can be maintained under an inert gas, with or without heating. As used herein, the term "inert gas" refers to a gas which does not undergo chemical reactions under a set of given conditions, such as those disclosed for preparing a reaction herein.

All of the components of the reactions disclosed herein can be mixed together at the same time and brought to the desired reaction temperature, whereupon the temperature is maintained with or without stirring until the desired poly alpha-1,3-glucan ether compound is formed. Alternatively, the mixed components can be left at ambient temperature as described above.

Following etherification, the pH of a reaction can be neutralized. Neutralization of a reaction can be performed using one or more acids. The term "neutral pH" as used herein, refers to a pH that is neither substantially acidic or basic (e.g., a pH of about 6-8, or about 6.0, 6.2, 6.4, 6.6, 6.8, 7.0, 7.2, 7.4, 7.6, 7.8, or 8.0). Various acids that can be used for this purpose include, but are not limited to, sulfuric, acetic, hydrochloric, nitric, any mineral (inorganic) acid, any organic acid, or any combination of these acids.

A poly alpha-1,3-glucan ether compound produced in a reaction herein can optionally be washed one or more times with a liquid that does not readily dissolve the compound. For example, poly alpha-1,3-glucan ether can be washed with water, alcohol, acetone, aromatics, or any combination of these, depending on the solubility of the ether compound therein (where lack of solubility is desirable for washing). In general, a solvent comprising an organic solvent such as alcohol is preferred for washing a poly alpha-1,3-glucan ether. A poly alpha-1,3-glucan ether product can be washed one or more times with an aqueous solution containing methanol or ethanol, for example. For example, 70-95 wt % ethanol can be used to wash the product. A poly alpha-1,3-glucan ether product can be washed with a methanol:acetone (e.g., 60:40) solution in another embodiment. Hot water (about 95-100° C.) can be used in certain embodiments, such as for washing alkyl poly alpha-1,3-glucan ethers (e.g., ethyl poly alpha-1,3-glucan) and alkyl hydroxyalkyl poly alpha-1,3-glucan ethers (e.g., ethyl hydroxyethyl poly alpha-1,3-glucan).

A poly alpha-1,3-glucan ether produced in the disclosed reaction can be isolated. This step can be performed before or after neutralization and/or washing steps using a funnel, centrifuge, press filter, or any other method or equipment known in the art that allows removal of liquids from solids. For example, a Buchner funnel may be used to isolate a poly alpha-1,3-glucan ether product. An isolated poly alpha-1,3-glucan ether product can be dried using any method known in the art, such as vacuum drying, air drying, or freeze drying.

Any of the above etherification reactions can be repeated using a poly alpha-1,3-glucan ether product as the starting material for further modification. This approach may be suitable for increasing the DoS of an organic group, and/or adding one or more different organic groups to the ether product.

The structure, molecular weight and degree of substitution of a poly alpha-1,3-glucan ether product can be confirmed using various physiochemical analyses known in the art such as NMR spectroscopy and size exclusion chromatography (SEC).

The percentage of glycosidic linkages between the glucose monomer units of poly alpha-1,3-glucan used to prepare poly alpha-1,3-glucan ether compounds herein that are alpha-1,3 is at least about 50%, 60%, 70%, 80%, 90%, 95%, 96%, 97%, 98%, 99%, or 100% (or any integer value between 50% and 100%). In such embodiments, accordingly, poly alpha-1,3-glucan has less than about 50%, 40%, 30%, 20%, 10%, 5%, 4%, 3%, 2%, 1%, or 0% (or any integer value between 0% and 50%) of glycosidic linkages that are not alpha-1,3.

Poly alpha-1,3-glucan used to prepare poly alpha-1,3-glucan ether compounds herein is preferably linear/unbranched. In certain embodiments, poly alpha-1,3-glucan has no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points.

The $M_n$ or $M_w$ of poly alpha-1,3-glucan used to prepare poly alpha-1,3-glucan ether compounds herein may be at least about 1000 to about 600000. Alternatively still, $M_n$ or $M_w$ can be at least about 2000, 3000, 4000, 5000, 6000, 7000, 8000, 9000, 10000, 15000, 20000, 25000, 30000, 35000, 40000, 45000, 50000, 75000, 100000, 150000, 200000, 250000, 300000, 350000, 400000, 450000, 500000, 550000, or 600000 (or any integer between 2000 and 600000), for example.

Poly alpha-1,3-glucan used for preparing poly alpha-1,3-glucan ether compounds herein can be enzymatically produced from sucrose using one or more glucosyltransferase (gtf) enzymes. The poly alpha-1,3-glucan product of this enzymatic reaction can be purified before using it to prepare an ether using the disclosed process. Alternatively, a poly alpha-1,3-glucan product of a gtf reaction can be used with little or no processing for preparing poly alpha-1,3-glucan ether compounds.

A poly alpha-1,3-glucan slurry can be used directly in any of the above processes for producing a poly alpha-1,3-glucan ether compound disclosed herein. As used herein, a "poly alpha-1,3-glucan slurry" refers to a mixture comprising the components of a gtf enzymatic reaction. A gtf enzymatic reaction can include, in addition to poly alpha-1,3-glucan itself, various components such as sucrose, one or more gtf enzymes, glucose, fructose, leucrose, buffer, FermaSure®, soluble oligosaccharides, oligosaccharide primers, bacterial enzyme extract components, borates, sodium hydroxide, hydrochloric acid, cell lysate, proteins and/or nucleic acids. Minimally, the components of a gtf enzymatic reaction can include, in addition to poly alpha-1,3-glucan itself, sucrose, one or more gtf enzymes, glucose, and fructose, for example. In another example, the components of a gtf enzymatic reaction can include, in addition to poly alpha-1,3-glucan itself, sucrose, one or more gtf enzymes, glucose, fructose, leucrose and soluble oligosaccharides (and optionally bacterial enzyme extract components). It should be apparent that poly alpha-1,3-glucan, when in a slurry as disclosed herein, has not been purified or washed. It should also be apparent that a slurry represents a gtf enzymatic reaction that is complete or for which an observable amount of poly alpha-1,3-glucan has been produced, which forms a solid since it is insoluble in the aqueous reaction milieu (has pH of 5-7, for example). A poly alpha-1,3-glucan slurry can be prepared by setting up a gtf reaction as disclosed in U.S. Pat. No. 7,000,000 or U.S. Patent Appl. Publ. Nos. 2013/0244288 and 2013/0244287, for example, all of which are incorporated herein by reference. A poly alpha-1,3-glucan slurry can be entered, for example, into a reaction for producing a carboxyalkyl poly alpha-1,3-glucan such as carboxymethyl poly alpha-1,3-glucan. Some embodiments herein are drawn to compositions comprising poly alpha-1,3-glucan ether and a glucosyltransferase enzyme (e.g., such a composition may result when using a slurry in an etherification reaction herein).

Alternatively, a wet cake of poly alpha-1,3-glucan can be used directly in any of the above processes for producing a poly alpha-1,3-glucan ether compound disclosed herein. A "wet cake of poly alpha-1,3-glucan" as used herein refers to poly alpha-1,3-glucan that has been separated (e.g., filtered) from a slurry and washed with water or an aqueous solution. A wet cake can be washed at least 1, 2, 3, 4, 5, or more times, for example. The poly alpha-1,3-glucan is not dried when preparing a wet cake. A wet cake is termed as "wet" given the retention of water by the washed poly alpha-1,3-glucan.

A wet cake of poly alpha-1,3-glucan can be prepared using any device known in the art for separating solids from liquids, such as a filter or centrifuge. For example, poly alpha-1,3-glucan solids in a slurry can be collected on a Buchner funnel using a mesh screen over filter paper. Filtered wet cake can be resuspended in water (e.g., deionized water) and filtered one or more times to remove soluble components of the slurry such as sucrose, fructose and leucrose. As another example for preparing a wet cake, poly alpha-1,3-glucan solids from a slurry can be collected as a pellet via centrifugation, resuspended in water (e.g., deionized water), and re-pelleted and resuspended one or more additional times. A poly alpha-1,3-glucan wet cake can be entered into a reaction for producing any ether compound herein, such as carboxyalkyl poly alpha-1,3-glucan (e.g., carboxymethyl poly alpha-1,3-glucan).

Poly alpha-1,3-glucan ether compounds disclosed herein may be crosslinked using any means known in the art. Such crosslinkage may be between the same poly alpha-1,3-glucan ether compounds, or between two or more different poly alpha-1,3-glucan ether compounds. Also, crosslinkage may be intermolecular and/or intramolecular.

A crosslinked poly alpha-1,3-glucan ether compound can be prepared as follows, for example. One or more poly alpha-1,3-glucan ether compounds can be dissolved in water or an aqueous solution to prepare a 0.2, 0.5, 1, 2, 3, 4, 5, 6, 7, 8, 9, or 10 wt % solution of the ether compound(s). Poly alpha-1,3-glucan ether compound(s) can be dissolved or mixed using any process known in the art, such as by increasing temperature, manual mixing, and/or homogenization (as described above).

A crosslinking agent is next dissolved in the poly alpha-1,3-glucan ether solution or mixture. The concentration of the crosslinking agent in the resulting solution can be about 0.2 to 20 wt %, or about 0.1, 0.2, 0.3, 0.4, 0.5, 1, 2, 3, 4, 5, 6, 7, 8, 9, 10, 15, or 20 wt %.

Examples of suitable crosslinking agents are boron-containing compounds and polyvalent metals such as titanium or zirconium. Boron-containing compounds include boric acid, diborates, tetraborates, pentaborates, polymeric compounds such as Polybor®, polymeric compounds of boric acid, and alkali borates, for example. These agents can be used to produce borate crosslinks between poly alpha-1,3-glucan ether molecules. Titanium crosslinks may be produced using titanium IV-containing compounds (e.g., titanium ammonium lactate, titanium triethanolamine, titanium acetylacetonate, polyhydroxy complexes of titanium) as crosslinking agents. Zirconium crosslinks can be produced using zirconium IV-containing compounds (e.g., zirconium lactate, zirconium carbonate, zirconium acetylacetonate, zirconium triethanolamine, zirconium diisopropylamine lactate, polyhydroxy complexes of zirconium) as crosslinking agents. Other examples of crosslinking agents useful herein are described in U.S. Pat. Nos. 4,462,917, 4,464,270, 4,477,360 and 4,799,550, which are all incorporated herein by reference.

The pH of the solution or mixture containing both a crosslinking agent(s) and a poly alpha-1,3-glucan ether compound(s) can be adjusted to be alkali (e.g., pH of 8, 8.5, 9, 9.5, or 10). Modification of pH can be done by any means known in the art, such as with a concentrated aqueous solution of an alkali hydroxide such as sodium hydroxide. Dissolving a crosslinking agent in a solution or mixture containing one or more poly alpha-1,3-glucan ether compounds at an alkali pH results in crosslinking of the poly alpha-1,3-glucan ether compound(s).

Non-limiting examples of compositions and methods disclosed herein include:

1. A composition comprising a cellulase and a poly alpha-1,3-glucan ether compound represented by the structure:

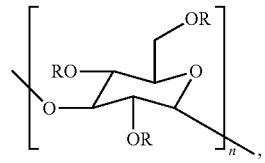

wherein
(i) n is at least 6,
(ii) each R is independently an H or an organic group, and
(iii) the compound has a degree of substitution of about 0.05 to about 3.0.
2. The composition of embodiment 1, wherein at least one organic group is selected from the group consisting of carboxy alkyl group, hydroxy alkyl group, and alkyl group.
3. The composition of embodiment 2, wherein at least one organic group is selected from the group consisting of carboxymethyl, hydroxypropyl, dihydroxypropyl, hydroxyethyl, methyl, and ethyl group.
4. The composition of embodiment 2, wherein the organic group is a carboxymethyl group.
5. The composition of embodiment 1, 2, 3, or 4, wherein the composition is in the form of a personal care product, household product, or industrial product.
6. The composition of embodiment 5, wherein the composition is a fabric care product.
7. The composition of embodiment 1, 2, 3, 4, 5, or 6, wherein the composition is an aqueous composition.
8. The composition of embodiment 7, wherein the composition has a viscosity of at least about 10 cPs.
9. A method for preparing an aqueous composition, the method comprising: contacting an aqueous composition with a poly alpha-1,3-glucan ether compound represented by the structure:

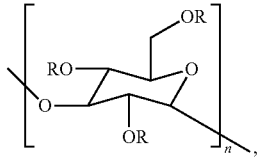

wherein
(i) n is at least 6,
(ii) each R is independently an H or an organic group, and
(iii) the compound has a degree of substitution of about 0.05 to about 3.0;
and wherein the aqueous composition prepared in the method comprises a cellulase.
10. The method of embodiment 9, wherein the cellulase is:
(i) comprised in the aqueous composition prior to the contacting step, or
(ii) added to the aqueous composition during or after the contacting step.
11. The method of embodiment 9 or 10, wherein:
(i) the viscosity of the aqueous composition is increased by the poly alpha-1,3-glucan ether compound, and/or
(ii) the shear thinning behavior or the shear thickening behavior of the aqueous composition is increased by the poly alpha-1,3-glucan ether compound.
12. A method of treating a material, the method comprising: contacting a material with an aqueous composition comprising a cellulase and a poly alpha-1,3-glucan ether compound represented by the structure:

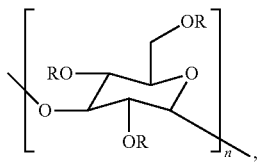

wherein
(i) n is at least 6,
(ii) each R is independently an H or an organic group, and
(iii) the compound has a degree of substitution of about 0.05 to about 3.0.
13. The method of embodiment 12, wherein the material comprises fabric.
14. The method of embodiment 13 wherein the fabric comprises a (i) natural fiber, (ii) synthetic fiber, or a combination of both (i) and (ii).
15. The method of embodiment 13 or 14, wherein the poly alpha-1,3-glucan ether compound adsorbs to the fabric.

EXAMPLES

The present disclosure is further exemplified in the following Examples. It should be understood that these Examples, while indicating certain preferred aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

Abbreviations

The meaning of some of the abbreviations used herein is as follows: "g" means gram(s), "h" means hour(s), "mL" means milliliter(s), "psi" means pound(s) per square inch, "wt %" means weight percentage, "μm" means micrometer(s), "° C." means degrees Celsius, "mg" means milligram(s), "mm" means millimeter(s), "m" means meter(s), "μL" means microliter(s), "mmol" means millimole(s), "min" means minute(s), "mol %" means mole percent, "M" means molar, "rpm" means revolutions per minute, "MPa" means megaPascals, "CMG" means carboxymethyl glucan, and "CMC" means carboxymethyl cellulose.

General Methods

All reagents were obtained from Sigma-Aldrich (St. Louis, Mo.) unless stated otherwise. Carboxymethyl cellulose ether derivative (CMC, Sigma-Aldrich product no. 419273) had a $M_w$ of about 90000 and a degree of substitution (DoS) of 0.7 carboxymethyl groups per glucose unit. PREFERENZ S100 amylase, PURASTAR ST L amylase, PURADAX HA1200E cellulase and PURADAX EG L cellulase were from DuPont Industrial Biosciences.

Preparation of Poly Alpha-1,3-Glucan

Poly alpha-1,3-glucan was prepared using a gtfJ enzyme preparation as described in U.S. Patent Appl. Publ. No. 2013/0244288, which is incorporated herein by reference in its entirety.

Preparation of Sodium Carboxymethyl Poly Alpha-1,3-Glucan 10 g of poly alpha-1,3-glucan ($M_w$ [weight-average molecular weight]=236,854) was added to 200 mL of isopropanol in a 500-mL capacity round bottom flask fitted with a thermocouple for temperature monitoring and a condenser connected to a recirculating bath, and a magnetic stir bar. 40 mL of sodium hydroxide (15% solution) was added dropwise to the preparation, which was then heated to 25° C. on a hotplate. The preparation was stirred for 1 hour before the temperature was increased to 55° C. Sodium chloroacetate (12 g) was then added to provide a reaction, which was held at 55° C. for 3 hours before being neutralized with 90% acetic acid. The solid thus formed was collected by vacuum filtration and washed with ethanol (70%) four times, dried under vacuum at 20-25° C., and analyzed by NMR and SEC to determine molecular weight and DoS. The solid material obtained was identified as water-soluble sodium carboxymethyl poly alpha-1,3-glucan with a DoS of 0.5 and an $M_w$ of 580,000.

Table 1 provides a list of DoS measurements for various samples of carboxymethyl poly alpha-1,3-glucan prepared using the above method. The poly alpha-1,3-glucan starting material had various molecular weights (Table 1).

TABLE 1

DoS of Carboxymethyl Poly Alpha-1,3-Glucan Prepared from Poly Alpha-1,3-Glucan

| CMG Sample Designation | $M_w$ of poly alpha-1,3-glucan starting material | DoS |
| --- | --- | --- |
| 1A (35) | 140287 | 0.5 |
| 1B (36) | 140287 | 0.9 |
| 1C (39) | 140287 | 1 |
| 1D (44) | 88445 | 0.7 |
| 1E (47) | 278858 | 0.7 |
| 1F (58) | 248006 | |
| 1G (67) | 236854 | 0.5 |
| 1H (72) | 236854 | 0.9 |
| 1I (−41) | 200000 | 0.5 |
| 1J (−39) | 168584 | 0.5 |
| D102709-44 | 98133 | 0.47 |

Preparation of Potassium/Sodium Carboxymethyl Poly Alpha-1,3-Glucan 10 g of poly alpha-1,3-glucan ($M_w$=168,000) was added to 200 mL of isopropanol in a 500-mL capacity round bottom flask fitted with a thermocouple for temperature monitoring and a condenser connected to a recirculating bath, and a magnetic stir bar. 40 mL of potassium hydroxide (15% solution) was added dropwise to this preparation, which was then heated to 25° C. on a hotplate. The preparation was stirred for 1 hour before the temperature was increased to 55° C. Sodium chloroacetate (12 g) was then added to provide a reaction, which was held at 55° C. for 3 hours before being neutralized with 90% acetic acid. The solid thus formed was collected by vacuum filtration and washed with ethanol (70%) four times, dried under vacuum at 20-25° C., and analyzed by NMR and SEC to determine molecular weight and DoS. The solid material obtained was identified as water soluble potassium/sodium carboxymethyl poly alpha-1,3-glucan with a DoS of 0.77. This procedure could be adapted to produce potassium carboxymethyl poly alpha-1,3-glucan by simply using chloroacetic acid, instead of sodium chloroacetate, as the etherification agent.

Preparation of Lithium/Sodium Carboxymethyl Poly Alpha-1,3-Glucan 10 g of poly alpha-1,3-glucan ($M_w$=168,000) was added to 200 mL of isopropanol in a 500-mL capacity round bottom flask fitted with a thermocouple for temperature monitoring and a condenser connected to a recirculating bath, and a magnetic stir bar. 50 mL of lithium hydroxide (11.3% solution) was added dropwise to this preparation, which was then heated to 25° C. on a hotplate. The preparation was stirred for 1 hour before the temperature was increased to 55° C. Sodium chloroacetate (12 g) was then added to provide a reaction, which was held at 55° C. for 3 hours before being neutralized with 90% acetic acid. The solid thus formed was collected by vacuum filtration and washed with ethanol (70%) four times, dried under vacuum at 20-25° C., and analyzed by NMR and SEC to determine molecular weight and DoS. The solid material obtained was identified as water soluble CMG with a DoS of 0.79 (sample 2A). Reagent amounts were adjusted to prepare another CMG sample, which had a DoS of 0.36 (sample 2B). This procedure could be adapted to produce lithium carboxymethyl poly alpha-1,3-glucan by simply using chloroacetic acid, instead of sodium chloroacetate, as the etherification agent.

Preparation of Carboxymethyl Poly Alpha-1,3-Glucan from Poly Alpha-1,3-Glucan Slurry Poly alpha-1,3-glucan slurry (500 g, see below) was placed in a 1-L jacketed reaction vessel fitted with a thermocouple for temperature monitoring, a condenser connected to a recirculating bath, and a magnetic stir bar. Solid sodium hydroxide (75 g) was added to the slurry to yield a preparation with 15 wt % sodium hydroxide. This preparation was heated to 25° C. on a hotplate. The preparation was then stirred for 1 hour before the temperature was increased to 55° C. Sodium chloroacetate (227.3 g) was added to the preparation and the reaction temperature was held at 55° C. for 3 hours. The reaction was then neutralized with acetic acid (90%). The solid was collected by vacuum filtration and washed with ethanol (70%) four times, dried under vacuum at 20-25° C., and analyzed by NMR and SEC to determine molecular weight and DoS. The solid material obtained was identified as water-soluble carboxymethyl poly alpha-1,3-glucan with a DoS of 0.3 and a $M_w$ of 140,000.

Preparation of Carboxymethyl Poly Alpha-1,3-Glucan from Poly Alpha-1,3-Glucan Wet Cake Poly alpha-1,3-glucan wet cake (500 g, see below) was placed in a 1-L jacketed reaction vessel fitted with a thermocouple for temperature monitoring, a condenser connected to a recirculating bath, and an overhead stirrer. Isopropanol (500 mL) and solid sodium hydroxide (79.1 g) were added to the wet cake to yield a preparation with 15 wt % sodium hydroxide. This preparation was heated to 25° C. on a hotplate, and then stirred for 1 hour before the temperature was increased to 55° C. Sodium chloroacetate (227.3 g) was added to the preparation and the reaction temperature was held at 55° C. for 3 hours. The reaction was then neutralized with acetic acid (90%). The solids were collected by vacuum filtration and washed with ethanol (70%) four times, dried under vacuum at 20-25° C., and analyzed by NMR and SEC to determine molecular weight and DoS. The solid material obtained was identified as water-soluble carboxymethyl poly alpha-1,3-glucan with a DoS of 0.7 and a $M_w$ of 250,000.

Preparation of Hydroxypropyl Poly Alpha-1,3-Glucan (HPG)

10 g of poly alpha-1,3-glucan (number-average molecular weight [$M_e$]=71127) was mixed with 101 g of toluene and 5 mL of 20% sodium hydroxide. This preparation was stirred in a 500-mL glass beaker on a magnetic stir plate at 55° C. for 30 minutes. The preparation was then transferred to a shaker tube reactor after which 34 g of propylene oxide was added; the reaction was then stirred at 75° C. for 3 hours. The reaction was then neutralized with 20 g of acetic acid and the hydroxypropyl poly alpha-1,3-glucan solids thus formed were filtered with a Buchner funnel. The solids were then washed in a beaker with 70% ethanol and dried in a vacuum oven with a slight nitrogen bleed until constant dryness was achieved. The molar substitution (MS) of the dried product was reported by NMR to be 3.89 (sample 1).

An additional sample of HPG was produced following another method. 10 g of poly alpha-1,3-glucan ($M_w$=168584) was added to 101 mL of toluene and 5 mL of 20 wt % sodium hydroxide in a 400-mL beaker with a magnetic stir bar. The beaker was stirred on a magnetic stir plate at 375 rpm for one hour at 55° C. This preparation was then placed in a 200-mL capacity jar with a lid and allowed to sit overnight before being transferred to a 250-mL capacity shaker tube reactor. The reactor was heated to 75° C. and charged with 34 g of 1,2-propylene oxide. The reaction was held at temperature for 4 hours. After cooling, the reaction was neutralized with 90% acetic acid. The solid was collected by vacuum filtration, washed with hot water three times, dried under vacuum at 20-25° C., and analyzed by NMR to determine DoS. The solid material was determined to be HPG (sample 2).

Preparation of a Dihydroxypropyl Poly Alpha-1,3-Glucan 10 g of poly alpha-1,3-glucan ($M_w$=138,438) was added to 100 mL of 20% tetraethylammonium hydroxide in a 500-mL capacity round bottom flask fitted with a thermocouple for temperature monitoring and a condenser connected to a recirculating bath, and a magnetic stir bar (resulting in ~9.1 wt % poly alpha-1,3-glucan). This preparation was stirred and heated to 30° C. on a hotplate. The preparation was stirred for 1 hour to dissolve the solid before the temperature was increased to 55° C. 3-chloro-1,2-propanediol (6.7 g) and 11 g of DI water were then added to provide a reaction (containing ~5.2 wt % 3-chloro-1,2-propanediol), which was held at 55° C. for 1.5 hours afterwhich time 5.6 g of DI water was added to the reaction. The reaction was held at 55° C. for an additional 3 hours and 45 minutes before being neutralized with acetic acid. After neutralization, an excess of isopropanol was added to precipitate a solid. The solid thus formed was collected by vacuum filtration and washed with ethanol (95%) four times, and dried under vacuum at 20-25° C. The solid material obtained was identified as dihydroxypropyl poly alpha-1,3-glucan that was not water soluble, and having a degree of substitution of 0.6.

The above procedure was repeated with some modification, and this time using a sample of the dihydroxypropyl poly alpha-1,3-glucan prepared above as the starting material. Briefly, 5 g of the glucan ether was added to 50 mL of 20% tetraethylammonium hydroxide. This preparation was stirred with a magnetic stir bar until the solid dissolved, and then heated to 30° C. for 1 hour on a hotplate. The preparation was then heated to 55° C. and 3-chloro-1,2-propanediol (8 g) was added to provide a reaction. The reaction was then stirred for 2 hours, afterwhich time it was neutralized with acetic acid. After neutralization, an excess of isopropanol was added to precipitate a solid. The solid thus formed was collected by vacuum filtration and washed with ethanol (95%) four times, and dried under vacuum at 20-25° C. The solid material obtained was identified as dihydroxypropyl poly alpha-1,3-glucan that was water soluble, and having a degree of substitution of 0.89 (sample 1).

An additional sample of dihydroxypropyl poly alpha-1,3-glucan was produced following another method. 10 g of poly alpha-1,3-glucan ($M_w$=138,438) was added to 143 g of 20% tetraethylammonium hydroxide in a 500-mL capacity round bottom flask fitted with a thermocouple for temperature monitoring and a condenser connected to a recirculating bath, and a magnetic stir bar (resulting in ~6.5 wt % poly alpha-1,3-glucan). This preparation was stirred and heated to 30° C. on a hotplate. The preparation was stirred for 1 hour to dissolve the solid before the temperature was increased to 55° C. 3-chloro-1,2-propanediol (16 g) was then added to provide a reaction (containing ~9.5 wt % 3-chloro-1,2-propanediol), which was held at 55° C. for 2 hours before being neutralized with acetic acid. After neutralization, an excess of isopropanol was added to precipitate a solid. The solid thus formed was collected by vacuum filtration and washed with ethanol (95%) four times, and dried under vacuum at 20-25° C. The solid material obtained was identified as dihydroxypropyl poly alpha-1,3-glucan that was water soluble, and having a degree of substitution of 0.6 (sample 2).

Preparation of Hydroxyethyl Poly Alpha-1,3-Glucan 10 g of poly alpha-1,3-glucan ($M_n$=71127) was mixed with 150 mL of isopropanol and 40 mL of 30% sodium hydroxide. This preparation was stirred in a 500-mL glass beaker on a magnetic stir plate at 55° C. for 1 hour, and then stirred overnight at ambient temperature. The preparation was then transferred to a shaker tube reactor after which 15 g of ethylene oxide was added; the reaction was then stirred at 60° C. for 6 hour. The reaction was then allowed to remain in the sealed shaker tube overnight (approximately 16 hours) before it was neutralized with 20.2 g of acetic acid thereby forming hydroxyethyl poly alpha-1,3-glucan solids. The solids were filtered using a Buchner funnel with 35-micrometer filter paper. The solids were then washed in a beaker by adding a methanol:acetone (60:40 v/v) mixture and stirring with a stir bar for 20 minutes. The methanol:acetone mixture was then filtered away from the solids. This washing step was repeated two times. The solids, which had a slightly brown/beige color, were dried in a vacuum oven with a nitrogen bleed. The hydroxyethyl poly alpha-1,3-glucan product was soluble in a 10% NaOH solution. The MS of the dried product was reported by NMR to be 0.72.

Preparation of Methyl Poly Alpha-1,3-Glucan (MG)

10 g of poly alpha-1,3-glucan ($M_n$=71127) was mixed with 40 mL of 30% sodium hydroxide and 40 mL of 2-propanol, and stirred at 55° C. for 1 hour to provide alkali poly alpha-1,3-glucan. This preparation was then filtered using a Buchner funnel. The alkali poly alpha-1,3-glucan was then mixed with 150 mL of 2-propanol to make a slurry. A shaker tube reactor was charged with this slurry and 15 g of methyl chloride was added to provide a reaction. The reaction was stirred at 70° C. for 17 hours. The resulting methyl poly alpha-1,3-glucan solid was filtered and neutralized with 20 mL 90% acetic acid, followed by three 200-mL ethanol washes. NMR analysis was performed, indicating that the DoS of the methyl poly alpha-1,3-glucan product was 1.2.

Table 2 provides a list of DoS measurements for various samples of methyl poly alpha-1,3-glucan prepared using methods having certain modifications compared to the above method (refer to Table 2). The mercerization step (alkali treatment of poly alpha-1,3-glucan prior to addition of methylating reagent) for each of the processes listed in Table 2 was conducted for 1 hour, as above.

TABLE 2

Preparation of Methyl Poly Alpha-1,3-Glucan Using Various Mercerization and Methylation Conditions

| Mercerization conditions | | | Methylation conditions | | | |
|---|---|---|---|---|---|---|
| Glucan $M_n$ | Temp (° C.) | Solvent | Reagent | Time (hours) | Temp (° C.) | DoS |
| 71127 | RT | Toluene (140 mL) | DMS[a] (50 mL) | 17 | 50 | 1.51 |
| 71127 | 55 | 2-propanol (150 mL) | CH$_3$Cl (15 g) | 17 | 70 | 1.2 |

TABLE 2-continued

Preparation of Methyl Poly Alpha-1,3-Glucan Using Various Mercerization and Methylation Conditions

| Mercerization conditions | | | Methylation conditions | | | |
|---|---|---|---|---|---|---|
| Glucan $M_n$ | Temp (° C.) | Solvent | Reagent | Time (hours) | Temp (° C.) | DoS |
| 71127 | 55 | 2-propanol (150 mL) | $CH_3Cl$ (25 g) | 24 | 70 | 1.38 |
| 25084 | 55 | 2-propanol (150 mL) | $CH_3Cl$ (30 g) | 34 | 70 | 1.0 |
| 25084 | 55 | 2-propanol (150 mL) | $CH_3Cl$ (25 g) | 24 | 70 | 0.39 |

[a]Dimethyl sulfate

Additional samples of methyl poly alpha-1,3-glucan (MG) were produced following another method.

Sample 1

10 g of poly alpha-1,3-glucan ($M_w$=168584) was added to 40 mL of isopropanol and 40 mL of 30 wt % sodium hydroxide in a 400-mL beaker with a magnetic stir bar. The beaker was stirred on a magnetic stir plate at 375 rpm for one hour. The solid from this preparation was then collected by vacuum filtration, mixed with 150 mL of isopropanol, and placed in a 200-mL capacity jar with a lid. This preparation sat overnight before being transferred to a 250-mL capacity shaker tube reactor. The reactor was heated to 70° C. and charged with 10 g of methyl chloride. The reaction was held at temperature for 17 hours and then charged with an additional 20 g of methyl chloride and held at temperature for 17 hours. After cooling, the reaction was neutralized with 90% acetic acid. The solid from this reaction was collected by vacuum filtration, washed with methanol three times, dried under vacuum at 20-25° C., and analyzed by NMR to determine DoS. The solid material obtained was identified as MG with a DoS of 1.75.

8 g of this MG was then mixed with 50 mL isopropanol and 32 mL of 30 wt % sodium hydroxide in a 400-mL beaker with a magnetic stir bar. The beaker was stirred on a magnetic stir plate at 375 rpm for one hour. The solid was then collected by vacuum filtration, mixed with 150 mL of isopropanol, and placed in a 200-mL capacity jar with a lid. This preparation sat overnight before being transferred to a 250-mL capacity shaker tube reactor. The reactor was heated to 70° C. and charged with 12 g of methyl chloride. After cooling, the reaction was neutralized with 90% acetic acid. The solid was collected by vacuum filtration and washed with methanol:acetone (60:40) five times, dried under vacuum at 20-25° C., and analyzed by NMR to determine DoS. The solid material obtained was identified as MG with a DoS of 1.8. This MG was denoted as Sample 1.

Sample 2

20 g of poly alpha-1,3-glucan ($M_w$=245,000) was added to 50 mL of isopropanol and 80 mL of 30 wt % sodium hydroxide in a 400-mL beaker with a magnetic stir bar. The beaker was stirred on a magnetic stir plate at 375 rpm for one hour. The solid from this preparation was then collected by vacuum filtration, mixed with 150 mL of isopropanol, and placed in a 200-mL capacity jar with a lid. This preparation sat overnight before being transferred to a 250-mL capacity shaker tube reactor. The reactor was heated to 70° C. and charged with 30 g of methyl chloride. The reaction was held at temperature for 17 hours. After cooling, the reaction was neutralized with 90% acetic acid. The solid from this reaction was collected by vacuum filtration, washed with methanol:acetone (60:40) five times, dried under vacuum at 20-25° C., and analyzed by NMR to determine DoS. The solid material obtained was identified as MG with a DoS of 1.39.

10 g of this MG was then mixed with 50 mL isopropanol and 40 mL of 30 wt % sodium hydroxide solution in a 400-mL beaker with a magnetic stir bar. The beaker was stirred on a magnetic stir plate at 375 rpm for one hour. The solid from this preparation was then collected by vacuum filtration, mixed with 100 mL of isopropanol, and placed in a 200-mL capacity jar with a lid. This preparation sat overnight before being transferred to a 250-mL capacity shaker tube reactor. The reactor was heated to 70° C. and charged with 15 g of methyl chloride. After cooling, the reaction was neutralized with 90% acetic acid. The solid was collected by vacuum filtration and washed with methanol:acetone (60:40) five times, dried under vacuum at 20-25° C., and analyzed by NMR to determine DoS. The solid material obtained was identified as MG. This MG was denoted as Sample 2.

Additional samples of methyl poly alpha-1,3-glucan (MG) were produced using one-pot and two-pot synthesis strategies, as follows.

One-Pot Synthesis:

10 g (0.0617 moles) of poly alpha-1,3-glucan ($M_w$=~160000) and 25.55 g of 30% sodium hydroxide (total NaOH=7.665 g [0.192 moles]) were charged to a shaker tube. Then, 70 g (1.386 moles) of methyl chloride was added. This preparation was placed into a sealed pressure vessel, heated to 50° C., and shaken for 10 hours. The solid contents were then isolated. 40.7 g of solids was placed into 150 mL of 95° C. water, stirred for 30 seconds and filtered (filtrate was yellow). The solids were again stirred in water at 80-90° C. for 3 minutes; the pH of the solids was determined to be neutral. The final solid material was filtered and dried in an 85° C. vacuum oven to afford 7.6 g of a tan solid. This material was analyzed by NMR, which determined that methyl poly alpha-1,3-glucan was produced having a DoS of about 1.35.

Two-Pot Synthesis:

A 3-neck 250-mL round bottom flask with magnetic stir bar was charged with 200 g of 30% sodium hydroxide and 10 g (0.0617 moles) of poly alpha-1,3-glucan ($M_w$=~160000). This preparation was stirred at room temperature for 60 minutes. The solid was then filtered and air swept-dried in the filter for 5 minutes to yield 35.547 g of off-white solids. The solids were then charged into a pressure vessel along with 100 g of methyl chloride and the contents were stirred at 50° C. for 10 hours. The solids were collected and placed into 150 mL of 95° C. water, stirred for 30 seconds, and filtered (filtrate was yellow). The solids were again stirred in water at 80-90° C. for 3 minutes; the pH of the solids was determined to be neutral. The final solid material was filtered and dried in an 85° C. vacuum oven to afford 7.3 g of an off-white solid. This material was analyzed by NMR, which determined that methyl poly alpha-1,3-glucan was produced having a DoS of about 1.41.

Viscosity Analysis:

The MG samples isolated from the one-pot and two-pot syntheses (above) were analyzed for viscosity analysis at various shear rates mostly following the procedures described below regarding CMG shear rate analysis. The results of this experiment are listed in Table A.

TABLE A

Viscosity of MG Solutions at Various Shear Rates

| MG Sample | MG Loading | Viscosity (cPs) @ 1 rpm | Viscosity (cPs) @ 5 rpm | Viscosity (cPs) @ 9 rpm | Viscosity (cPs) @ 25 rpm |
|---|---|---|---|---|---|
| 1 | 2% | 8777 | 1874 | 1180 | 650 |
| 2 | 2 | 6628 | 2244 | 1522 | — |

The results summarized in Table A indicate that the viscosity of MG solutions is reduced as shear rate is increased. This observation means that MG solutions demonstrate shear thinning behavior.

Preparation of Ethyl Poly Alpha-1,3-Glucan (EG)

20 g of poly alpha-1,3-glucan ($M_w$=245,000) was added to 200 mL of isopropanol and 109 mL of 15 wt % sodium hydroxide in a 400-mL beaker with a magnetic stir bar. The beaker was stirred on a magnetic stir plate at 375 rpm for one hour. The solid from this preparation was then collected by vacuum filtration, mixed with 100 mL of acetone, and placed in a 200-mL capacity jar with a lid. This preparation sat overnight before being transferred to a 250-mL capacity shaker tube reactor. The reactor was heated to 90° C. and charged with 85 g of ethyl chloride. The reaction was held at temperature for 17 hours. After cooling, the reaction was neutralized with 90% acetic acid. The solid was collected by vacuum filtration, washed with 80% acetone five times, dried under vacuum at 20-25° C., and analyzed by NMR to determine DoS. The solid material obtained was identified as EG with a DoS of 1.03.

Preparation of Quaternary Ammonium Poly Alpha-1,3-Glucan 10 g of poly alpha-1,3-glucan ($M_w$=168,000) was added to 100 mL of isopropanol in a 500-mL capacity round bottom flask fitted with a thermocouple for temperature monitoring and a condenser connected to a recirculating bath, and a magnetic stir bar. 30 mL of sodium hydroxide (17.5% solution) was added dropwise to this preparation, which was then heated to 25° C. on a hotplate. The preparation was stirred for 1 hour before the temperature was increased to 55° C. 3-chloro-2-hydroxypropyl-trimethylammonium chloride (31.25 g) was then added to provide a reaction, which was held at 55° C. for 1.5 hours before being neutralized with 90% acetic acid. The solid thus formed (trimethylammonium hydroxypropyl poly alpha-1,3-glucan) was collected by vacuum filtration and washed with ethanol (95%) four times, dried under vacuum at 20-25° C., and analyzed by NMR and SEC to determine molecular weight and DoS.

Additional samples of trimethylammonium hydroxypropyl poly alpha-1,3-glucan were synthesized following the above process, but with certain process variations. Specifically, poly alpha-1,3-glucan samples with various $M_w$'s were used as starting material, and different amounts of etherification agent (3-chloro-2-hydroxypropyl-trimethylammonium chloride) were used. Also, reaction time (beginning from addition of etherification agent and ending at neutralization) was varied. Table B lists these various process variations and the resulting DoS measurements of the quaternary ammonium glucan ether products.

TABLE B

DoS of Quaternary Ammonium Hydroxypropyl Poly Alpha-1,3-Glucan Prepared from Poly Alpha-1,3-Glucan

| Sample Designation | $M_w$ of poly alpha-1,3-glucan starting material | Etherification Agent Amount | Reaction Time (hours) [a] | DoS |
|---|---|---|---|---|
| 1A | 99231 | 31.25 g | 3 | 1.26 |
| 1B-1 | 99231 | 31.25 g | 1 | 0.59 |
| 1B-2 | | | 2 | 1.05 |
| 1B-3 | | | 4 | 1.29 |
| 1C-1 | 99231 | 9 g | 1 | 0.39 |
| 1C-2 | | | 2 | 0.35 |
| 1C-3 | | | 4 | 0.31 |
| 1D | 168000 | 15 g | 2.5 | 0.43 |
| 1E-1 | 189558 | 18 g | 1 | 0.34 |
| 1E-2 | | | 2 | 0.37 |
| 1E-3 | | | 4 | 0.45 |
| 1F | 247182 | 31.25 g | 4 | 0.17 |
| 1G | 163200 | 31.25 g | 3 | 0.52 |
| 1F | 34083 | 31.25 g | 2.5 | 1.19 |

[a] Reaction time was measured from the time etherification agent was added to the time of reaction neutralization.

Homogenization

Homogenization was performed using an IKA ULTRA TURRAX T25 Digital Homogenizer (IKA, Wilmington, N.C.).

Preparation of Poly Alpha-1,3-Glucan Slurry and Wet Cake Using GtfJ Enzyme

To prepare a slurry of poly alpha-1,3-glucan, an aqueous solution (0.75 L) containing sucrose (100 g/L), potassium phosphate buffer (20 mM), and FermaSure® (500 ppm) was prepared and adjusted to pH 6.8-7.0. This solution was then charged with gtfJ enzyme extract (50 units/L). The enzyme reaction solution was maintained at 20-25° C. for 48 hours. A slurry was formed since the poly alpha-1,3-glucan synthesized in the reaction was aqueous insoluble.

The gtfJ enzyme reaction was performed as above to prepare a poly alpha-1,3-glucan wet cake. The poly alpha-1,3-glucan solids produced in the reaction were collected using a Buchner funnel fitted with a 325-mesh screen over 40-micrometer filter paper. The filtered poly alpha-1,3-glucan solids were resuspended in deionized water and filtered twice more as above to remove sucrose, fructose and other low molecular weight, soluble by-products.

$^1$H Nuclear Magnetic Resonance (NMR) Method for Determining Molar Substitution of Poly Alpha-1,3-Glucan Ether Derivatives Approximately 30 mg of the poly alpha-1,3-glucan ether derivative was weighed into a vial on an analytical balance. The vial was removed from the balance and 1.0 mL of deuterium oxide was added to the vial. A magnetic stir bar was added to the vial and the mixture was stirred to suspend the solid. Deuterated sulfuric acid (50% v/v in $D_2O$), 1.0 mL, was then added to the vial and the mixture was heated at 90° C. for 1 hour in order to depolymerize and solubilize the polymer. The solution was allowed to cool to room temperature and then a 0.8 mL portion of the solution was transferred into a 5-mm NMR tube using a glass pipet. A quantitative $^1$H NMR spectrum was acquired using an Agilent VNMRS 400 MHz NMR spectrometer equipped with a 5-mm Autoswitchable Quad probe. The spectrum was acquired at a spectral frequency of 399.945 MHz, using a spectral window of 6410.3 Hz, an acquisition time of 3.744 seconds, an inter-pulse delay of 10 seconds and 64 pulses. The time domain data were transformed using exponential multiplication of 0.50 Hz.

Two regions of the resulting spectrum were integrated for NMR analysis of hydroxypropyl poly alpha-1,3-glucan: an integral from 1.1 ppm to 1.4 ppm, representative of the three methyl protons of all isopropyl groups present; and an integral from 4.7 ppm to 5.6 ppm, representative of the anomeric protons of the glucose rings. The integral of the isopropyl methyl region was divided by 3 to obtain a measure of the OCH$_2$CH(CH$_3$)O groups that were present. The molar substitution by the OCH$_2$CH(CH$_3$)O groups was then calculated by dividing the measure of the OCH$_2$CH (CH$_3$)O groups by the measure of all glucose rings present (the integral value of the anomeric protons).

Two regions of the resulting spectrum were integrated for NMR analysis of methyl poly alpha-1,3-glucan: an integral from 3.0 ppm to 4.2 ppm was representative of the six glucan protons plus the OCH$_3$ protons, and an integral from 4.6 ppm to 5.6 ppm was representative of the anomeric protons of the glucose rings. The integral of this latter region was multiplied by six to obtain the integral of the other six glucan protons. The calculated integral for the six non-anomeric glucan protons was subtracted from the integral of the 3.0 ppm to 4.2 ppm region to obtain the integral contribution of the OCH$_3$ protons. This integral value was divided by 3.0 to obtain a measure of the OCH$_3$ groups that are present. The degree of methylation was then calculated by dividing the measure of the OCH$_3$ groups by the measure of all glucose rings present (the integral value of the anomeric protons).

Regarding NMR analysis of carboxymethyl poly alpha-1,3-glucan, the chemical shifts of the lines in the spectrum were referenced to the signal for the alpha anomeric protons with no substitution at the C$_2$OH. This signal should be the third group of peaks from the left most edge of the spectrum. The left-most signal in this group of peaks was set to 5.222 ppm. Five regions of the referenced spectrum were integrated: an integral from 5.44 ppm to 4.60 ppm represents all of the anomeric protons; the integrals from 4.46 ppm to 4.41 ppm and from 4.36 ppm to 4.32 ppm were from the carboxymethyl CH$_2$ at the C$_2$ position adjacent to either alpha or beta C1HOH; the integral from 4.41 ppm to 4.36 ppm is from the carboxymethyl CH$_2$ at the C4 position; and the integral from 4.24 ppm to 4.17 ppm was from the carboxymethyl CH$_2$ at the C6 position. The degree of carboxymethylation at the 2, 4, and 6 positions was then calculated by dividing the integrals for the OCH$_2$COOH groups by two and then dividing those results by the integration for all of the anomeric protons. A total degree of substitution was obtained by adding together the three individual degrees of substitution.

Determination of Polymer Molecular Weight

The molecular weight of poly alpha-1,3-glucan ether derivatives was determined by size exclusion chromatography (SEC) according to following protocol, unless otherwise indicated. Dry poly alpha-1,3-glucan ether derivative was dissolved in phosphate-buffered saline (PBS) (0.02-0.2 mg/mL). The chromatographic system used was an Alliance™ 2695 liquid chromatograph from Waters Corporation (Milford, Mass.) coupled with three on-line detectors: a differential refractometer 410 from Waters, a multi-angle light-scattering photometer Heleos™ 8+ from Wyatt Technologies (Santa Barbara, Calif.), and a differential capillary viscometer ViscoStar™ from Wyatt Technologies. The columns used for SEC were two Tosoh Haas Bioscience TSK GMPW$_{XL}$ g3K and g4K G3000PW and G4000PW polymeric columns for aqueous polymers. The mobile phase was PBS. The chromatographic conditions used were 30° C. at column and detector compartments, 30° C. at sample and injector compartments, a flow rate of 0.5 mL/min, and injection volume of 100 µL. The software packages used for data reduction were Astra version 6 from Wyatt (triple detection method with column calibration).

Analysis of Polymer Molecular Weight by SEC (Table 3)

The molecular weight data disclosed in Table 3 below were obtained using SEC with a differential refractive index detector. The instrument used was a WATERS ALLIANCE 2690 with a WATERS 2414 differential refractive index detector. The mobile phase was diluted PBS buffer (0.6 dilution: 6 mmol/L phosphate buffer, 1.6 mmol/L potassium chloride, 80 mmol/L sodium chloride, pH 7.4). The flow rate was 0.5 mL/min. The columns used were two TSK-GEL: GMPWXL and a guard column from Tosoh Bioscience (King of Prussia, Pa.). Samples were prepared in the mobile phase at 10 mg/mL and injection volume was 100 µL. Data were acquired and calculated using EMPOWER software from Waters Corporation. The column set was calibrated using a series of dextran standards from American Polymer Standards; thus, the molecular weight data in Table 3 are relative to dextran.

Enzyme-Mediated Hydrolysis Protocol

CMG or CMC polymer (100 mg) was added to a clean 20-mL glass scintillation vial equipped with a PTFE stir bar. Water (10.0 mL) that had been previously adjusted to pH 7.0 using 5 vol % sodium hydroxide or 5 vol % sulfuric acid was then added to the scintillation vial, and the mixture was agitated until a solution (1 wt %) formed. A cellulase or amylase enzyme was added to the solution, which was then agitated for 24 hours at room temperature (~25° C.). Each enzyme-treated sample was analyzed by SEC (above). Negative controls were conducted as above, but without the addition of a cellulase or amylase.

Examples 1 and 2 below demonstrate the superior stability of poly alpha-1,3-glucan ether derivatives over cellulose ether derivatives in aqueous compositions comprising cellulase. Examples 3-5 below demonstrate adsorption of poly alpha-1,3-glucan ether derivatives onto various fabrics. Examples 6-21 below demonstrate viscosity- and rheology-modifying effects of poly alpha-1,3-glucan ether derivatives on aqueous compositions. All these features demonstrate applicability of poly alpha-1,3-glucan ether derivatives for use in various applications such as in fabric care detergents (e.g., laundry detergent).

Examples 1-2

Effect of Cellulase on Carboxymethyl Poly Alpha-1,3-Glucan (CMG)

These examples disclose the superior stability of a poly alpha-1,3-glucan ether, CMG, in the presence of cellulase compared to carboxymethyl cellulose (CMC).

Solutions (1 wt %) of CMC ($M_w$=90000, DoS=0.7) or CMG ($M_w$=101500, DoS=0.47, sample designation D102709-44 in Table 1) were treated with cellulase or amylase (Table 3) following the above-described procedure. CMC $M_w$ decreased by over 60% when treated with cellulase for 24 hours (Table 3, Example 1.1). Conversely, CMG polymer $M_w$ was reduced by only 1.1% and 10.6% when treated with cellulase (Table 3, Examples 2.1 and 2.4, respectively). Both CMC and CMG were stable against degradation by amylase (Table 3, Examples 1.2, 2.2 and 2.3). Control polymer solutions underwent the same treatment protocol, with the exception that neither a cellulase or amylase were included in the treatment. The controls indicate that the 24-hour agitation aspect of the above treatment protocol marginally reduced molecular weight of both CMG and CMC.

TABLE 3

Measuring Stability of CMG and CMC Against Degradation by Cellulase or Amylase

| Example | Polymer | Enzyme | Enzyme Type | Enzyme Loading | $M_n$ (K) | $M_w$ (K) | Percent Degradation[a] |
|---|---|---|---|---|---|---|---|
| 1 (control) | CMC | none | N/A | — | 51.4 | 88.7 | |
| 1.1 | CMC | PURADAX HA 1200E | Cellulase | 1 mg/mL | 12.7 | 33.3 | 62.5 |
| 1.2 | CMC | PREFERENZ S 100 | Amylase | 3 μL/mL | 44.8 | 83.7 | 5.6 |
| 2 (control) | CMG | none | N/A | — | 49.1 | 108.1 | |
| 2.1 | CMG | PURADAX HA 1200E | Cellulase | 1 mg/mL | 46.8 | 106.9 | 1.1 |
| 2.2 | CMG | PREFERENZ S 100 | Amylase | 3 μL/mL | 48.5 | 105.2 | 2.7 |
| 2.3 | CMG | PURASTAR ST L | Amylase | 3 μL/mL | 44.3 | 103.6 | 4.2 |
| 2.4 | CMG | PURADAX EG L | Cellulase | 3 μL/mL | 45 | 96.6 | 10.6 |

[a]Percent degradation of polymer $M_w$ by cellulase or amylase.

The data in Table 3 indicate that CMC is highly susceptible to degradation by cellulase, whereas CMG is resistant to this degradation. Since high polymer molecular weight is a key characteristic of a soluble polysaccharide ether for providing viscosity to aqueous compositions, use of CMC for providing viscosity to an aqueous composition (e.g., laundry or dishwashing detergent) containing cellulase would be unacceptable.

Examples 6-19 below show that CMG and other types of poly alpha-1,3-glucan ether derivatives act as viscosity and rheology modifiers of aqueous compositions. Thus, given the resistance of CMG to cellulase activity, this poly alpha-1,3-glucan ether derivative would be very useful for providing viscosity to cellulase-containing aqueous compositions such as detergents. It is reasonable to conclude that this result similarly applies to other poly alpha-1,3-glucan ether derivatives.

Example 3

Creating Calibration Curves for Direct Red 80 and Toluidine Blue 0 Dyes Using UV Absorption This example discloses creating calibration curves useful for determining the relative level of adsorption of poly alpha-1,3-glucan ether derivatives onto fabric surfaces.

Solutions of known concentration (ppm) were made using Direct Red 80 and Toluidine Blue O dyes. The absorbance of these solutions was measured using a LAMOTTE SMART2 Colorimeter at either 520 or 620 nm. The absorption information was plotted in order that it could be used to determine dye concentration of solutions which were exposed to fabric samples. The concentration and absorbance of each calibration curve are provided in Tables 4 and 5.

TABLE 4

Direct Red 80 Dye Calibration Curve Data

| Dye Concentration (ppm) | Average Absorbance @520 nm |
|---|---|
| 25 | 0.823333333 |
| 22.5 | 0.796666667 |
| 20 | 0.666666667 |
| 15 | 0.51 |
| 10 | 0.37 |
| 5 | 0.2 |

TABLE 5

Toluidine Blue O Dye Calibration Curve Data

| Dye Concentration (ppm) | Average Absorbance @620 nm |
|---|---|
| 12.5 | 1.41 |
| 10 | 1.226666667 |
| 7 | 0.88 |
| 5 | 0.676666667 |
| 3 | 0.44 |
| 1 | 0.166666667 |

Thus, calibration curves were prepared that are useful for determining the relative level of adsorption of poly alpha-1,3-glucan ether derivatives onto fabric surfaces. These calibration curves were utilized in Examples 4 and 5.

Example 4

Adsorption of Quaternary Ammonium Poly Alpha-1,3-Glucan Ether on Various Fabrics This example discloses testing the degree of adsorption of a quaternary ammonium poly alpha-1,3-glucan (trimethylammonium hydroxypropyl poly alpha-1,3-glucan) on different types of fabrics.

A 0.07 wt % solution of trimethylammonium hydroxypropyl poly alpha-1,3-glucan (Sample 1F, Table B, General Methods) was made by dissolving 0.105 g of the polymer in 149.89 g of deionized water. This solution was divided into several aliquots with different concentrations of polymer and other components (Table 6). Such other components were acid (dilute hydrochloric acid) or base (sodium hydroxide) to modify pH, or NaCl salt.

TABLE 6

Quaternary Ammonium Poly Alpha-1,3-GlucanSolutions Used in Fabric Adsorption Studies

| Amount of NaCl (g) | Amount of Solution (g) | Polymer Concentration (wt %) | Amount of Acid (g) | Amount of Base (g) | Final pH |
|---|---|---|---|---|---|
| 0 | 15 | 0.07 | n/a | n/a | ~7 |
| 0.15 | 14.85 | 0.0693 | n/a | n/a | ~7 |
| 0.3 | 14.7 | 0.0686 | n/a | n/a | ~7 |
| 0.45 | 14.55 | 0.0679 | n/a | n/a | ~7 |
| 0 | 9.7713 | 0.0683 | 0.2783 | n/a | 2.92 |
| 0 | 9.7724 | 0.0684 | 0.2369 | n/a | 4.96 |
| 0 | 10.0311 | 0.0702 | n/a | 0.0319 | 9.04 |
| 0 | 9.9057 | 0.0693 | n/a | 0.1059 | 11.05 |

Four different fabric types (cretonne, polyester, 65:35 polyester/cretonne, bleached cotton) were cut into 0.17 g pieces. Each piece was placed in a 2-mL well in a 48-well cell culture plate. Each fabric sample was exposed to 1 mL of each of the above solutions (Table 6) for a total of 36 samples (a control solution with no polymer was included for each fabric test). The fabric samples were allowed to sit for at least 30 minutes in the polymer solutions. The fabric samples were removed from the polymer solutions and rinsed in DI water for at least one minute to remove any unbound polymer. The fabric samples were then dried at 60° C. for at least 30 minutes until constant dryness was achieved. The fabric samples were weighed after drying and individually placed in 2-mL wells in a clean 48-well cell culture plate. The fabric samples were then exposed to 1 mL of a 250 ppm Direct Red 80 dye solution. The samples were left in the dye solution for at least 15 minutes. Each fabric sample was removed from the dye solution, afterwhich the dye solution was diluted 10×.

The absorbance of the diluted solutions was measured compared to a control sample. A relative measure of glucan polymer adsorbed to the fabric was calculated based on the calibration curve created in Example 3 for Direct Red 80 dye. Specifically, the difference in UV absorbance for the fabric samples exposed to polymer compared to the controls (fabric not exposed to polymer) represents a relative measure of polymer adsorbed to the fabric. This difference in UV absorbance could also be expressed as the amount of dye bound to the fabric (over the amount of dye bound to control), which was calculated using the calibration curve (i.e., UV absorbance was converted to ppm dye). Table 7 provides "dye (ppm)"; a positive value represents the dye amount that was in excess to the dye amount bound to the control fabric, whereas a negative value represents the dye amount that was less than the dye amount bound to the control fabric. A positive value reflects that the glucan ether compound adsorbed to the fabric surface.

TABLE 7

Relative Amount of Quaternary Ammonium Poly Alpha-1,3-Glucan Bound to Different Fabrics Under Different Conditions

| Cretonne | | Polyester | | 65:35 Polyester/Cretonne | | Bleached Cotton | |
| --- | --- | --- | --- | --- | --- | --- | --- |
| Salt Conc. | dye (ppm)$^a$ | Salt Conc. | dye (ppm)$^a$ | Salt Conc. | dye (ppm)$^a$ | Salt Conc. | dye (ppm)$^a$ |
| 0$^b$ | +4.56 | 0$^b$ | +0.48 | 0b | +1.27 | 0$^b$ | +3.13 |
| 1%$^b$ | +1.97 | 1%$^b$ | +0.46 | 1%$^b$ | +0.58 | 1%$^b$ | +3.78 |
| 2%$^b$ | −0.52 | 2%$^b$ | +0.0003 | 2%$^b$ | +0.16 | 2%$^b$ | +4.11 |
| 3%$^b$ | 0 | 3%$^b$ | +0.10 | 3%$^b$ | +0.07 | 3%$^b$ | −0.13 |
| pH$^c$ | | pH$^c$ | | pH$^c$ | | pH$^c$ | |
| 3 | +2.06 | 3 | −0.29 | 3 | −0.26 | 3 | +2.97 |
| 5 | +3.13 | 5 | +0.13 | 5 | −0.33 | 5 | +2.87 |
| 9 | +2.05 | 9 | −0.003 | 9 | +0.07 | 9 | +4.69 |
| 11 | +2.02 | 11 | −0.59 | 11 | +0.12 | 11 | +2.03 |

$^a$Amount of dye bound to fabric. A positive value represents the dye amount that was in excess to the dye amount bound to control. A positive dye amount in turn represents the relative amount of glucan ether adsorbed to the fabric.
$^b$The pH of binding conditions was about 7 (refer to Table 6).
$^c$Binding conditions did not include salt (refer to Table 6).

The data in Table 7 indicate that quaternary ammonium glucan polymer can adsorb to various types of fabric under different salt and pH conditions. This adsorption occurs even though the fabrics were rinsed after exposure to the polymer. It is notable that the glucan ether was able to adsorb to polyester and the polyester/cretonne blend, in addition to adsorbing to cotton.

Thus, a poly alpha-1,3-glucan ether derivative in an aqueous composition can adsorb to fabric. This adsorption reflects that cationic glucan ether derivatives should be useful in detergents for fabric care (e.g., as anti-redeposition agents).

Example 5

Adsorption of Carboxymethyl Poly Alpha-1,3-Glucan (CMG) on Various Fabrics

This example discloses testing the degree of adsorption of a poly alpha-1,3-glucan ether compound (CMG) on different types of fabrics.

A 0.25 wt % solution of CMG was made by dissolving 0.375 g of the polymer in 149.625 g of deionized water. This solution was divided into several aliquots with different concentrations of polymer and other components (Table 8). Such other components were acid (dilute hydrochloric acid) or base (sodium hydroxide) to modify pH, or NaCl salt.

TABLE 8

CMG Solutions Used in Fabric Adsorption Studies

| Amount of NaCl (g) | Amount of Solution (g) | Polymer Concentration (wt %) | Amount of Acid (g) | Amount of Base (g) | Final pH |
| --- | --- | --- | --- | --- | --- |
| 0 | 15 | 0.25 | n/a | n/a | ~7 |
| 0.15 | 14.85 | 0.2475 | n/a | n/a | ~7 |
| 0.3 | 14.7 | 0.245 | n/a | n/a | ~7 |
| 0.45 | 14.55 | 0.2425 | n/a | n/a | ~7 |
| 0 | 9.8412 | 0.2459 | 0.1641 | n/a | 3.52 |
| 0 | 9.4965 | 0.2362 | 0.553 | n/a | 5.01 |
| 0 | 9.518 | 0.2319 | n/a | 0.752 | 8.98 |
| 0 | 9.8811 | 0.247 | n/a | 0.1189 | 10.93 |

Four different fabric types (cretonne, polyester, 65:35 polyester/cretonne, bleached cotton) were cut into 0.17 g pieces. Each piece was placed in a 2-mL well in a 48-well cell culture plate. Each fabric sample was exposed to 1 mL of each of the above solutions (Table 8) for a total of 36 samples (a control solution with no polymer was included for each fabric test). The fabric samples were allowed to sit for at least 30 minutes in the polymer solutions. The fabric samples were removed from the polymer solutions and rinsed in DI water for at least one minute to remove any unbound polymer. The fabric samples were then dried at 60° C. for at least 30 minutes until constant dryness was achieved. The fabric samples were weighed after drying and individually placed in 2-mL wells in a clean 48-well cell culture plate. The fabric samples were then exposed to 1 mL of a 250 ppm Toluidine Blue dye solution. The samples were left in the dye solution for at least 15 minutes. Each fabric sample was removed from the dye solution, afterwhich the dye solution was diluted 10×.

The absorbance of the diluted solutions was measured compared to a control sample. A relative measure of glucan polymer adsorbed to the fabric was calculated based on the calibration curve created in Example 3 for Toluidine Blue dye. Specifically, the difference in UV absorbance for the fabric samples exposed to polymer compared to the controls (fabric not exposed to polymer) represents a relative measure of polymer adsorbed to the fabric. This difference in UV absorbance could also be expressed as the amount of dye bound to the fabric (over the amount of dye bound to control), which was calculated using the calibration curve (i.e., UV absorbance was converted to ppm dye). Table 9 provides "dye (ppm)"; a positive value represents the dye amount that was in excess to the dye amount bound to the control fabric, whereas a negative value represents the dye amount that was less than the dye amount bound to the control fabric. A positive value reflects that the glucan ether compound adsorbed to the fabric surface.

TABLE 9

Relative Amount of CMG Bound to Different Fabrics Under Different Conditions

| Cretonne | | Polyester | | 65:35 Polyester/Cretonne | | Bleached Cotton | |
|---|---|---|---|---|---|---|---|
| Salt Conc. | dye (ppm)$^a$ | Salt Conc. | dye (ppm)$^a$ | Salt Conc. | dye (ppm)$^a$ | Salt Conc. | dye (ppm)$^a$ |
| 0$^b$ | 0.29 | 0$^b$ | 0 | 0$^b$ | 0 | 0b | +9.28 |
| 1%$^b$ | +2.25 | 1%$^b$ | +5.18 | 1%$^b$ | +0.49 | 1%$^b$ | +6.26 |
| 2%$^b$ | −0.19 | 2%$^b$ | +3.62 | 2%$^b$ | +1.76 | 2%$^b$ | +5.57 |
| 3%$^b$ | +1.37 | 3%$^b$ | +1.47 | 3%$^b$ | +1.76 | 3%$^b$ | +7.62 |
| pH$^c$ | | pH$^c$ | | pH$^c$ | | pH$^c$ | |
| 3.5 | −1.47 | 3.5 | +1.76 | 3.5 | −0.39 | 3.5 | +3.22 |
| 5 | +0.02 | 5 | +7.62 | 5 | −1.17 | 5 | +10.17 |
| 9 | +0.78 | 9 | +1.36 | 9 | −1.95 | 9 | +17.11 |
| 11 | +4.39 | 11 | +0.78 | 11 | +2.54 | 11 | +15.73 |

$^a$Amount of dye bound to fabric. A positive value represents the dye amount that was in excess to the dye amount bound to control. A positive dye amount in turn represents the relative amount of glucan ether adsorbed to the fabric.
$^b$The pH of binding conditions was about 7 (refer to Table 8).
$^c$Binding conditions did not include salt (refer to Table 8).

The data in Table 9 indicate that CMG polymer can adsorb to various types of fabric under different salt and pH conditions. This adsorption occurs even though the fabrics were rinsed after exposure to the polymer. It is notable that the glucan ether was able to adsorb to polyester and the polyester/cretonne blend, considering that carboxymethyl cellulose does not absorb to, or only poorly adsorbs to, polyester and blends thereof with cotton (see European Pat. Appl. Publ. No. EP0035478, for example).

Thus, a poly alpha-1,3-glucan ether derivative in an aqueous composition can adsorb to fabric. This adsorption reflects that glucan ether derivatives should be useful in detergents for fabric care (e.g., as anti-redeposition agents).

Example 6

Effect of Dissolution Method on Viscosity of Carboxymethyl Poly Alpha-1,3-Glucan (CMG) Solutions This Example describes the viscosity of CMG solutions prepared using different dissolution techniques.

A sample of CMG (1G, Table 1) was prepared as described in the General Methods and then dissolved using three different methods:

a) Homogenization: 1 g of CMG (1G) was added to de-ionized (DI) water (49 g) to provide a 2 wt % CMG preparation, which was then homogenized for 12-15 seconds at 20,000 rpm to dissolve the CMG. No filtering was needed because there were no particulates in the solution.

b) Mechanical mixing: DI water (49 g) was stirred at 400 rpm using an overhead mixer equipped with a propeller blade. 1 g of CMG (1G) was gradually added to the vortex created by the mixer to provide a 2 wt % CMG preparation, which was then warmed to 25° C. using a water bath and a hot plate to obtain uniform heating. The preparation was stirred until all CMG was dissolved. The resulting solution was then filtered by vacuum to remove any particulate material.

c) Manual shaking: 1 g of the CMG (1G) was added to 49 g of DI water to provide a 2 wt % CMG preparation, which was then shaken by hand for 10-15 seconds and allowed to sit overnight to complete dissolution. The resulting solution was then filtered by vacuum to remove any particulate material.

To determine the viscosity of each CMG solution at various shear rates, dissolved CMG samples were subjected to 10, 60, 150, and 250 rpm shear rates using a Brookfield III+ Rheometer equipped with a recirculating bath to control temperature (20° C.) and a SC4-21 Thermosel® spindle. The shear rate was increased using a gradient program which increased from 10-250 rpm and the shear rate was increased by 4.9 (1/s) every 20 seconds. The results of this experiment are listed in Table 10.

TABLE 10

Effect of Dissolution Method on the Viscosity of CMG

| CMG Sample | CMG Loading | Dissolution Method | Viscosity (cPs) @ 10 rpm | Viscosity (cPs) @ 60 rpm | Viscosity (cPs) @ 150 rpm | Viscosity (cPs) @ 250 rpm |
|---|---|---|---|---|---|---|
| 1G | 2% | Manual Shaking | 405.7 | 317.69 | 201.3 | 168.8 |
| 1G | 2% | Mechanical stirring | 827.7 | 304.3 | 196.4 | 161.6 |
| 1G | 2% | Homogenizer | 8379.3 | 980.7 | 442.4 | 327.2 |

The results summarized in Table 10 indicate that the method of dissolving CMG can have an effect on the viscosity of the solution. The samples that were either manually shaken or mechanically stirred showed lower viscosity compared to the sample that was homogenized. It appears that the filtration step that followed manual shaking or mechanical stirring has a dramatic effect on reducing the viscosity.

Thus, a solution of CMG prepared by homogenization had greater viscosity compared to CMG solutions prepared by manual shaking and mechanical stirring.

Example 7

Effect of Shear Rate on Viscosity of CMG

This Example describes the effect of shear rate on the viscosity of various CMG solutions, where the solutions were prepared using CMG with different molecular weights. It is shown that CMG solutions exhibit significant shear thinning behavior. Thus, addition of CMG to a liquid can modify the rheological behavior of the liquid.

Various solutions of CMG with different molecular weights were prepared as described in Example 6 by homogenization. Specifically, to prepare a 2 wt % solution of each of these samples, 1 g of CMG (particular samples from Table 1) was added to 49 g of DI water. Each preparation was then homogenized for 12-15 seconds at 20,000 rpm to dissolve the CMG.

The viscosity of each CMG solution was measured as in Example 6. The results of this experiment are listed in Table 11.

TABLE 11

Viscosity of CMG Solutions with Different Molecular Weights at Various Shear Rates

| CMG Sample | CMG Loading | Viscosity (cPs) @ 10 rpm | Viscosity (cPs) @ 60 rpm | Viscosity (cPs) @ 150 rpm | Viscosity (cPs) @ 250 rpm |
|---|---|---|---|---|---|
| 1C | 2% | 93 | 73 | 64 | 60 |
| 1D | 2% | 10 | 10 | 10 | 10 |
| 1E | 2% | 1242 | 713.9 | 504 | 414.6 |
| 1F | 2% | 5393 | 1044 | 656 | 454 |
| 1J | 2% | 8379.3 | 980.7 | 442.4 | 327.2 |

The results summarized in Table 11 indicate that the viscosity of most of the CMG solutions is reduced as the shear rate is increased. This observation means that CMG solutions demonstrate significant shear thinning behavior.

Thus, CMG when dissolved in an aqueous solution not only modifies the viscosity of the solution, but also the rheological properties of the solution. CMG can therefore be added to an aqueous liquid to modify its rheological profile.

Example 8

Effect of Temperature on Viscosity

This Example describes the effect of temperature on the viscosity of CMG solutions.

A 2 wt % solution of CMG (1G, Table 1) was prepared as described in Example 6 using the homogenization method. The viscosity of the CMG solution was measured using a Brookfield DV III+ Rheometer equipped with a recirculating bath to control temperature and a SC4-21 Thermosel® spindle. The shear rate was held constant at 60 rpm while the temperature was increased by 2° C. every 2 minutes. The temperature was increased from 20° C. to 70° C. and viscosity measurements were taken at certain temperatures. The results are shown in Table 12.

TABLE 12

Effect of Temperature on the Viscosity of CMG Solutions

| Temperature (° C.) | Viscosity (cPs) @ 60 rpm |
|---|---|
| 20 | 784.3 |
| 40 | 491.4 |
| 50 | 435.6 |
| 60 | 404.6 |
| 70 | 365.8 |

The results summarized in Table 12 indicate a decrease in viscosity as the temperature is increased.

Example 9

Effect of Degree of Substitution on Viscosity

This Example describes the effect of DoS of CMG on the viscosity of CMG in solution.

Two solutions of 2 wt % CMG (1G and 1H, Table 1) were prepared as described in Example 6 using the homogenization method. The viscosity of each solution was measured according to Example 6 and the results are shown in Table 13.

TABLE 13

Effect of Degree of Substitution on Viscosity

| CMG Sample | DoS | Viscosity (cPs) @ 10 rpm | Viscosity (cPs) @ 60 rpm | Viscosity (cPs) @ 150 rpm | Viscosity (cPs) @ 250 rpm |
|---|---|---|---|---|---|
| 1G | 0.5 | 8379.3 | 980.8 | 442.4 | 327.2 |
| 1H | 0.9 | n/a | n/a | 61.8 | 57.2 |

The results summarized in Table 13 indicate that as the DoS of the CMG polymer is increased, there is a decrease in viscosity. Note that the Brookfield Rheometer was not capable of accurately measuring the viscosity at low shear rates (10 and 60 rpm) for the CMG with DoS 0.9. However, as the shear rate was increased to 150 rpm and 250 rpm for this CMG, the torque on the instrument increased and the viscosity measurement became reliable.

Thus, CMG with a lower DoS has greater viscosifying activity than CMG with a higher DoS.

Example 10

Effect of pH on Viscosity of CMG

This Example describes the effect of pH on the viscosity of CMG in solution.

A solution of 2 wt % CMG (1G, Table 1) was prepared as described in Example 6 using the homogenization method. The solution was divided into four aliquots, which were adjusted to pH 3.5, pH 4.5, pH 4.8 or pH 5.0 using citric acid.

A second solution of 2 wt % CMG (1G, Table 1) was prepared as in Example 6 using the homogenization method. The solution was divided into two aliquots. One aliquot was adjusted to pH 3.0 using citric acid and the second aliquot was adjusted to pH 12 using sodium hydroxide.

The viscosity of each of the above preparations was measured according to Example 6 and the results are shown in Table 14.

Solutions of 1 wt %, 1.5 wt %, or 2 wt % CMG (1I and 1J, Table 1) were prepared as in Example 6 using the homogenization method. The solutions were then adjusted to pH 3, pH 3.5, pH 4, pH 5, pH 6, or pH 7 using glacial acetic acid. The viscosity of certain preparations was measured according to Example 6 (results shown in Table 14), but with the following modifications. Certain viscosity measurements were made using a Brookfield III+ Rheometer equipped with either a SC4-21 or SC4-18 Thermosel® spindle. Viscosity measurements were made at 10 rpm, 58.98 rpm, 152 rpm and 232.5 rpm shear rates.

TABLE 14

Viscosity of CMG Solutions at Various pHs

| CMG Sample | CMG Loading | pH | Spindle | Viscosity (cPs) @ 10 rpm | Viscosity (cPs) @ 60 rpm | Viscosity (cPs) @ 150 rpm | Viscosity (cPs) @ 250 rpm |
|---|---|---|---|---|---|---|---|
| 1G | 2% | 3.0 | SC4-21 | 223.2 | 66.2 | 34.9 | 27.6 |
| 1G | 2% | 3.5 | SC4-21 | 2064.6 | 1255.1 | n/a | 440 |
| 1G | 2% | 4.5 | SC4-21 | 6891.3 | 1573.7 | 607.6 | 386.8 |
| 1G | 2% | 4.8 | SC4-21 | 10230 | 1734.5 | 673 | 440 |
| 1G | 2% | 5.0 | SC4-21 | 7328.4 | 1447.5 | 509.7 | 333.6 |
| 1G | 2% | 12 | SC4-21 | 2325 | 636.3 | 302.2 | 216 |

TABLE 14-continued

| CMG Sample | Loading | pH | Spindle | Viscosity (cPs) @ 10 rpm | Viscosity (cPs) @ 58.98 rpm | Viscosity (cPs) @ 152.0 rpm | Viscosity (cPs) @ 232.5 rpm |
|---|---|---|---|---|---|---|---|
| 1I | 1% | 3.5 | SC4-18 | 1799.4 | 388.17 | 213.42 | 142.26 |
| 1I | 1% | 4.0 | SC4-18 | 1140.48 | 325.14 | 145.06 | 109.82 |
| 1I | 1% | 5.0 | SC4-18 | n/a | 187.64 | 90.59 | 72.99 |
| 1I | 1% | 6.0 | SC4-18 | n/a | 118.89 | 91.15 | 76.37 |
| 1I | 1% | 7.0 | SC4-18 | n/a | 190.5 | 127.83 | 98.33 |
| 1I | 2% | 3.0 | SC4-21 | 120 | 97.76 | 59.35 | 47.6 |
| 1I | 2% | 3.5 | SC4-21 | 3720 | 1354.48 | n/a | n/a |
| 1I | 2% | 4.0 | SC4-21 | 6454.2 | n/a | n/a | n/a |
| 1I | 2% | 5.0 | SC4-21 | 9197.7 | 1351.32 | 534.14 | n/a |
| 1I | 2% | 6.0 | SC4-21 | 7030.8 | 1256.71 | 460.72 | 354.4 |
| 1J | 2% | 3.5 | SC4-18 | 3505.92 | 658.88 | 334.59 | 234.18 |
| 1J | 2% | 4.0 | SC4-18 | 3269.38 | 658.88 | 307.91 | 216.27 |
| 1J | 2% | 5.0 | SC4-18 | 3970.56 | 671.77 | 278.45 | 183.15 |
| 1J | 2% | 7.0 | SC4-21 | 3840.9 | 622.84 | 351.2 | 263.2 |
| 1J | 2% | 5.0 | SC4-21 | 4175.7 | 668.57 | 324.28 | 222.4 |
| 1J | 2% | 4.0 | SC4-21 | 7008.9 | 763.17 | 313.88 | 273.6 |
| 1J | 1.5% | 4.0 | SC4-18 | 2289.41 | 388.17 | 181.19 | 126.72 |
| 1J | 1.5% | 5.0 | SC4-18 | n/a | 217.72 | 110.05 | 88.54 |

The results summarized in Table 14 for CMG sample 1G indicate a viscosity decrease at pH 3.5. The viscosity of the CMG (1G) solutions at pH levels above 4.5 indicated no decrease in viscosity, except that at pH 12 there was a slight decrease in viscosity.

The pH of each of the CMG solutions in the above procedure was adjusted following the preparation of each solution. To examine if the order of addition of the acid for pH adjustment had any impact on the viscosity of the solution, DI water was adjusted to pH 3 using citric acid. A 2 wt % solution of CMG (1G, Table 1) was prepared using the pH 3 DI water/citric acid and homogenized according to Example 6 to dissolve the polymer. The viscosity of this solution was measured as in Example 6 and is listed in Table 15.

TABLE 15

Viscosity of CMG Solution—Reverse Addition of Acid for pH Adjustment

| CMG Sample | CMG Loading | pH | Viscosity (cPs) @ 10 rpm | Viscosity (cPs) @ 60 rpm | Viscosity (cPs) @ 150 rpm | Viscosity (cPs) @ 250 rpm |
|---|---|---|---|---|---|---|
| 1G | 2% | 3 | 9188.4 | 1444.4 | 665.1 | 416.8 |

The results summarized in Table 15 indicate that when the water is pH-adjusted before the CMG polymer is dissolved, the viscosity is stable (i.e., the viscosity values in Table 15 at each respective shear rate are greater than those listed in the top row of Table 14). This could be due to a buffering effect of the polymer.

Thus, pH affects the viscosity of CMG solutions.

Example 11

Effect of Sodium Chloride on the Viscosity of CMG

This Example describes the effect of sodium chloride on the viscosity of CMG in solution.

A 2 wt % solution of CMG (1G, Table 1) was prepared by adding 3 g of CMG to 147 g of DI water as described in Example 6 using the homogenization method. The CMG solution thus prepared was divided into three aliquots, each weighing 49.98 g, 49.84 g, and 45.63 g, respectively. Sodium chloride (0.025 g) was added to the 49.98 g CMG solution to make a solution of 2 wt % CMG in 0.05 wt % sodium chloride. Sodium chloride (0.15 g) was added to the 49.84 g CMG solution to make a solution of 2 wt % CMG in 0.3 wt % sodium chloride. Sodium chloride (0.47 g) was added to the 45.63 g CMG solution to make a solution of 2 wt % CMG in 1 wt % sodium chloride. The viscosity levels of each of the solutions were measured as described in Example 6 and are shown in Table 16.

To determine if the order of addition of sodium chloride had any effect on the final viscosity of the CMG solution, a 1% solution of sodium chloride was made by dissolving 0.5 g of sodium chloride in 49.5 g of DI water. CMG (1 g) was added to 49 g of the 1% sodium chloride using the homogenization method as described in Example 6. The viscosity of the solution was measured as described in Example 6 and is shown as sample 1G-1 in Table 16.

TABLE 16

Effect of Sodium Chloride on CMG Viscosity

| CMG Sample | CMG Loading | Sodium Chloride Conc. | Viscosity (cPs) @ 10 rpm | Viscosity (cPs) @ 60 rpm | Viscosity (cPs) @ 150 rpm | Viscosity (cPs) @ 250 rpm |
|---|---|---|---|---|---|---|
| 1G | 2% | 0.05% | n/a | 316.9 | 219 | 206 |
| 1G | 2% | 0.3% | 957.9 | 484.1 | 301.6 | 261.2 |
| 1G | 2% | 1% | 1236.2 | 567.6 | 366.5 | 302 |
| 1G-1 | 2% | 1% | 1795.9 | 539.2 | 299.7 | 221.2 |

The results summarized in Table 16 indicate that neither the presence of sodium chloride nor the method of its addition to the CMG solution have a significant impact on the viscosity of CMG in solution.

Example 12

Effect of Sodium Sulfate on the Viscosity of CMG

This Example describes the effect of sodium sulfate on the viscosity of CMG in solution.

A 2 wt % solution of CMG (1G, Table 1) was prepared as described in Example 6 using the homogenization method. This solution was then divided into three portions each weighing 30.00 g, 29.69 g, and 29.92 g, respectively. Sodium sulfate (0.014 g) was dissolved in the 30.00 g CMG solution to make a solution of 2 wt % CMG in 0.047 wt % sodium sulfate. Sodium sulfate (0.088 g) was dissolved in the 29.69 g solution of CMG to make a solution of 2 wt % CMG in 0.3 wt % sodium sulfate. Sodium sulfate (0.29 g) was dissolved in the 29.92 g CMG solution to make a solution of 2 wt % CMG in 0.96 wt % sodium sulfate. The viscosity levels of each of the solutions were measured as described in Example 6 and are shown in Table 17.

TABLE 17

Effect of Sodium Sulfate on CMG Viscosity

| CMG Sample | CMG Loading | Sodium Sulfate Conc. | Viscosity (cPs) @ 10 rpm | Viscosity (cPs) @ 60 rpm | Viscosity (cPs) @ 150 rpm | Viscosity (cPs) @ 250 rpm |
|---|---|---|---|---|---|---|
| 1G | 2% | 0.05% | 1292.7 | 559.8 | 290.6 | 230.8 |
| 1G | 2% | 0.3% | 4640.7 | 640.2 | 310.8 | 237.6 |
| 1G | 2% | 1% | 5245.2 | 774.2 | 331.62 | 246.4 |

The results summarized in Table 17 indicate that the presence of sodium sulfate did not have a significant impact on the viscosity of CMG in solution.

Example 13

Effect of Sucrose on the Viscosity of CMG

This Example describes the effect of sucrose on the viscosity of CMG in solution.

A 2 wt % solution of CMG (1G, Table 1) was prepared as described in Example 6 using the homogenization method. This solution was divided into two portions each weighing 45 g and 20 g, respectively. To prepare a 10 wt % solution of sucrose in CMG, 5 g of sucrose was dissolved in 45 g of the CMG solution. For a 60 wt % solution of sucrose in CMG, 30 g of sucrose was dissolved by hand mixing with 20 g of the CMG solution. The viscosity levels of each of the solutions were measured as described in Example 6 and are shown in Table 18.

TABLE 18

Effect of Sucrose on CMG Viscosity

| CMG Sample | CMG Loading | Sucrose Conc. | Viscosity (cPs) @ 10 rpm | Viscosity (cPs) @ 60 rpm | Viscosity (cPs) @ 150 rpm | Viscosity (cPs) @ 250 rpm |
|---|---|---|---|---|---|---|
| 1G | 2% | 10% | 7151.7 | 1067.5 | 430.7 | 322.8 |
| 1G | 2% | 60% | 4278 | n/a | n/a | n/a |

The results summarized in Table 18 indicate that the presence of 10% sucrose does not have any impact on the viscosity of the CMG. However, an increased amount of sucrose (60%) decreased the viscosity.

Example 14

Effect of Shear Rate on Viscosity of Potassium/Sodium CMG

This Example describes the effect of shear rate on the viscosity of potassium/sodium CMG (KNaCMG) in solution. It is shown that KNaCMG in solution exhibits significant shear thinning behavior. Thus, addition of KNaCMG to a liquid can modify the rheological behavior of the liquid.

A KNaCMG sample was prepared as described in the General Methods. To prepare a 2 wt % solution of KNaCMG, 1 g of KNaCMG was added to 49 g of DI water. This preparation was then homogenized for 12-15 seconds at 20,000 rpm to dissolve the KNaCMG.

To determine the viscosity of the KNaCMG solution at various shear rates, KNaCMG samples were subjected to various shear rates using a Brookfield III+ Rheometer equipped with a recirculating bath to control temperature (20° C.) and a YULA15-E(Z) spindle. The shear rate was increased using a gradient program which increased from 0.01-250 rpm and the shear rate was increased by 7.36 (1/s) every 20 seconds. The results of this experiment are listed in Table 19.

TABLE 19

Viscosity of KNaCMG Solution at Various Shear Rates

| KNaCMG Loading | Viscosity (cPs) @ 22.07 rpm | Viscosity (cPs) @ 80.89 rpm | Viscosity (cPs) @ 161.8 rpm | Viscosity (cPs) @ 250 rpm |
|---|---|---|---|---|
| 2% | 108.52 | 82.06 | 69.47 | 62.12 |

The results summarized in Table 19 indicate that the viscosity of the KNaCMG solution is reduced as the shear rate is increased. This observation means that KNaCMG solutions demonstrate significant shear thinning behavior.

Thus, KNaCMG when dissolved in an aqueous solution not only modifies the viscosity of the solution, but also the rheological properties of the solution. KNaCMG can therefore be added to an aqueous liquid to modify its rheological profile.

The procedure in this Example could easily be adapted to use potassium carboxymethyl poly alpha-1,3-glucan (KCMG) instead of KNaCMG.

Example 15

Effect of Shear Rate on Viscosity of Lithium/Sodium CMG

This Example describes the effect of shear rate on the viscosity of lithium/sodium CMG (LiNaCMG) in solution. It is shown that LiNaCMG in solution exhibits significant shear thinning behavior. Thus, addition of LiNaCMG to a liquid can modify the rheological behavior of the liquid.

To prepare a 2 wt % solution of LiNaCMG, 1 g of LiNaCMG (sample 2A, General Methods) was added to 49 g of DI water. This preparation was then homogenized for 12-15 seconds at 20,000 rpm to dissolve the LiNaCMG.

To determine the viscosity of the LiNaCMG solution at various shear rates, LiNaCMG samples were subjected to various shear rates using a Brookfield III+ Rheometer equipped with a recirculating bath to control temperature (20° C.) and a YULA15-E(Z) spindle. The shear rate was increased using a gradient program which increased from 0.01-250 rpm and the shear rate was increased by 7.36 (1/s) every 20 seconds. The results of this experiment are listed in Table 20.

TABLE 20

Viscosity of LiNaCMG Solution at Various Shear Rates

| LiNaCMG Sample | LiNaCMG Loading | Viscosity (cPs) @ 44.13 rpm | Viscosity (cPs) @ 80.89 rpm | Viscosity (cPs) @ 161.8 rpm | Viscosity (cPs) @ 250 rpm |
|---|---|---|---|---|---|
| 2A | 2% | 37.6 | 35.22 | 31.83 | 29.62 |

The results summarized in Table 20 indicate that the viscosity of the LiNaCMG solution is reduced as the shear rate is increased. This observation means that LiNaCMG solutions demonstrate significant shear thinning behavior.

Thus, LiNaCMG when dissolved in an aqueous solution not only modifies the viscosity of the solution, but also the rheological properties of the solution. LiNaCMG can therefore be added to an aqueous liquid to modify its rheological profile.

The procedure in this Example could easily be adapted to use lithium carboxymethyl poly alpha-1,3-glucan (LiCMG) instead of LiNaCMG.

Example 16

Effect of Shear Rate on Viscosity of Methyl Poly Alpha-1,3-Glucan

This Example describes the effect of shear rate on the viscosity of MG. It is shown that MG exhibits shear thinning behavior. Thus, addition of MG to a liquid can modify the rheological behavior of the liquid.

To prepare a 2 wt % solution of MG, 1 g of Sample 1 or 2 (General Methods) was added to 49 g of DI water. Each preparation was then homogenized for 15-30 seconds at 20,000 rpm to dissolve the MG.

To determine the viscosity of each MG solution at various shear rates, MG samples were subjected to 10-250 rpm shear rates using a Brookfield DV III+ Rheometer equipped with a recirculating bath to control temperature (20° C.) and an SC4-21 Thermosel® spindle or ULA (ultra low adapter) spindle and adapter set. The shear rate was increased using a gradient program which increased from 10-250 rpm. The shear rate was increased by 7.35 (1/s) every 20 seconds for the ULA spindle and adapter, and by 4.9 (1/s) every 20 seconds for the SC4-21 spindle. The results of this experiment are listed in Table 21.

TABLE 21

Viscosity of MG Solutions at Various Shear Rates

| MG Sample | MG Loading | Spindle | Viscosity (cPs) @ 14.72 rpm | Viscosity (cPs) @ 66.18 rpm | Viscosity (cPs) @ 154.4 rpm | Viscosity (cPs) @ 250 rpm |
|---|---|---|---|---|---|---|
| 1 | 2% | ULA | N/A | 24.84 | 23.42 | 22.67 |
| 2 | 2% | ULA | 254.17 | 228.97 | N/A | N/A |
| 2 | 1% | ULA | N/A | 24.36 | 25.5 | 25.92 |

| MG Sample | MG Loading | Spindle | Viscosity (cPs) @ 14.9 rpm | Viscosity (cPs) @ 63.88 rpm | Viscosity (cPs) @ 152.0 rpm | Viscosity (cPs) @ 232.5 rpm |
|---|---|---|---|---|---|---|
| 2 | 2% | SC4-21 | 193.49 | 257.69 | 226.38 | 208.0 |

The results summarized in Table 21 indicate that the viscosity of the MG solutions is reduced as the shear rate is increased. This observation means that MG solutions demonstrate shear thinning behavior.

Thus, MG when dissolved in an aqueous solution not only modifies the viscosity of the solution, but also the rheological properties of the solution. MG can therefore be added to an aqueous liquid to modify its rheological profile.

Example 17

Effect of Shear Rate on Viscosity of Ethyl Poly Alpha-1,3-Glucan

This Example describes the effect of shear rate on the viscosity of EG. It is shown that EG exhibits shear thinning behavior. Thus, addition of EG to a liquid can modify the rheological behavior of the liquid.

To prepare a 2 wt % solution of EG, 1 g of EG (DoS 1.03, General Methods) was added to 49 g of DI water. This preparation was then homogenized for 15-30 seconds at 20,000 rpm to dissolve the EG. A 1 wt % EG solution was also prepared.

To determine the viscosity of the EG solutions at various shear rates, the EG solutions were subjected to various shear rates using a Brookfield DV III+ Rheometer equipped with a recirculating bath to control temperature (20° C.) and an SC4-21 Thermosel® spindle or ULA spindle and adapter set. The shear rate was increased using a gradient program which increased from 10-250 rpm. The shear rate was increased by 7.35 (1/s) every 20 seconds for the ULA spindle and adapter, and by 4.9 (1/s) every 20 seconds for the SC4-21 spindle. The results of this experiment are listed in Table 22.

TABLE 22

Viscosity of EG Solutions at Various Shear Rates

| EG Loading | Spindle | Viscosity (cPs) @ 14.72 rpm | Viscosity (cPs) @ 66.18 rpm | Viscosity (cPs) @ 154.4 rpm | Viscosity (cPs) @ 250 rpm |
|---|---|---|---|---|---|
| 2% | ULA | 146.76 | 123.24 | N/A | N/A |
| 1% | ULA | 12.76 | 13.25 | 12.27 | 11.90 |

| Loading | Spindle | Viscosity (cPs) @ 10 rpm | Viscosity (cPs) @ 83.47 rpm | Viscosity (cPs) @ 152.0 rpm | Viscosity (cPs) @ 232.5 rpm |
|---|---|---|---|---|---|
| 2% | SC4-21 | N/A | 112.53 | 105.24 | 98.8 |

The results summarized in Table 22 indicate that the viscosity of the EG solutions is reduced as the shear rate is increased. This observation means that EG solutions demonstrate shear thinning behavior.

Thus, EG when dissolved in an aqueous solution not only modifies the viscosity of the solution, but also the rheological properties of the solution. EG can therefore be added to an aqueous liquid to modify its rheological profile.

Example 18

Effect of Shear Rate on Viscosity of Hydroxypropyl Poly Alpha-1,3-Glucan

This Example describes the effect of shear rate on the viscosity of HPG. It is shown that HPG exhibits shear thinning behavior. Thus, addition of HPG to a liquid can modify the rheological behavior of the liquid.

To prepare a 2 wt % solution of the HPG, 1 g of HPG (sample 2, General Methods) was added to 49 g of DI water. This preparation was then homogenized for 15-30 seconds at 20,000 rpm to dissolve the HPG.

To determine the viscosity of the HPG solution at various shear rates, the sample was subjected to various shear rates using a Brookfield DV III+ Rheometer equipped with a recirculating bath to control temperature (20° C.) and a ULA spindle and adapter set. The shear rate was increased using a gradient program which increased from 10-250 rpm and the shear rate was increased by 7.35 (1/s) every 20 seconds for the ULA spindle and adapter. The results of the experiment are listed in Table 23.

TABLE 23

Viscosity of HPG Solutions at Various Shear Rates

| HPG Loading | Spindle | Viscosity (cPs) @ 14.72 rpm | Viscosity (cPs) @ 66.18 rpm | Viscosity (cPs) @ 154.4 rpm | Viscosity (cPs) @ 250 rpm |
|---|---|---|---|---|---|
| 2% | ULA | 45.73 | 35.01 | 26.36 | 20.54 |

The results summarized in Table 23 indicate that the viscosity of the HPG solution is reduced as the shear rate is increased. This observation means that HPG solutions demonstrate shear thinning behavior.

Thus, HPG when dissolved in an aqueous solution not only modifies the viscosity of the solution, but also the rheological properties of the solution. HPG can therefore be added to an aqueous liquid to modify its rheological profile.

Example 19

Effect of Shear Rate on Viscosity of Dihydroxypropyl Poly Alpha-1,3-Glucan

This Example describes the effect of shear rate on the viscosity of dihydroxypropyl poly alpha-1,3-glucan. It is shown that this glucan ether exhibits shear thinning behavior. Thus, addition of dihydroxypropyl poly alpha-1,3-glucan to a liquid can modify the rheological behavior of the liquid.

To prepare 2 wt % solutions of dihydroxypropyl poly alpha-1,3-glucan, 1 g of either sample 1 or 2 (General Methods) of dihydroxypropyl poly alpha-1,3-glucan was added to 49 g of DI water. Each preparation was then homogenized for 12-15 seconds at 20,000 rpm to dissolve the glucan ether.

To determine the viscosity of each solution at various shear rates, each solution was subjected to various shear rates using a Brookfield DV III+ Rheometer equipped with a recirculating bath to hold temperature constant at 20° C. The shear rate was increased using a gradient program which increased from 10-250 rpm and the shear rate was increased by 4.9 (1/s) every 20 seconds. The results of the experiment are listed in Table 24.

TABLE 24

Viscosity of Dihydroxypropyl Poly Alpha-1,3-Glucan Solutions at Various Shear Rates

| Sample | Viscosity (cPs) @ 66.18 rpm | Viscosity (cPs) @ 102.9 rpm | Viscosity (cPs) @ 183.8 rpm | Viscosity (cPs) @ 250 rpm |
|---|---|---|---|---|
| 1 | 26.02 | 25.41 | 24.02 | 23.23 |
| 2 | 26.97 | 25.71 | 24.61 | 24.11 |

The results summarized in Table 24 indicate that the viscosities of the dihydroxypropyl poly alpha-1,3-glucan solutions are reduced as the shear rate is increased. This observation means that this glucan ether demonstrates shear thinning behavior.

Thus, dihydroxypropyl poly alpha-1,3-glucan when dissolved in an aqueous solution not only modifies the viscosity of the solution, but also the rheological properties of the solution. Such ether derivatives of poly alpha-1,3-glucan can therefore be added to an aqueous liquid to modify its rheological profile.

Example 20

Effect of Shear Rate on Viscosity of Dihydroxypropyl Poly Alpha-1,3-Glucan Crosslinked with Borate This Example describes the effect of shear rate on the viscosity of dihydroxypropyl poly alpha-1,3-glucan when crosslinked with borate. It is shown that this composition exhibits shear thickening behavior. Thus, addition of borate-crosslinked dihydroxypropyl poly alpha-1,3-glucan to a liquid can modify the rheological behavior of the liquid.

A dihydroxypropyl poly alpha-1,3-glucan sample was first prepared as described in the General Methods. To a prepare a 2 wt % solution of this sample, 1 g of the sample was added to 49 g of DI water. Each preparation was then homogenized for 12-15 seconds at 20,000 rpm to dissolve the glucan ether.

0.04 g of boric acid was then dissolved in the 2 wt % solution of dihydroxypropyl poly alpha-1,3-glucan prepared above, including an appropriate amount of added DI water, afterwhich pH was adjusted to 9 using 20% sodium hydroxide. This procedure rendered a 0.2 wt % solution of borate-crosslinked dihydroxypropyl poly alpha-1,3-glucan.

To determine the viscosity of this 0.2 wt % solution at various shear rates, the solution was subjected to various shear rates using a Brookfield DV III+ Rheometer equipped with a recirculating bath to hold temperature constant at 20° C. The shear rate was increased using a gradient program which increased from 10-250 rpm and the shear rate was increased by 4.9 (1/s) every 20 seconds. The results of the experiment are listed in Table 25.

TABLE 25

Viscosity of a Borate-Crosslinked Dihydroxypropyl Poly Alpha-1,3-Glucan Solution at Various Shear Rates

| Viscosity (cPs) @ 66.18 rpm | Viscosity (cPs) @ 102.9 rpm | Viscosity (cPs) @ 183.8 rpm | Viscosity (cPs) @ 250 rpm |
|---|---|---|---|
| 285.35 | 304.89 | 407.07 | 437.6 |

The results summarized in Table 25 indicate that the viscosity of the borate-crosslinked dihydroxypropyl poly alpha-1,3-glucan solution is increased as the shear rate is increased. This observation means that this crosslinked glucan ether demonstrates shear thickening behavior. This result is in contrast to the results observed with non-crosslinked dihydroxypropyl poly alpha-1,3-glucan solutions (Example 19), which exhibited shear thinning behavior.

Thus, borate-crosslinked dihydroxypropyl poly alpha-1,3-glucan when dissolved in an aqueous solution not only modifies the viscosity of the solution, but also the rheological properties of the solution. Such crosslinked ether derivatives of poly alpha-1,3-glucan can therefore be added to an aqueous liquid to modify its rheological profile.

Example 21

Effect of Shear Rate on Viscosity of Quaternary Ammonium Poly Alpha-1,3-Glucan

This Example describes the effect of shear rate on the viscosity of trimethylammonium hydroxypropyl poly alpha-1,3-glucan. It is shown that this glucan ether derivative exhibits shear thinning behavior. Thus, addition of trimethylammonium hydroxypropyl poly alpha-1,3-glucan to a liquid can modify the rheological behavior of the liquid.

Various samples of trimethylammonium hydroxypropyl poly alpha-1,3-glucan were prepared as described in the General Methods. To prepare a 2 wt % solution of each sample, 1 g of sample was added to 49 g of DI water. Each preparation was then homogenized for 12-15 seconds at 20,000 rpm to dissolve the trimethylammonium hydroxypropyl poly alpha-1,3-glucan sample in the water. To determine the viscosity of each 2 wt % quaternary ammonium glucan solution at various shear rates, each solution was subjected to various shear rates using a Brookfield DV III+ Rheometer equipped with a recirculating bath to control temperature (20° C.) and a ULA (ultra low adapter) spindle and adapter set. The shear rate was increased using a gradient program which increased from 10-250 rpm and the shear rate was increased by 4.9 1/s every 20 seconds for the ULA spindle and adapter. The results of the experiment are listed in Table 26.

TABLE 26

Viscosity of Quaternary Ammonium Hydroxypropyl Poly Alpha-1,3-Glucan Solutions at Various Shear Rates

| Sample[a] | Viscosity (cPs) @ 66.18 rpm | Viscosity (cPs) @ 102.9 rpm | Viscosity (cPs) @ 183.8 rpm | Viscosity (cPs) @ 250 rpm |
|---|---|---|---|---|
| 1A | 26.26 | 24.95 | 23.42 | 22.6 |
| 1B-1 | 98.87 | 83.22 | 70.27 | 64.43 |
| 1B-2 | 43.76 | 41.53 | 38.24 | 36.57 |
| 1B-3 | 21.53 | 20.08 | 19.16 | 18.72 |
| 1C-1 | 225.81 | 158.76 | 102.02 | 85.6 |
| 1C-2 | 1246.67 | 810.93 | 436.29 | 334.8 |
| 1C-3 | 1601.44 | 992.24 | 563.95 | 421.2 |
| 1E-1 | 739.62 | 493.41 | 269.67 | 224 |

[a]Each sample is described in Table B (General Methods).

The results summarized in Table 26 indicate that the viscosity of each of the quaternary ammonium poly alpha-1,3-glucan solutions is reduced as the shear rate is increased. This observation means that these solutions demonstrate shear thinning behavior.

Thus, trimethylammonium hydroxypropyl poly alpha-1,3-glucan when dissolved in an aqueous solution not only modifies the viscosity of the solution, but also the rheological properties of the solution. This quaternary ammonium glucan can therefore be added to an aqueous liquid to modify its rheological profile.

What is claimed is:

1. A composition comprising a cellulase and a poly alpha-1,3-glucan compound represented by the structure:

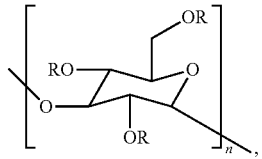

wherein
(i) n is at least 6,
(ii) each R is independently an H or an organic group, and
(iii) the compound has a degree of substitution of about 0.05 to about 3.0 when substituted with the organic group.

2. The composition of claim 1, wherein the compound is substituted by the organic group, and the organic group is selected from the group consisting of carboxy alkyl, hydroxy alkyl, and alkyl.

3. The composition of claim 2, wherein the organic group is selected from the group consisting of carboxymethyl, hydroxypropyl, dihydroxypropyl, hydroxyethyl, methyl, and ethyl.

4. The composition of claim 2, wherein the organic group is a carboxymethyl group.

5. The composition of claim 1, wherein the composition is in the form of a personal care product, household product, or industrial product.

6. The composition of claim 5, wherein the composition is a fabric care product.

7. The composition of claim 1, wherein the composition is an aqueous composition.

8. The composition of claim 7, wherein the composition has a viscosity of at least about 10 cPs.

9. The composition of claim 1, wherein the poly alpha-1,3-glucan compound has one or more of the same organic group.

10. The composition of claim 1, wherein the poly alpha-1,3-glucan compound has two or more different organic groups.

11. The composition of claim 1, wherein the composition comprises a surfactant.

12. The composition of claim 11, wherein the poly alpha-1,3-glucan compound is substituted by the organic group.

13. The composition of claim 1, wherein the composition comprises less than 1 part-per-million of the cellulase.

14. A method for preparing an aqueous composition, the method comprising:
contacting an aqueous composition with a poly alpha-1,3-glucan compound represented by the structure:

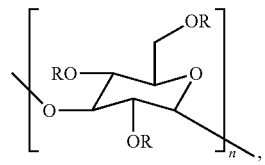

wherein
(i) n is at least 6,
(ii) each R is independently an H or an organic group, and
(iii) the compound has a degree of substitution of about 0.05 to about 3.0 when substituted with the organic group;
and wherein the aqueous composition prepared in said method comprises a cellulase.

15. The method of claim 14, wherein said cellulase is:
(i) comprised in the aqueous composition prior to said contacting step, or
(ii) added to the aqueous composition during or after said contacting step.

16. The method of claim 14, wherein the poly alpha-1,3-glucan compound is substituted by the organic group.

17. The method of claim 14, wherein:
(i) the viscosity of the aqueous composition is increased by said poly alpha-1,3-glucan compound, and/or
(ii) the shear thinning behavior or the shear thickening behavior of the aqueous composition is increased by said poly alpha-1,3-glucan compound.

18. The method of claim 17, wherein the poly alpha-1,3-glucan compound is substituted by the organic group.

19. A method of treating a material, said method comprising: contacting the material with a composition according to claim 7.

20. The method of claim 19, wherein the material comprises fabric.

21. The method of claim 20 wherein the fabric comprises a (i) natural fiber, (ii) synthetic fiber, or a combination of both (i) and (ii).

22. The method of claim 20, wherein the poly alpha-1,3-glucan ether compound adsorbs to the fabric.

* * * * *